(12) United States Patent
Deng et al.

(10) Patent No.: US 11,603,562 B2
(45) Date of Patent: Mar. 14, 2023

(54) METHODS, SYSTEMS, AND COMPOSITIONS FOR NUCLEIC ACID SEQUENCING

(71) Applicant: AXBIO INC., Santa Clara, CA (US)

(72) Inventors: Suhua Deng, Palo Alto, CA (US); Vladimir Ivanovich Bashkirov, Davis, CA (US); Hui Tian, Cupertino, CA (US); Igor Constantin Ivanov, Danville, CA (US)

(73) Assignee: Axbio Inc., Santa Clara, CA (US)

(*) Notice: Subject to any disclaimer, the term of this patent is extended or adjusted under 35 U.S.C. 154(b) by 141 days.

(21) Appl. No.: 16/953,667

(22) Filed: Nov. 20, 2020

(65) Prior Publication Data
US 2021/0139971 A1    May 13, 2021

Related U.S. Application Data

(63) Continuation of application No. PCT/US2019/033376, filed on May 21, 2019.

(60) Provisional application No. 62/674,706, filed on May 22, 2018.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01)

(58) Field of Classification Search
CPC .............................. C12Q 1/6869; C12Q 1/6806
See application file for complete search history.

(56) References Cited

U.S. PATENT DOCUMENTS

| 5,795,782 A | 8/1998 | Church et al. |
| 7,223,541 B2 | 5/2007 | Fuller et al. |
| 7,238,485 B2 | 7/2007 | Akeson et al. |

(Continued)

FOREIGN PATENT DOCUMENTS

| CN | 101914620 A | 12/2010 |
| CN | 101199241 B | 2/2012 |

(Continued)

OTHER PUBLICATIONS

International search report with written opinion dated Oct. 23, 2019 for PCT/US2019/033376.

(Continued)

*Primary Examiner* — Jeremy C Flinders
*Assistant Examiner* — Taryn Kimberly Wood
(74) *Attorney, Agent, or Firm* — Wilson Sonsini Goodrich & Rosati

(57) ABSTRACT

The present disclosure provides a method and systems for processing or analyzing a nucleic acid molecule. A method for processing or analyzing a double-stranded nucleic acid molecule may comprise providing the double-stranded nucleic acid molecule and a double-stranded adapter. The double-stranded adapter may comprise a nicking site within a sense strand or an anti-sense strand of the double-stranded adapter. The double-stranded adapter may then be coupled to the double-stranded nucleic acid molecule, and the double-stranded nucleic acid molecule coupled to the double-stranded adapter may be circularized to generate a circularized double-stranded nucleic acid molecule.

20 Claims, 14 Drawing Sheets

Specification includes a Sequence Listing.

(56) References Cited

U.S. PATENT DOCUMENTS

| | | | |
|---|---|---|---|
| 7,476,503 B2 | 1/2009 | Turner et al. |
| 7,625,701 B2 | 12/2009 | Williams et al. |
| 7,824,887 B2 | 11/2010 | Lee et al. |
| 7,968,702 B2 | 6/2011 | Wegener et al. |
| 7,973,146 B2 | 7/2011 | Shen et al. |
| 8,133,669 B2 | 3/2012 | Lebedev et al. |
| 8,153,375 B2 | 4/2012 | Travers et al. |
| 8,253,174 B2 | 8/2012 | Daniel et al. |
| 8,461,854 B2 | 6/2013 | Chen et al. |
| 8,628,940 B2 | 1/2014 | Sorenson et al. |
| 9,017,937 B1 | 4/2015 | Turner et al. |
| 9,290,800 B2 | 3/2016 | Turner et al. |
| 9,322,062 B2 | 4/2016 | Davis et al. |
| 9,377,437 B2 | 6/2016 | Chen et al. |
| 9,441,271 B2 | 9/2016 | Li et al. |
| 9,494,554 B2 | 11/2016 | Davis et al. |
| 9,533,305 B2 | 1/2017 | Esfandyarpour et al. |
| 9,587,269 B2 | 3/2017 | Myers et al. |
| 9,605,309 B2 | 3/2017 | Davis et al. |
| 9,678,056 B2 | 6/2017 | Turner et al. |
| 9,709,503 B2 | 7/2017 | Turner et al. |
| 9,772,323 B2 | 9/2017 | Turner et al. |
| 9,885,078 B2 | 2/2018 | Jayasinghe et al. |
| 9,910,956 B2 | 3/2018 | Travers et al. |
| 10,036,725 B2 | 7/2018 | Chen |
| 10,344,327 B2 | 7/2019 | Akeson et al. |
| 10,429,375 B2 | 10/2019 | Chen et al. |
| 10,481,144 B2 | 11/2019 | Turner et al. |
| 10,570,449 B2 | 2/2020 | Esfandyarpour et al. |
| 10,612,091 B2 | 4/2020 | Esfandyarpour et al. |
| 10,640,818 B2 | 5/2020 | Pham et al. |
| 10,787,705 B2 | 9/2020 | Esfandyarpour et al. |
| 11,078,530 B2 | 8/2021 | Jayasinghe et al. |
| 11,142,793 B2 | 10/2021 | Turner et al. |
| 2002/0102586 A1 | 8/2002 | Ju et al. |
| 2006/0063171 A1 | 3/2006 | Akeson et al. |
| 2006/0086626 A1 | 4/2006 | Joyce |
| 2011/0005918 A1 | 1/2011 | Akeson et al. |
| 2011/0318748 A1 | 12/2011 | Davidson et al. |
| 2012/0021408 A1 | 1/2012 | Ju et al. |
| 2013/0327644 A1 | 12/2013 | Turner et al. |
| 2014/0087474 A1 | 3/2014 | Huber |
| 2014/0228223 A1 | 8/2014 | Gnirke et al. |
| 2014/0295498 A1 | 10/2014 | Turner et al. |
| 2015/0004600 A1 | 1/2015 | Wang et al. |
| 2015/0259733 A1 | 9/2015 | Li et al. |
| 2015/0268195 A1 | 9/2015 | Kongsuphol et al. |
| 2016/0011169 A1 | 1/2016 | Turner et al. |
| 2016/0021623 A1 | 1/2016 | Guo et al. |
| 2016/0032236 A1 | 2/2016 | Nivala et al. |
| 2016/0216233 A1 | 7/2016 | Hovis et al. |
| 2016/0265048 A1 | 9/2016 | Ju et al. |
| 2016/0304954 A1 | 10/2016 | Lin et al. |
| 2016/0376647 A1 | 12/2016 | Travers et al. |
| 2017/0168040 A1 | 6/2017 | Turner et al. |
| 2017/0260579 A1 | 9/2017 | Fedorov et al. |
| 2018/0073071 A1 | 3/2018 | Ju et al. |
| 2018/0274024 A1 | 9/2018 | Ju et al. |
| 2018/0355436 A1 | 12/2018 | Shuber et al. |
| 2019/0226021 A1 | 7/2019 | Esfandyarpour et al. |
| 2019/0276887 A1 | 9/2019 | Fuller et al. |
| 2020/0181692 A1 | 6/2020 | Oberstrass et al. |
| 2020/0232024 A1 | 7/2020 | Esfandyarpour et al. |
| 2020/0232028 A1 | 7/2020 | Esfandyarpour et al. |
| 2020/0385802 A1 | 12/2020 | Sheikholeslami et al. |
| 2021/0069664 A1 | 3/2021 | Sun et al. |

FOREIGN PATENT DOCUMENTS

| | | | | |
|---|---|---|---|---|
| CN | 101914620 B | 2/2014 | | |
| CN | 1973048 B | 6/2015 | | |
| CN | 101680873 B | 11/2015 | | |
| CN | 103298984 B | 11/2015 | | |
| CN | 103695530 B | 5/2016 | | |
| CN | 104105797 B | 8/2016 | | |
| CN | 103717753 B | 12/2016 | | |
| CN | 104379761 B | 3/2017 | | |
| CN | 103328981 B | 4/2017 | | |
| CN | 108350491 A | 7/2018 | | |
| CN | 105051214 B | 12/2018 | | |
| CN | 105637082 B | 2/2019 | | |
| CN | 105273991 B | 5/2019 | | |
| CN | 109735440 A | 5/2019 | | |
| CN | 109790575 A | 5/2019 | | |
| CN | 105378113 B | 2/2020 | | |
| CN | 111187811 A | 5/2020 | | |
| CN | 104955958 B | 12/2020 | | |
| CN | 106715453 B | 4/2021 | | |
| CN | 106591103 B | 6/2021 | | |
| CN | 107077539 B | 11/2021 | | |
| EP | 0676623 A2 | 10/1995 | | |
| EP | 2307540 B1 | 4/2017 | | |
| EP | 2682460 B1 | 4/2017 | | |
| EP | 2917372 B1 | 4/2020 | | |
| RU | 2529784 C2 | 9/2014 | | |
| WO | WO-03048387 A2 | 6/2003 | | |
| WO | WO-2012141605 A1 | 10/2012 | | |
| WO | WO-2013036929 A1 | * 3/2013 | ............ | B01L 3/5027 |
| WO | WO-2013148400 A1 | 10/2013 | | |
| WO | WO-2014074727 A1 | 5/2014 | | |
| WO | WO-2014182630 A1 | 11/2014 | | |
| WO | WO-2015086654 A1 | 6/2015 | | |
| WO | WO-2015183026 A1 | 12/2015 | | |
| WO | WO-2017184677 A1 | 10/2017 | | |
| WO | WO-2018102350 A1 | 6/2018 | | |
| WO | WO-2018140329 A1 | * 8/2018 | ............ | C12P 19/34 |
| WO | WO-2018183538 A1 | 10/2018 | | |
| WO | WO-2019040546 A1 | 2/2019 | | |
| WO | WO-2019226689 A1 | 11/2019 | | |
| WO | WO-2021021944 A1 | 2/2021 | | |

OTHER PUBLICATIONS

International search report with written opinion dated Nov. 9, 2020 for PCT/US2020/044089.

Klein et al. Hybridization Kinetics Explains CRISPR-Cas Off-Targeting Rules. Cell Reports 22:1413-1423 (Feb. 6, 2018).

Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.

NCBI BLAST Results for TAGGGATAACAGGGTAAT homo sapiens. Retrieved from https://blast.ncbi.nlm.nih.gov/Blast.cgi on May 9, 2019. (10 pages).

New England BioLabs Inc. Nt.BspQI Product Information. Retrieved online at https://www.neb.eom/products/r0644-ntbspqi#Product%20Information. Accessed May 16, 2019. (8 pages).

Song, et al. CRISPR-Cas9 D10A Nickase-Assisted Genome Editing in Lactobacillus casei. Appl Environ Microbiol. Oct. 31, 2017;83(22):e01259-17. doi: 10.1128/AEM.01259-17. Print Nov. 15, 2017.

Stranges, et al. Design and characterization of a nanopore-coupled polymerase for single-molecule DNA sequencing by synthesis on an electrode array. Proc Natl Acad Sci USA. Nov. 1, 2016;113(44):E6749-E6756. doi: 10.1073/pnas.1608271113. Epub Oct. 11, 2016.

Thermo Fisher Scientific. User Guide: Ajul, 5 U/uL, 100U. Catalog No. ER1951. 3 pages. (2012).

Thermo Fisher Scientific. User Guide: I-Scel, 10 U/uL, 250U. Catalog No. ER1771. 4 pages. (2016).

U.S. Appl. No. 61/789,354, inventors Pham; Thang Tat et al., filed Mar. 15, 2013.

Daniels, et al. Label-Free Impedance Biosensors: Opportunities and Challenges. Electroanalysis. Jun. 2007;19(12):1239-1257.

EMBOSS. EMBOSS Needle: Pairwise Sequence Alignment (NUCLEOTIDE). Available at http://www.ebi.ac.uk/Tools/psa/emboss_needle/nucleotide.html. Accessed on Oct. 10, 2016.

EMBOSS. EMBOSS Water: Pairwise Sequence Alignment (NUCLEOTIDE). Available at http://www.ebi.ac.uk/Tools/psa/emboss_water/nucleotide.html. Accessed on Oct. 10, 2016.

(56) References Cited

OTHER PUBLICATIONS

Fuller, et al. Real-time single-molecule electronic DNA sequencing by synthesis using polymer-tagged nucleotides on a nanopore array. Proc Natl Acad Sci USA. May 10, 2016;113(19):5233-5238. doi: 10.1073/pnas.1601782113. Epub Apr. 18, 2016.

Hutter, et al. Labeled nucleoside triphosphates with reversibly terminating aminoalkoxyl groups. Nucleosides Nucleotides Nucleic Acids. Nov. 2010;29(11):879-95. doi: 10.1080/15257770.2010.536191.

Katz, et al. Probing Biomolecular Interactions at Conductive and Semiconductive Surfaces by Impedance Spectroscopy: Routes to Impedimetric Immunosensors, DNA—Sensors, and Enzyme Biosensors. Electroanalysis 15 (2003): 913-947.

Kumar et al. PEG-Labeled Nucleotides and Nanopore Detection for Single Molecule DNA Sequencing by Synthesis. Scientific Reports 2:1-8 (2012).

Kumar, et al. Terminal phosphate labeled nucleotides: synthesis, applications, and linker effect on incorporation by DNA polymerases. Nucleosides Nucleotides Nucleic Acids. 2005;24(5-7):401-8.

Myadelets, et al. M 99 Histology, cytology and embryology of humans. Part 1. Cytology, embryology and general histology: textbook [in Russian] / O.D. Myadelets—Vitebsk: VSMU, 2014—439 p. 199 (English Machine Translation).

NCBI. Basic Local Alignment Search Tool. BLAST algorithm. Available at https://blast.ncbi.nlm.nih.gov/Blast.cgi. Accessed on Jan. 3, 2017.

Nelson J.R. et al. TempliPhi, phi29 DNA polymerase based rolling circle amplification of templates for DNA sequencing. Biotechniques. Jun. 2002;Suppl:44-7. PMID: 12083397.

Palla, et al. DNA sequencing by synthesis using 3'-O-azidomethyl nucleotide reversible terminators and surface-enhanced Raman spectroscopic detection. RSC Adv. Jan. 1, 2014;4(90):49342-49346. doi: 10.1039/C4RA08398A.

* cited by examiner

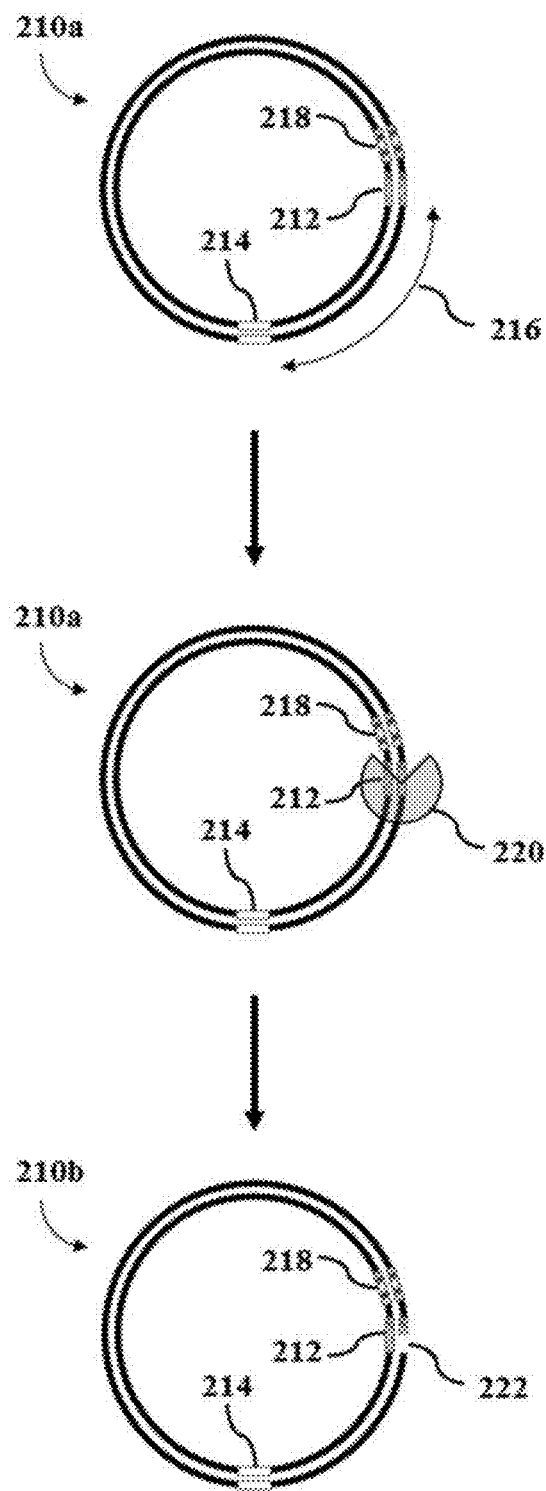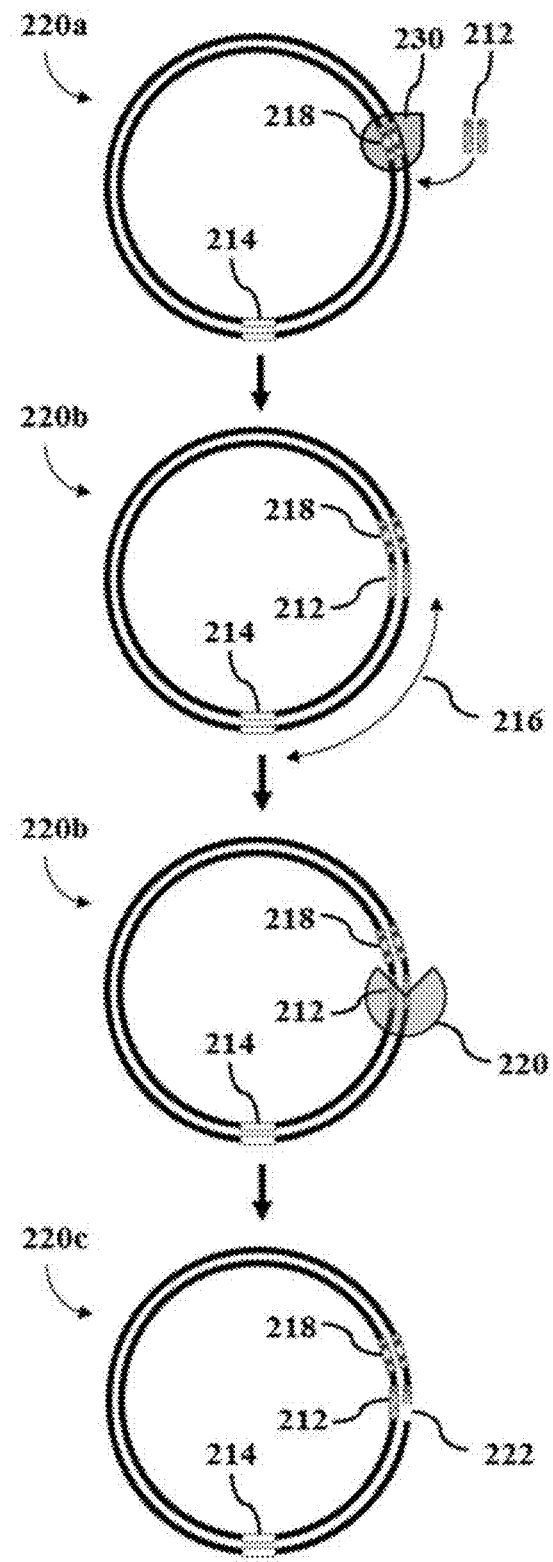
FIG. 2A
FIG. 2B

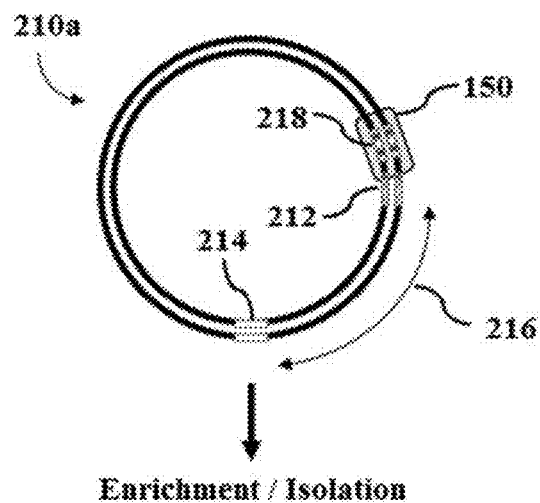
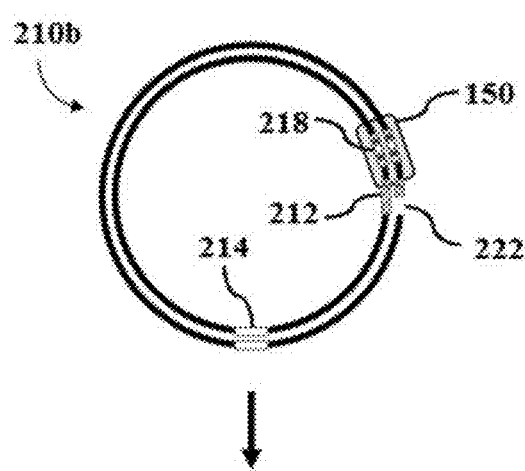
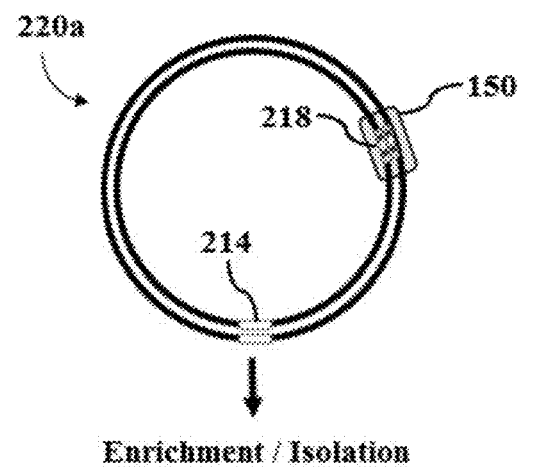
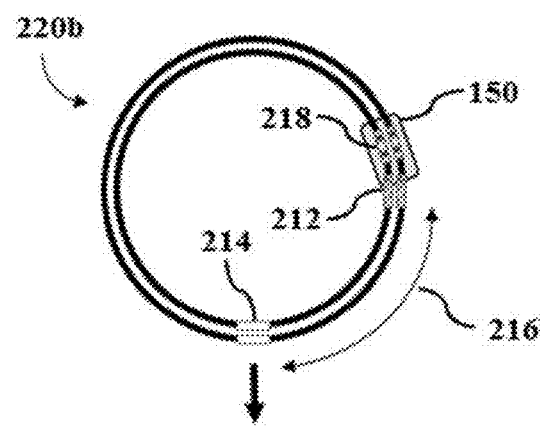
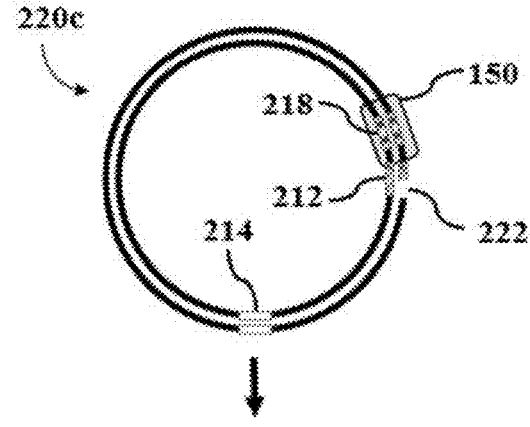
*FIG. 2C*  *FIG. 2D*

METHODS, SYSTEMS, AND COMPOSITIONS FOR NUCLEIC ACID SEQUENCING

CROSS-REFERENCE

The present application is a continuation of International Application No. PCT/US2019/033376, filed May 21, 2019, which claims the benefit of U.S. Provisional Application No. 62/674,706, filed May 22, 2018, each of which is entirely incorporated herein by reference.

SEQUENCE LISTING

The instant application contains a Sequence Listing which has been submitted electronically in ASCII format and is hereby incorporated by reference in its entirety. Said ASCII copy, created on Nov. 20, 2020, is named 52486-701_601_SL.txt and is 753 bytes in size.

BACKGROUND

Nucleic acid sequencing may be used to provide sequence information for a nucleic acid sample. Such sequence information may be helpful in diagnosing or treating a subject (e.g., an individual, a patient, etc.) of a condition (e.g., a disease). For example, nucleic acid sequence information of a subject may be used to identify, diagnose, or develop a treatment for one or more genetic diseases. In another example, nucleic acid sequence information of one or more pathogens may lead to treatment for one or more contagious diseases.

In some cases, a method for nucleic acid sequencing may include generating a nick a strand of a circular double-stranded nucleic acid and binding of a polymerase to the nick. A resulting complex that comprises the polymerase and the circular double-stranded nucleic acid complex may be associated with (e.g., coupled to or brought adjacent to) a sequencing moiety (e.g., a nanopore), and a growing strand having complementarity to at least a portion of the double-stranded nucleic acid may be generated (e.g., via rolling circle amplification (RCA)) for sequencing by the sequencing moiety. Such method may be used for whole genome sequencing or detection of one or more sequence variants (e.g., mutations) within a pool of nucleic acids.

Detection of one or more rare sequence variants (e.g., mutations) may be valuable for healthcare. Detection of rare sequence variants may be important for and early detection of one or more pathological mutations. Detection of one or more cancer-associated mutations (e.g., point mutations) in clinical samples may improve identification of one or more minimal residual diseases during chemotherapy or detection of tumor cells in relapsing patients. Additionally, such detection of the mutation(s) may be important for assessment of exposure to environmental mutagens, monitoring endogenous DNA repair, or studying accumulation of one or more somatic mutations in aging individuals. Alternatively or in addition to, the detection or rare sequence variant(s) may enhance prenatal diagnosis and enable characterization of fetal cells present in maternal blood.

SUMMARY

In an aspect, the present disclosure provides a method for processing or analyzing a double-stranded nucleic acid molecule, comprising: (a) providing (i) the double-stranded nucleic acid molecule and (ii) a double-stranded adapter having a nicking site within a sense strand or an anti-sense strand of the double-stranded adapter; (b) coupling the double-stranded adapter to the double-stranded nucleic acid molecule; and (c) circularizing the double-stranded nucleic acid molecule coupled to the double-stranded adapter to generate a circularized double-stranded nucleic acid molecule.

In some embodiments, the double-stranded nucleic acid molecule and the double-stranded adapter are heterologous to one another. In some embodiments, the double-stranded nucleic acid molecule and the double-stranded adapter are provided in a cell-free composition. In some embodiments, (b) or (c) is performed in a cell-free condition. In some embodiments, (b) and (c) are performed in a cell-free condition.

In some embodiments, the coupling comprises (i) coupling the sense strand of the double-stranded adapter to a sense strand of the double-stranded nucleic acid molecule, or (ii) coupling the anti-sense strand of the double-stranded adapter to an anti-sense strand of the double-stranded nucleic acid molecule. In some embodiments, the coupling comprises (i) coupling the sense strand of the double-stranded adapter to the sense strand of the double-stranded nucleic acid molecule and (ii) coupling the anti-sense strand of the double-stranded adapter to the anti-sense strand of the double-stranded nucleic acid molecule.

In some embodiments, the nicking site is part of a sense strand of the circularized double-stranded nucleic acid molecule. In some embodiments, the nicking site is part of an anti-sense strand of the circularized double-stranded nucleic acid molecule.

In some embodiments, the method further comprises subjecting the double-stranded nucleic acid molecule to sequencing from the nicking site of the double-stranded adapter. In some embodiments, the sequencing comprises (i) subjecting the double-stranded nucleic acid molecule to an extension reaction from the nicking site of the double-stranded adapter to generate a growing strand having sequence complementarity to at least a portion of a strand of the double-stranded nucleic acid molecule, and (ii) obtaining sequence information of at least a portion of the growing strand. In some embodiments, the obtaining the sequence information comprises detecting the at least the portion of the growing strand. In some embodiments, the extension reaction comprises bringing the double-stranded nucleic acid molecule in contact with a nucleotide coupled to a tag under conditions sufficient to incorporate the nucleotide into the growing strand, and wherein obtaining the sequence information comprises detecting the tag. In some embodiments, the method further comprises releasing the tag from the nucleotide upon incorporation of the nucleotide into the growing strand. In some embodiments, the extension reaction is performed without use of an oligonucleotide primer. In some embodiments, the extension reaction comprises rolling circle amplification.

In some embodiments, the sequencing comprises (i) subjecting the double-stranded nucleic acid molecule to a cleavage reaction from the nicking site of the double-stranded adapter to cleave at least a portion of a strand of the double-stranded nucleic acid molecule, and (ii) obtaining sequence information of the at least the portion of the strand. In some embodiments, the obtaining the sequence information comprises detecting the at least the portion of the strand. In some embodiments, the sequencing comprises a nanopore-based sequencing. In some embodiments, at least a portion of the double-stranded nucleic acid molecule has or is suspected of having one or more sequencing variants in comparison to at least one reference sequence, and wherein the sequencing is to identify a presence of the at least the portion of the double-stranded nucleic acid molecule. In some embodiments, the one or more sequencing variants indicate a mutation in a gene. In some embodiments, the at least one reference sequence comprises a consensus sequence of at least a portion of the gene.

In some embodiments, the method further comprises, prior to (b), amplifying the double-stranded nucleic acid molecule to generate a plurality of copies of the double-stranded nucleic acid molecule.

In some embodiments, the double-stranded nucleic acid molecule comprises a recognition sequence, further comprising enriching for the double-stranded nucleic acid molecule from a pool of random nucleic acid molecules based at least in part on the recognition sequence. In some embodiments, the enriching comprises generating a selected library of double-stranded nucleic acid molecules, wherein each double-stranded nucleic acid molecule of at least 5% of the selected library comprises the recognition sequence. In some embodiments, each double-stranded nucleic acid molecule of at least 10%, 20%, 30%, 40%, 50%, 60%, 70%, 80%, 90%, or 95% of the selected library comprises the recognition sequence. In some embodiments, a probability of occurrence of the recognition sequence without any mismatch is at most once in every $1\times10^4$ base pairs. In some embodiments, the probability of occurrence of the recognition sequence without any mismatch is at most once in every $5\times10^4$, $7\times10^4$, $1\times10^5$, $1\times10^6$, $1\times10^7$, $1\times10^8$, $1\times10^9$, $1\times10^{10}$, $1\times10^{11}$, or $1\times10^{12}$ base pairs. In some embodiments, the recognition sequence comprises at least 5 bases. In some embodiments, the recognition sequence comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases. In some embodiments, the enriching comprises (i) binding a recognition moiety having complementarity to the recognition sequence to the double-stranded nucleic acid molecule to form a recognition complex and (ii) extracting the recognition complex. In some embodiments, the enriching is performed prior to (a) or subsequent to (b). In some embodiments, the enriching is performed prior to (a) and subsequent to (b).

In some embodiments, the double-stranded nucleic acid molecule is from or derived from a biological sample of a subject. In some embodiments, the biological sample comprises a cell-free biological sample of the subject. In some embodiments, the double-stranded nucleic acid molecule is from or derived from a cell-free nucleic acid molecule from the cell-free biological sample. In some embodiments, the cell-free nucleic acid molecule comprises a circulating tumor nucleic acid molecule or an amniotic fluid nucleic acid molecule. In some embodiments, the biological sample comprises a tissue sample of the subject. In some embodiments, the double-stranded nucleic acid molecule is from or derived from a genomic nucleic acid molecule from the tissue sample. In some embodiments, the tissue sample is derived from the group consisting of: infected tissue, diseased tissue, malignant tissue, calcified tissue, healthy tissue, and a combination thereof. In some embodiments, the tissue sample is from the malignant tissue comprising a tumor, sarcoma, leukemia, or a derivative thereof.

In some embodiments, the double-stranded nucleic acid molecule comprises DNA, complimentary DNA, a derivative thereof, or a combination thereof. In some embodiments, the double-stranded nucleic acid molecule comprises RNA.

In another aspect, the present disclosure provides a reaction mixture for processing or analyzing a double-stranded nucleic acid molecule, comprising: a composition comprising (i) the double-stranded nucleic acid molecule and (ii) a double-stranded adapter having a nicking site within a sense strand or an anti-sense strand of the double-stranded adapter; and at least one enzyme that (i) couples the double-stranded adapter to the double-stranded nucleic acid molecule, and (ii) circularizes the double-stranded nucleic acid molecule coupled to the double-stranded adapter to generate a circularized double-stranded nucleic acid molecule.

In some embodiments, the double-stranded nucleic acid molecule and the double-stranded adapter are heterologous to one another. In some embodiments, the reaction mixture is a cell-free reaction mixture.

In some embodiments, the at least one enzyme couples (i) the sense strand of the double-stranded adapter to a sense strand of the double-stranded nucleic acid molecule, or (ii) the anti-sense strand of the double-stranded adapter to an anti-sense strand of the double-stranded nucleic acid molecule. In some embodiments, the at least one enzyme couples (i) the sense strand of the double-stranded adapter to the sense strand of the double-stranded nucleic acid molecule and (ii) the anti-sense strand of the double-stranded adapter to the anti-sense strand of the double-stranded nucleic acid molecule. In some embodiments, the at least one enzyme ligates the double-stranded adapter to the double-stranded nucleic acid molecule. In some embodiments, the at least one enzyme comprises a ligase, a recombinase, a polymerase, a functional variant thereof, or a combination thereof.

In some embodiments, the nicking site is part of a sense strand of the circularized double-stranded nucleic acid molecule. In some embodiments, the nicking site is part of an anti-sense strand of the circularized double-stranded nucleic acid molecule.

In some embodiments, the reaction mixture further comprises at least a second enzyme that performs an extension reaction to generate a growing strand having sequence complementarity to at least a portion of a strand of the double-stranded nucleic acid molecule. In some embodiments, prior to coupling of the double-stranded adapter to the double-stranded nucleic acid molecule, the at least the second enzyme generates the growing strand.

In some embodiments, subsequent to coupling of the double-stranded adapter to the double-stranded nucleic acid molecule, the at least the second enzyme performs the extension reaction from the nicking site of the double-stranded adapter to generate the growing strand. In some embodiments, the reaction mixture further comprises at least one nucleotide coupled to a tag, wherein the at least the second enzyme incorporates the nucleotide into the growing strand. In some embodiments, the at least the second enzyme releases the tag from the nucleotide upon incorporation of the nucleotide into the growing strand. In some embodiments, the at least the second enzyme performs the extension reaction without use of an oligonucleotide primer. In some embodiments, the extension reaction comprises rolling circle amplification. In some embodiments, the at least the second enzyme comprises a polymerase.

In some embodiments, the reaction mixture further comprises at least a third enzyme that performs a cleavage reaction from the nicking site of the double-stranded adapter to cleave at least a portion of a strand of the double-stranded nucleic acid molecule.

In some embodiments, at least a portion of the double-stranded nucleic acid molecule has or is suspected of having one or more variants in comparison to at least one reference sequence. In some embodiments, the reaction mixture is to prepare at least one composition for sequencing to identify a presence of the at least the portion of the double-stranded nucleic acid molecule. In some embodiments, the one or more sequencing variants indicate a mutation in a gene. In some embodiments, the at least one reference sequence comprises a consensus sequence of at least a portion of the gene.

In some embodiments, the double-stranded nucleic acid molecule comprises a recognition sequence. In some embodiments, the reaction mixture further comprises a recognition moiety that associates with the recognition sequence to enrich for at least the double-stranded nucleic acid molecule from a pool of random nucleic acid molecules in the composition based at least in part on the recognition sequence. In some embodiments, the recognition moiety comprises at least one oligonucleotide having complementarity to at least the recognition sequence. In some embodiments, the composition comprises a selected library of double-stranded nucleic acid molecules, wherein each double-stranded nucleic acid molecule of at least 5% of the library comprises the recognition sequence. In some embodiments, each double-stranded nucleic acid molecule of at least 10%, 20%, 30%, 40%, 50%, 60%, 70%, 80%, 90%, or 95% of the selected library comprises the recognition sequence. In some embodiments, a probability of occurrence of the recognition sequence without any mismatch is at most once in every $1\times10^4$ base pairs. In some embodiments, the probability of occurrence of the recognition sequence without any mismatch is at most once in every $5\times10^4$, $7\times10^4$, $1\times10^5$, $1\times10^6$, $1\times10^7$, $1\times10^8$, $1\times10^9$, $1\times10^{10}$, $1\times10^{11}$, or $1\times10^{12}$ base pairs. In some embodiments, the recognition sequence comprises at least 5 bases. In some embodiments, the recognition sequence comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases.

In some embodiments, the double-stranded nucleic acid molecule is from or derived from a biological sample of a subject. In some embodiments, the biological sample comprises a cell-free biological sample of the subject. In some embodiments, the double-stranded nucleic acid molecule is from or derived from a cell-free nucleic acid molecule from the cell-free biological sample. In some embodiments, the cell-free nucleic acid molecule comprises a circulating tumor nucleic acid molecule or an amniotic fluid nucleic acid molecule. In some embodiments, the biological sample comprises a tissue sample of the subject. In some embodiments, the double-stranded nucleic acid molecule is from or derived from a genomic nucleic acid molecule from the tissue sample. In some embodiments, the tissue sample is derived from the group consisting of: infected tissue, diseased tissue, malignant tissue, calcified tissue, healthy tissue, and a combination thereof. In some embodiments, the tissue sample is from the malignant tissue comprising a tumor, sarcoma, leukemia, or a derivative thereof.

In some embodiments, the double-stranded nucleic acid molecule comprises DNA, complimentary DNA, a derivative thereof, or a combination thereof. In some embodiments, the double-stranded nucleic acid molecule comprises RNA.

In a different aspect, the present disclosure provides a library of circularized double-stranded nucleic acid molecules comprising (i) a double-stranded nucleic acid domain that is coupled to (ii) a double-stranded adapter domain that comprises a nicking site within a sense strand or an anti-sense strand of the double-stranded adapter domain, wherein each circularized double-stranded nucleic acid molecule of at least 5% of the library comprises a recognition sequence.

In some embodiments, the nicking site is present within the double-stranded adapter domain prior to coupling of the double-stranded adapter domain to the double-stranded nucleic acid domain. In some embodiments, the double-stranded nucleic acid domain and the double-stranded adapter domain are heterologous to one another. In some embodiments, the library is in a cell-free composition.

In some embodiments, at least a portion of the circularized double-stranded nucleic acid domain has or is suspected of having one or more sequencing variants in comparison to at least one reference sequence. In some embodiments, the one or more sequencing variants indicate a mutation in a gene. In some embodiments, the at least one reference sequence comprises a consensus sequence of at least a portion of the gene.

In some embodiments, each circularized double-stranded nucleic acid molecule of at least 10%, 20%, 30%, 40%, 50%, 60%, 70%, 80%, 90%, or 95% of the selected library comprises the recognition sequence. In some embodiments, a probability of occurrence of the recognition sequence without any mismatch is at most once in every $1\times10^4$ base pairs. In some embodiments, the probability of occurrence of the recognition sequence without any mismatch is at most once in every $5\times10^4$, $7\times10^4$, $\times10^5$, $1\times10^6$, $1\times10^7$, $1\times10^8$, $1\times10^9$, $1\times10^{10}$, $1\times10^{11}$, $1\times10^{12}$ base pairs. In some embodiments, the recognition sequence comprises at least 5 specific bases. In some embodiments, the recognition sequence comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases.

In some embodiments, the nicking site is part of a sense strand of the circularized double-stranded nucleic acid molecule. In some embodiments, the nicking site is part of an anti-sense strand of the circularized double-stranded nucleic acid molecule.

In some embodiments, the circularized double-stranded nucleic acid molecule is from or derived from a biological sample of a subject. In some embodiments, the biological sample comprises a cell-free biological sample of the subject. In some embodiments, the double-stranded nucleic acid molecule is from or derived from a cell-free nucleic acid molecule from the cell-free biological sample. In some embodiments, the cell-free nucleic acid molecule comprises a circulating tumor nucleic acid molecule or an amniotic fluid nucleic acid molecule. In some embodiments, the biological sample comprises a tissue sample of the subject. In some embodiments, the double-stranded nucleic acid molecule is from or derived from a genomic nucleic acid molecule from the tissue sample. In some embodiments, the tissue sample is derived from the group consisting of: infected tissue, diseased tissue, malignant tissue, calcified tissue, healthy tissue, and a combination thereof. In some embodiments, the tissue sample is from the malignant tissue comprising a tumor, sarcoma, leukemia, or a derivative thereof.

In some embodiments, the circularized double-stranded nucleic acid molecule comprises DNA, complimentary DNA, a derivative thereof, or a combination thereof. In some embodiments, the circularized double-stranded nucleic acid molecule comprises RNA.

In a different aspect, the present disclosure provides a method for processing or analyzing a circular nucleic acid molecule, comprising: (a) providing a cell-free composition comprising the circular nucleic acid molecule that comprises (i) a target region and (ii) a nicking site at a known distance away from the target region; and (b) generating a nick at the nicking site of the circular nucleic acid molecule. In some embodiments, (b) is performed in a cell-free condition.

In some embodiments, the nicking site is at no more than 100,000 nucleotides away from the target site. In some embodiments, the nicking site is at no more than 50,000, 10,000, 5,000, 1,000, 500, 400, 300, 200, 100, 90, 80, 70, 60, 50, 40, 30, 25, 20, 15, 10, or 5 nucleotides away from the target site. In some embodiments, the target site comprises at most about 500,000 nucleotides. In some embodiments, the target site comprises at most about 100,000, 50,000, 10,000, 5,000, 1,000, 500, 400, 300, 200, 100, 50, 40, 30, 25, 20, 15, 10, 9, 8, 7, 6, 5, 4, 3, 2, or 1 nucleotide.

In some embodiments, the nucleic acid molecule comprises a double-stranded nucleic acid molecule. In some embodiments, the nicking site is part of a sense strand of the circular nucleic acid molecule. In some embodiments, the nicking site is part of an anti-sense strand of the circular nucleic acid molecule. In some embodiments, the method further comprises determining the nicking site based at least in part on a positon of the target site relative to at least one reference sequence. In some embodiments, the at least one reference sequence comprises a consensus sequence of at least a portion of the gene. In some embodiments, the nicking site is endogenous to the circular nucleic acid molecule. In some embodiments, the nicking site is exogenous to the circular nucleic acid molecule, and wherein the determining comprises inserting the exogenous nicking site to the circular nucleic acid molecule.

In some embodiments, the nucleic acid molecule further comprises a nickase binding site specific for the nickase, further comprising, in (b), providing a nickase to the nucleic acid molecule under conditions sufficient for the nickase to associate with the nickase binding site and generate the nick. In some embodiments, a probability of occurrence of the nickase binding site without any mismatch is at most once in every $1 \times 10^4$ base pairs. In some embodiments, the probability of occurrence of the nickase binding site without any mismatch is at most once in every $5 \times 10^4$, $7 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ base pairs. In some embodiments, the nickase binding site comprises at least 5 bases. In some embodiments, the nickase binding site comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases. In some embodiments, the nickase binding site is endogenous to the nucleic acid molecule. In some embodiments, the nickase binding site is exogenous to the nucleic acid molecule. In some embodiments, the method further comprises, prior to (b), inserting the exogenous nickase binding site to the nucleic acid molecule. In some embodiments, the method further comprises circularizing the nucleic acid molecule prior to the inserting. In some embodiments, the method further comprises circularizing the nucleic acid molecule subsequent to the inserting. In some embodiments, the nickase binding site is at no more than 30 nucleotides away from the nicking site. In some embodiments, the nickase binding site is at no more than 25, 20, 19, 18, 17, 16, 15, 14, 13, 12, 11, 10, 9, 8, 7, 6, 5, 4, 3, 2, or 1 nucleotide away from the nicking site. In some embodiments, the nickase binding site comprises the nicking site.

In some embodiments, the method further comprises subjecting the circular nucleic acid molecule to sequencing. In some embodiments, the sequencing comprises (i) subjecting the circular nucleic acid molecule to an extension reaction from the nick to generate a growing strand having sequence complementarity to at least a portion of a strand of the circular nucleic acid molecule, and (ii) obtaining sequence information of at least a portion of the growing strand. In some embodiments, the obtaining the sequence information comprises detecting the at least the portion of the growing strand. In some embodiments, the extension reaction comprises bringing the circular nucleic acid molecule in contact with a nucleotide coupled to a tag under conditions sufficient to incorporate the nucleotide into the growing strand, and wherein obtaining the sequence information comprises detecting the tag. In some embodiments, the method further comprises releasing the tag from the nucleotide upon incorporation of the nucleotide into the growing strand. In some embodiments, the extension reaction is performed without use of an oligonucleotide primer. In some embodiments, the extension reaction comprises rolling circle amplification.

In some embodiments, the sequencing comprises (i) subjecting the circular nucleic acid molecule to a cleavage reaction from the nick to cleave at least a portion of a strand of the double-stranded nucleic acid molecule, and (ii) obtaining sequence information of the at least the portion of the strand. In some embodiments, the obtaining the sequence information comprises detecting the at least the portion of the strand. In some embodiments, the sequencing comprises a nanopore-based sequencing. In some embodiments, at least a portion of the target site has or is suspected of having one or more sequencing variants in comparison to at least one reference sequence, and wherein the sequencing is to identify a presence of the at least the portion of the target site. In some embodiments, the one or more sequencing variants indicate a mutation in a gene. In some embodiments, the at least one reference sequence comprises a consensus sequence of at least a portion of the gene.

In some embodiments, the method further comprises, prior to (a), circularizing at least a linear nucleic acid molecule to the circular nucleic acid molecule. In some embodiments, the at least the linear nucleic acid molecule is part of an amplification product. In some embodiments, the method further comprises, prior to (b), amplifying the circular nucleic acid molecule to generate a plurality of copies of the circular nucleic acid molecule.

In some embodiments, the circular nucleic acid molecule comprises a recognition sequence, further comprising enriching for the circular nucleic acid molecule from a pool of random nucleic acid molecules based at least in part on the recognition sequence. In some embodiments, the enriching comprises generating a selected library of circular nucleic acid molecules, wherein each circular nucleic acid molecule of at least 5% of the selected library comprises the recognition sequence. In some embodiments, each circular nucleic acid molecule of at least 10%, 20%, 30%, 40%, 50%, 60%, 70%, 80%, 90%, or 95% of the selected library comprises the recognition sequence. In some embodiments, a probability of occurrence of the recognition sequence without any mismatch is at most once in every $1 \times 10^4$ base pairs. In some embodiments, the probability of occurrence of the recognition sequence without any mismatch is at most once in every $5 \times 10^4$, $7 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ base pairs. In some embodiments, the recognition sequence comprises at least 5 bases. In some embodiments, the recognition sequence comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases. In some embodiments, the enriching comprises (i) binding a recognition moiety having complementarity to the recognition sequence to the circular nucleic acid molecule to form a recognition complex and (ii) extracting the recognition complex. In some embodiments, the enriching is performed prior to (a) or subsequent to (b). In some embodiments, the enriching is performed prior to (a) and subsequent to (b).

In some embodiments, the circular nucleic acid molecule is from or derived from a biological sample of a subject. In some embodiments, the biological sample comprises a cell-free biological sample of the subject. In some embodiments, the circular nucleic acid molecule is derived from a cell-free nucleic acid molecule from the cell-free biological sample. In some embodiments, the cell-free nucleic acid molecule comprises a circulating tumor nucleic acid molecule or an amniotic fluid nucleic acid molecule. In some embodiments, the biological sample comprises a tissue sample of the subject. In some embodiments, the circular nucleic acid molecule derived from a genomic nucleic acid molecule from the tissue sample. In some embodiments, the tissue sample is derived from the group consisting of: infected tissue, diseased tissue, malignant tissue, calcified tissue, healthy tissue, and a combination thereof. In some embodiments, the tissue sample is from the malignant tissue comprising a tumor, sarcoma, leukemia, or a derivative thereof.

In some embodiments, the circular nucleic acid molecule comprises DNA, complimentary DNA, a derivative thereof, or a combination thereof. In some embodiments, the circular nucleic acid molecule comprises RNA.

In a different aspect, the present disclosure provides a reaction mixture for processing or analyzing a circular nucleic acid molecule, comprising: a cell-free composition comprising the circular nucleic acid molecule that comprises (i) a target site and (ii) a nicking site at a known distance away from the target site; and at least one enzyme that generates a nick at the nicking site of the circular nucleic acid molecule. In some embodiments, the reaction mixture is a cell-free reaction mixture.

In some embodiments, the nicking site is at no more than 100,000 nucleotides away from the target site. In some embodiments, the nicking site is at no more than 50,000, 10,000, 5,000, 1,000, 500, 400, 300, 200, 100, 90, 80, 70, 60, 50, 40, 30, 25, 20, 15, 10, or 5 nucleotides away from the target site.

In some embodiments, the target site comprises at most about 500,000 nucleotides. In some embodiments, the target site comprises at most about 100,000, 50,000, 10,000, 5,000, 1,000, 500, 400, 300, 200, 100, 50, 40, 30, 25, 20, 15, 10, 9, 8, 7, 6, 5, 4, 3, 2, or 1 nucleotide.

In some embodiments, the circular nucleic acid molecule comprises a circular double-stranded nucleic acid molecule. In some embodiments, the nick is at a sense strand of the circular double-stranded nucleic acid molecule. In some embodiments, the nick is at an anti-sense strand of the circular double-stranded nucleic acid molecule. In some embodiments, the nicking site is endogenous to the circular nucleic acid molecule. In some embodiments, the nicking site is exogenous to the circular nucleic acid molecule.

In some embodiments, the nucleic acid molecule further comprises an enzyme binding site specific for the at least one enzyme. In some embodiments, a probability of occurrence of the enzyme binding site without any mismatch is at most once in every $1\times10^4$ base pairs. In some embodiments, the probability of occurrence of the enzyme binding site without any mismatch is at most once in every $5\times10^4$, $7\times10^4$, $1\times10^5$, $1\times10^6$, $1\times10^7$, $1\times10^8$, $1\times10^9$, $1\times10^{10}$, $1\times10^{11}$, $1\times10^{12}$ base pairs. In some embodiments, the enzyme binding site comprises at least 5 bases. In some embodiments, the enzyme binding site comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases. In some embodiments, the enzyme binding site is endogenous to the circular nucleic acid molecule. In some embodiments, the enzyme binding site is exogenous to the circular nucleic acid molecule. In some embodiments, the enzyme binding site is at no more than 30 nucleotides away from the nicking site. In some embodiments, the enzyme binding site is at no more than 25, 20, 19, 18, 17, 16, 15, 14, 13, 12, 11, 10, 9, 8, 7, 6, 5, 4, 3, 2, or 1 nucleotide away from the nicking site. In some embodiments, the enzyme binding site comprises the nicking site.

In some embodiments, the reaction mixture further comprises at least a second enzyme that performs an extension reaction from the nick to generate a growing strand having sequence complementarity to at least a portion of the circular nucleic acid molecule. In some embodiments, the circular nucleic acid molecule is a circular double-stranded nucleic acid molecule, and wherein the growing strand has sequence complementarity to at least a portion of a strand of the circular double-stranded nucleic acid molecule. In some embodiments, the reaction mixture further comprises at least one nucleotide coupled to a tag, wherein the at least the second enzyme incorporates the nucleotide into the growing strand. In some embodiments, the at least the second enzyme releases the tag from the nucleotide upon incorporation of the nucleotide into the growing strand. In some embodiments, the at least the second enzyme performs the extension reaction without use of an oligonucleotide primer. In some embodiments, the extension reaction comprises rolling circle amplification. In some embodiments, the at least the second enzyme comprises a polymerase.

In some embodiments, the reaction mixture further comprises at least a third enzyme that performs a cleavage reaction from the nick to cleave at least a portion of the circular nucleic acid molecule. In some embodiments, the circular nucleic acid molecule is a circular double-stranded nucleic acid molecule, and wherein the at least the third enzyme cleaves at least a portion of a strand of the circular double-stranded nucleic acid molecule.

In some embodiments, at least a portion of the circular nucleic acid molecule has or is suspected of having one or more variants in comparison to at least one reference sequence. In some embodiments, the reaction mixture is to prepare at least one composition for sequencing to identify a presence of the at least the portion of the circular nucleic acid molecule. In some embodiments, the one or more sequencing variants indicate a mutation in a gene. In some embodiments, the at least one reference sequence comprises a consensus sequence of at least a portion of the gene.

In some embodiments, the circular nucleic acid molecule comprises a recognition sequence. In some embodiments, the reaction mixture further comprises a recognition moiety that associates with the recognition sequence to enrich for at least the circular nucleic acid molecule from a pool of random nucleic acid molecules in the composition based at least in part on the recognition sequence. In some embodiments, the recognition moiety comprises at least one oligonucleotide having complementarity to at least the recognition sequence. In some embodiments, the composition comprises a selected library of circular nucleic acid molecules, wherein each circular nucleic acid molecule of at least 5% of the library comprises the recognition sequence. In some embodiments, each circular nucleic acid molecule of at least 10%, 20%, 30%, 40%, 50%, 60%, 70%, 80%, 90%, or 95% of the selected library comprises the recognition sequence. In some embodiments, a probability of occurrence of the recognition sequence without any mismatch is at most once in every $1\times10^4$ base pairs. In some embodiments, the probability of occurrence of the recognition sequence without any mismatch is at most once in every $5 \times 10^4$, $7 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ base pairs. In some embodiments, the recognition sequence comprises at least 5 bases. In some embodiments, the recognition sequence comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases.

In some embodiments, the circular nucleic acid molecule is from or derived from a biological sample of a subject. In some embodiments, the biological sample comprises a cell-free biological sample of the subject. In some embodiments, the circular nucleic acid molecule is derived from a cell-free nucleic acid molecule from the cell-free biological sample. In some embodiments, the cell-free nucleic acid molecule comprises a circulating tumor nucleic acid molecule or an amniotic fluid nucleic acid molecule. In some embodiments, the biological sample comprises a tissue sample of the subject. In some embodiments, the circular nucleic acid molecule derived from a genomic nucleic acid molecule from the tissue sample. In some embodiments, the tissue sample is derived from the group consisting of: infected tissue, diseased tissue, malignant tissue, calcified tissue, healthy tissue, and a combination thereof. In some embodiments, the tissue sample is from the malignant tissue comprising a tumor, sarcoma, leukemia, or a derivative thereof.

In some embodiments, the circular nucleic acid molecule comprises DNA, complimentary DNA, a derivative thereof, or a combination thereof. In some embodiments, the circular nucleic acid molecule comprises RNA.

In a different aspect, the present disclosure provides a cell-free library of circular nucleic acid molecules, wherein each individual circular nucleic acid molecule of at least 5% of the library comprises (i) a target site and (ii) a nick at a known distance away from the target site.

In some embodiments, each individual circular nucleic acid molecule of at least 10%, 20%, 30%, 40%, 50%, 60%, 70%, 80%, 90%, or 95% of the library comprises (i) the target site and (ii) the nick at the known distance away from the target site. In some embodiments, the individual circular nucleic acid molecule further comprises a recognition sequence. In some embodiments, a probability of occurrence of the recognition sequence without any mismatch is at most once in every $1 \times 10^4$ base pairs. In some embodiments, the probability of occurrence of the recognition sequence without any mismatch is at most once in every $5 \times 10^4$, $7 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ base pairs. In some embodiments, the recognition sequence comprises at least 5 bases. In some embodiments, the recognition sequence comprises at least 6, 7, 8, 9, 10, 11, 12, 13, 14, 15, 16, 17, 18, 19, 20, 21, 22, 23, 24, 25, 26, 27, 28, 29, 30, 35, 40, 45, or 50 bases.

In some embodiments, (i) a first target site of a first individual nucleic acid molecule and (ii) a second target site of a second individual nucleic acid molecule are the same. In some embodiments, (i) a first known distance between a first nick and the first target site of the first individual nucleic acid molecule and (ii) a second known distance between a second nick and the second target site of the second individual nucleic acid molecule are the same. In some embodiments, (i) a first known distance between a first nick and the first target site of the first individual nucleic acid molecule and (ii) a second known distance between a second nick and the second target site of the second individual nucleic acid molecule are different.

In some embodiments, (i) a first target site of a first individual nucleic acid molecule and (ii) a second target site of a second individual nucleic acid molecule are different. In some embodiments, (i) a first known distance between a first nick and the first target site of the first individual nucleic acid molecule and (ii) a second known distance between a second nick and the second target site of the second individual nucleic acid molecule are the same. In some embodiments, (i) a first known distance between a first nick and the first target site of the first individual nucleic acid molecule and (ii) a second known distance between a second nick and the second target site of the second individual nucleic acid molecule are different.

In some embodiments, the nicking site is at no more than 100,000 nucleotides away from the target site. In some embodiments, the nicking site is at no more than 50,000, 10,000, 5,000, 1,000, 500, 400, 300, 200, 100, 90, 80, 70, 60, 50, 40, 30, 25, 20, 15, 10, or 5 nucleotides away from the target site.

In some embodiments, the target site comprises at most about 500,000 nucleotides. In some embodiments, the target site comprises at most about 100,000, 50,000, 10,000, 5,000, 1,000, 500, 400, 300, 200, 100, 50, 40, 30, 25, 20, 15, 10, 9, 8, 7, 6, 5, 4, 3, 2, or 1 nucleotide.

In some embodiments, at least a portion of the circular nucleic acid molecule has or is suspected of having one or more variants in comparison to at least one reference sequence. In some embodiments, the one or more sequencing variants indicate a mutation in a gene. In some embodiments, the at least one reference sequence comprises a consensus sequence of at least a portion of the gene.

In some embodiments, the circular nucleic acid molecule comprises a circular double-stranded nucleic acid molecule. In some embodiments, the nick is at a sense strand of the circular double-stranded nucleic acid molecule. In some embodiments, the nick is at an anti-sense strand of the circular double-stranded nucleic acid molecule.

In some embodiments, the circular nucleic acid molecules are from or derived from a biological sample of a subject. In some embodiments, the biological sample comprises a cell-free biological sample of the subject. In some embodiments, the circular nucleic acid molecules are from or derived from a cell-free nucleic acid molecule from the cell-free biological sample. In some embodiments, the cell-free nucleic acid molecule comprises a circulating tumor nucleic acid molecule or an amniotic fluid nucleic acid molecule. In some embodiments, the biological sample comprises a tissue sample of the subject. In some embodiments, the circular nucleic acid molecules are from or derived from a genomic nucleic acid molecule from the tissue sample. In some embodiments, the tissue sample is derived from the group consisting of: infected tissue, diseased tissue, malignant tissue, calcified tissue, healthy tissue, and a combination thereof. In some embodiments, the tissue sample is from the malignant tissue comprising a tumor, sarcoma, leukemia, or a derivative thereof.

In some embodiments, the circular nucleic acid molecule comprises DNA, complimentary DNA, a derivative thereof, or a combination thereof. In some embodiments, the circular nucleic acid molecule comprises RNA.

In a different aspect, the present disclosure provides a method for processing or analyzing a nucleic acid molecule, comprising: (a) providing the nucleic acid molecule adjacent to a nanopore, and bringing the nucleic acid molecule in contact with a nucleotide having a tag under conditions sufficient to incorporate the nucleotide into a nucleic acid strand that is complementary to at least a portion of the nucleic acid molecule, wherein upon incorporation of the nucleotide into the nucleic acid strand, at least a portion of the tag is disposed within the nanopore; (b) detecting one or more signals indicative of an impedance or impedance change in the nanopore when at least a portion of the tag is within the nanopore; and (c) using the one or more signals to identify the nucleotide incorporated into the nucleic acid strand.

In some embodiments, the one or more signals are current or voltage. In some embodiments, the method further comprises measuring an electrical current or change thereof when at least the portion of the tag is disposed within the nanopore. In some embodiments, the one or more signals are not tunneling current. In some embodiments, the current is not a Faradaic current. In some embodiments, the nanopore is part of an electrical circuit that comprises a tunneling junction. In some embodiments, the nanopore includes a plurality of electrodes, and wherein (c) comprises using the plurality of electrodes to detect the one or more signals.

In some embodiments, the nanopore comprises a protein nanopore or a solid state nanopore.

In some embodiments, the method further comprises, in (a), releasing the tag from the nucleotide upon incorporation of the nucleotide into the nucleic acid strand. In some embodiments, the nucleic acid molecule comprises a circular nucleic acid molecule. In some embodiments, the method further comprises, prior to (b), subjecting the nucleic acid molecule to rolling circle amplification (RCA) to generate the nucleic acid strand. In some embodiments, the circular nucleic acid molecule is a circular double-stranded nucleic acid molecule. In some embodiments, the incorporation is performed without use of an oligonucleotide primer. In some embodiments, the providing comprises coupling at least one enzyme that performs the incorporation to (i) at least a portion of the nanopore or (ii) a membrane having the nanopore. In some embodiments, the membrane is a lipid bilayer. In some embodiments, the membrane is a solid state membrane. In some embodiments, the coupling comprises conjugating the at least one enzyme to the nanopore or the membrane.

In a different aspect, the present disclosure provides a system for processing or analyzing a nucleic acid molecule, comprising: a nanopore configured to (i) receive at least a portion of a tag upon incorporation of a nucleotide comprising the tag into a nucleic acid strand, wherein the nucleic acid strand is complementary to at least a portion of the nucleic acid molecule and (ii) detect one or more signals indicative of an impedance or impedance change in the nanopore when the at least the portion of the tag is within the nanopore, wherein the one or more signals are usable to identify the nucleotide incorporated into the nucleic acid strand.

In some embodiments, the one or more signals are current or voltage. In some embodiments, the nanopore is configured to measure an electrical current or change thereof when at least the portion of the tag is disposed within the nanopore. In some embodiments, the one or more signals are not tunneling current. In some embodiments, the current is not a Faradaic current. In some embodiments, the nanopore is part of an electrical circuit that comprises a tunneling junction. In some embodiments, the nanopore includes a plurality of electrodes configured to detect the one or more signals.

In some embodiments, the nanopore comprises a protein nanopore or a solid state nanopore.

In some embodiments, the at least the portion of the tag is released from the nucleotide upon incorporation of the nucleotide into the nucleic acid strand. In some embodiments, the system further comprises at least one enzyme configured to perform the incorporation. In some embodiments, the at least one enzyme is coupled to (i) at least a portion of the nanopore or (ii) a membrane having the nanopore. In some embodiments, the at least one enzyme is conjugated to (i) at least a portion of the nanopore or (ii) a membrane having the nanopore.

In some embodiments, the membrane is a lipid bilayer. In some embodiments, the membrane is a solid state membrane. In some embodiments, the nanopore or the membrane is configured to bind to at least a portion of the at least one enzyme. In some embodiments, the at least one enzyme is configured to bind to at least a portion of the nanopore or at least a portion of the membrane.

In a different aspect, the present disclosure provides a method of sequencing a plurality of polynucleotides, comprising: circularizing individual polynucleotides to provide a plurality of circular polynucleotides; nicking one strand of the circular polynucleotides using a nicking enzyme to provide a nicking site on each of the circular polynucleotides; binding a polymerase to the nicking site; and sequencing the circular polynucleotides.

In some embodiments, the polynucleotides comprise double stranded polynucleotides. In some embodiments, the polynucleotides comprise single stranded polynucleotides, and the method comprises adding a primer sequence in an adaptor region of the single stranded polynucleotide.

In some embodiments of any one of the subject methods, the method further comprises, before circularizing individual polynucleotides, amplifying the plurality polynucleotides. In some embodiments of any one of the subject methods, the polynucleotides comprise DNA, cDNA, ctDNA, or a combination of any of the foregoing. In some embodiments of any one of the subject methods, the circularizing the plurality polynucleotides comprises reacting the plurality of polynucleotides with a ligase. In some embodiments of any one of the subject methods, the circular polynucleotide comprises a circular double stranded polynucleotide and nicking comprises nicking the inner strand of the circular double stranded polynucleotide. In some embodiments of any one of the subject methods, the circular polynucleotide comprises a circular double stranded polynucleotide and nicking comprises nicking the outer strand of the circular double stranded polynucleotide.

In some embodiments of any one of the subject methods, the nicking enzyme comprises a sgRNA-CRISPR Cas9n (Cas9 D10A) nickase complex. In some embodiments, the sgRNA comprises a nucleotide sequence complimentary to a target nucleotide sequence. In some embodiments of any one of the subject methods, the nicking enzyme comprises a Cas9n (Cas9 D10A) nickase.

In some embodiments of any one of the subject methods, the polymerase comprises a linker. In some embodiments, the method further comprises, after binding the polymerase comprising a linker to the nicking site, binding the linker to a nanopore. In some embodiments of any one of the subject methods, the polymerase comprises a linker and a protein nanopore bound to the linker.

In some embodiments of any one of the subject methods, the method further comprises, before circularizing the plurality of polynucleotides, cleaving the polynucleotides to provide targeted polynucleotide fragments. In some embodiments of any one of the subject methods, the cleaving comprises binding a biotinylated sgRNA-CRISPER Cas9n complex to the polynucleotides. In some embodiments, the biotinylated sgRNA comprises a nucleotide sequence complimentary to a target polynucleotide sequence. In some embodiments of any one of the subject methods, the method further comprises enriching the targeted polynucleotide fragments.

In some embodiments of any one of the subject methods, the polymerase exhibits strong strand displacement activity.

In some embodiments of any one of the subject methods, the sequencing comprises sequencing the circular polynucleotide more than one time while bound to the nanopore. In some embodiments of any one of the subject methods, the sequencing comprises forward sequencing and reverse sequencing. In some embodiments of any one of the subject methods, the polynucleotide comprises a double stranded polynucleotide and the non-nicked polynucleotide strand comprises a template for amplification and sequencing. In some embodiments of any one of the subject methods, the polynucleotide comprises genomic DNA, cDNA, cell-free DNA, ctDNA, or a combination thereof. In some embodiments of any one of the subject methods, the sequencing comprises rolling circle amplification and transcription. In some embodiments of any one of the subject methods, the sequencing comprises whole genome sequencing. In some embodiments of any one of the subject methods, the sequencing comprises targeted sequencing. In some embodiments of any one of the subject methods, the targeted sequencing comprises identifying a sequence variant.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 2A and 2B schematically illustrate example methods for generating a nick within a circular nucleic acid at a known distance away from a target site;

FIGS. 2C and 2D schematically illustrate example methods for isolating or enriching for a circular nucleic acid comprising a recognition site and a target site;

DETAILED DESCRIPTION

Figure 1A:
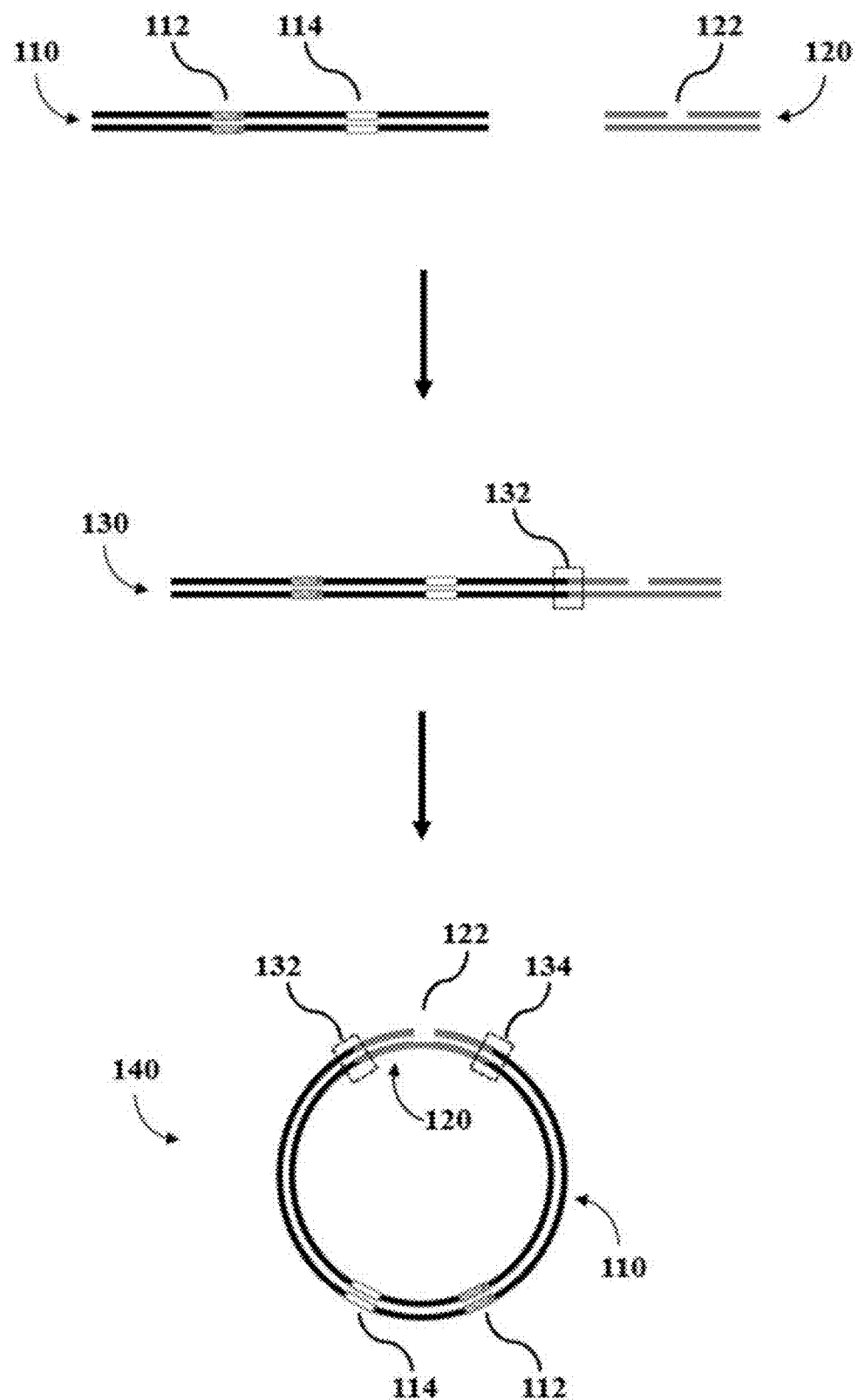
FIG. 1A schematically illustrates an example method for providing a circular nucleic acid with a nick.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular forms "a," "an," and "the" can include plural references unless the context clearly dictates otherwise. For example, the term "a transmembrane receptor" can include a plurality of transmembrane receptors.

The term "about" or "approximately," as used herein, can refer to within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "cell," as used herein, generally refers to a biological cell or cell derivative. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g. a cell can be a synthetically made, sometimes termed an artificial cell).

The terms "nucleotide," "nucleobase," and "base," as used interchangeably herein, generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP), uridine triphosphate (UTP), and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein generally refers to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N,N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif.; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

Naturally-occurring nucleotides guanine, cytosine, adenine, thymine, and uracil may be abbreviated as G, C, A, T, and U, respectively. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or a variant thereof) or a pyrimidine (i.e., C, T or U, or a variant thereof). A subunit can enable individual nucleic acid bases or groups of bases (e.g., AA, TA, AT, GC, CG, CT, TC, GT, TG, AC, CA, or uracil-counterparts thereof) to be resolved.

The terms "polynucleotide," "oligonucleotide," "oligomer," and "nucleic acid," as used interchangeably herein, generally refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g. altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, complementary DNA (cDNA, such as double-strand cDNA (dd-cDNA) or single-stranded cDNA (ss-cDNA)), circulating tumor DNA (ctDNA), damaged DNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes (e.g., fluorescence in situ hybridization (FISH) probes), and primers. The sequence of nucleotides can be interrupted by non-nucleotide components. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide can be further modified after polymerization, such as by conjugation with a labeling component.

The term "gene," as used herein, generally refers to a nucleic acid (e.g., DNA such as genomic DNA and cDNA) and its corresponding nucleotide sequence that is involved in encoding an RNA transcript. The term "gene" as used herein with reference to genomic DNA may include intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. The genes may not encode a polypeptide, for example, ribosomal RNA genes (rRNA) and transfer RNA (tRNA) genes. The term "gene" may not only include the transcribed sequences, but also non-transcribed regions including upstream and downstream regulatory regions, enhancers and promoters. A gene may be an "endogenous gene" or a native gene in its natural location in the genome of an organism. A gene may be an "exogenous gene" or a non-native gene. A non-native gene may be a gene not normally found in the host organism but which is introduced into the host organism by gene transfer (e.g., transgene). A non-native gene may be a naturally occurring nucleic acid or polypeptide sequence that comprises mutations, insertions and/or deletions (e.g., non-native sequence).

The term "mutation," as used herein, generally refers to a change in the sequence of nucleotides of a normally conserved nucleic acid sequence resulting in the formation of a mutant as differentiated from the normal (unaltered) or wild type sequence. A position (e.g., relative to a gene or a sample polynucleotide) and sequence of the mutation may be unknown prior to sequencing. Alternatively, a position (e.g., relative to a gene or a sample polynucleotide) and sequence of the mutation may be known prior to sequencing, in which case the sequencing may be performed to detect a presence of absence of the mutation in the sample polynucleotide. A mutation can comprise a base-pair substitution (e.g. single nucleotide substitution) and a frame-shift mutation. The frame-shift mutation may require insertion or deletion of one to several nucleotide pairs.

The term "probe," as used herein, generally refers to a nucleotide or polynucleotide that is tagged with a maker (e.g., a fluorescent marker) useful for detecting or identifying its corresponding target nucleotide or polynucleotide in a hybridization reaction by hybridization with a corresponding target sequence. The terms "nucleotide probe, "nucleotide tag," and "tagged nucleotide," as used interchangeable herein, generally refer to a probe having a single nucleotide. The terms "polynucleotide probe, "polynucleotide tag," and "tagged polynucleotide," as used interchangeable herein, generally refer to a probe having polynucleotide. A polynucleotide probe may be tagged with at least one marker (e.g., one marker per each nucleotide of the polynucleotide probe). A probe may be hybridizable to one or more target nucleotides or polynucleotides. A polynucleotide probe can be entirely complementary to one or more target polynucleotides in a sample, or contain one or more nucleotides that are not complementary (i.e., a mismatch) to one or more nucleotides of the one or more target polynucleotides in the sample.

The terms "complement," "complements," "complementary," and "complementarity," as used interchangeably herein, generally refer to a sequence that is fully complementary to and hybridizable to the given sequence. A sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. The respective lengths may comprise a region of at least 2, 3, 4, 5, 6, 7, 8, 9, 10, 11, 12, 13, 14, 15, 16, 17, 18, 19, 20, 21, 22, 23, 24, 25, 30, 35, 40, 45, 50, or more nucleotides.

Sequence identity, such as for the purpose of assessing percent complementarity, can be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment can be assessed using any suitable parameters of a chosen algorithm, including default parameters.

Complementarity can be perfect or substantial/sufficient. Perfect complementarity between two nucleic acids can mean that the two nucleic acids can form a duplex in which every base in the duplex is bonded to a complementary base by Watson-Crick pairing. Substantial or sufficient complementary can mean that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods The term "hybridization" as used herein, generally refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi-stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence may be referred to as the "complement" of the first sequence. The term "hybridizable," as applied to a polynucleotide, generally refers to the ability of the polynucleotide to form a complex that is stabilized via hydrogen bonding between the bases of the nucleotide residues in a hybridization reaction.

The term "target polynucleotide," as used herein, generally refers to a nucleic acid molecule or polynucleotide in a population of nucleic acid molecules having a target sequence. in which the presence, amount, and/or nucleotide sequence, or changes in one or more of these, are desired to be determined. The term "target sequence" generally refers to a nucleic acid sequence on a single strand of nucleic acid. The target sequence may be a portion of a gene, a regulatory sequence, genomic DNA, cDNA, ctDNA, RNA including mRNA, miRNA, rRNA, or others. The target sequence may be a target sequence from a sample or a secondary target such as a product of an amplification reaction. The target polynucleotide may be part of a gene (or a fragment thereof) that comprises one or more mutations.

The term "target site," as used herein, generally refers to a polynucleotide sequence that comprises the target polynucleotide (or a target nucleotide). The target polynucleotide (or target nucleotide) of the target site may be one or more sequence variants. Examples of the one or more sequence variants may include a single nucleotide variation, insertion or deletion of one or more nucleotides (e.g., sequential or non-sequential nucleotides), copy-number variation (CNV) comprising one or more repeats of one or more nucleotides (e.g., a CNV with a mean size of at least 1, 5, 10, 50, 100, 150, 200, or more kilobases (kb); a CNV with a mean size of at most 200, 150, 100, 50, 10, 5, 1, or fewer kb), and microsatellite instability (MSI). The target site may comprise at least 1, 2, 3, 4, 5, 6, 7, 8, 9, 10, 15, 20, 25, 30, 40, 50, 100, 200, 300, 400, 500, 1,000, 5,000, 10,000, 50,000, 100,000, 500,000, or more nucleotides. The target site may comprise at most 500,000, 100,000, 50,000, 10,000, 5,000, 1,000, 500, 400, 300, 200, 100, 50, 40, 30, 25, 20, 15, 10, 9, 8, 7, 6, 5, 4, 3, 2, or 1 nucleotide. The target site may comprise at least 1, 2, 3, 4, 5, 6, 7, 8, 9, 10, 15, 20, 25, 30, 40, 50, 100, 200, 300, 400, 500, 1,000, 5,000, 10,000, 50,000, 100,000, 500,000, or more nucleotides than the target polynucleotide. The target site may comprise at most 500,000, 100,000, 50,000, 10,000, 5,000, 1,000, 500, 400, 300, 200, 100, 50, 40, 30, 25, 20, 15, 10, 9, 8, 7, 6, 5, 4, 3, 2, or 1 nucleotide than the target polynucleotide. In some examples, the target site may be the target polynucleotide.

The term "stringent condition," as used herein, generally refers to one or more hybridization conditions under which a nucleic acid having complementarity to a target sequence predominantly hybridizes with a target sequence, and substantially does not hybridize to non-target sequences. Stringent conditions may be sequence-dependent, and may vary depending on a number of factors. In some cases, the longer the sequence, the higher the temperature at which the sequence may specifically hybridize to its target sequence.

The term "recognition moiety," as used herein, generally refers to a molecule (e.g., a small molecule, a polynucleotide, a protein, a variation thereof, or a combination thereof) that is capable of interacting with a nucleic acid sequence, i.e., a "recognition sequence" or "a recognition site," such as a desired (or target) nucleic acid sequence. The recognition moiety may comprise a domain (e.g., a component comprising the domain) capable of binding (e.g., hybridizing) to the recognition sequence. Such domain may comprise one or more amino acids, one or more nucleotides, a variation thereof, or a combination thereof. Alternatively or in addition to, the recognition moiety may associate with (e.g., bind to) a secondary molecule comprising such domain. In some examples, the recognition moiety may comprise a nucleic acid molecule capable of hybridizing to the recognition sequence. In some examples, the recognition moiety may comprise a component that exhibits a particular biological activity comprising, but are not limited to, one or more activities of a nuclease (e.g., double-stranded nuclease), nickase, transcriptional activator, transcriptional repressor, nucleic acid methylation enzyme, nucleic acid demethylation enzyme, and recombinase. The recognition sequence may comprise at least 3, 4, 5, 6, 7, 8, 9, 10, 11, 12, 13, 14, 15, 16, 17, 18, 19, 20, 21, 22, 23, 24, 25, 30, 35, 40, 45, 50, or more nucleotides. The recognition sequence may comprise at most 50, 45, 40, 35, 30, 25, 24, 23, 22, 21, 20, 19, 18, 17, 16, 15, 14, 13, 12, 11, 10, 9, 8, 7, 6, 5, 4, 3, or fewer nucleotides.

The recognition moiety may be used to isolate a desired molecule comprising the desired nucleic acid sequence from a plurality of molecules (e.g., a plurality of nucleic acid molecules). The recognition moiety may be used to enrich for a desired molecule comprising the desired nucleic in a composition or a reaction mixture. In some examples, the recognition moiety may be captured by a capturing system (e.g., magnetic beads) via one or more interactions (e.g., avidin-biotin binding, magnetic binding, etc.). In an example, the recognition moiety may comprise biotin, which may complex with a streptavidin magnetic bead for isolation or enrichment.

Examples of the recognition moiety can include CRISPR-associated (Cas) systems (e.g., Cas proteins, including catalytically active or inactive Cas polypeptides); zinc finger nucleases (ZFN); transcription activator-like effector nucleases (TALEN); meganucleases; RNA-binding proteins (RBP); Cas RNA binding proteins; recombinases; flippases; transposases; Argonaute (Ago) proteins (e.g., prokaryotic Argonaute (pAgo), archaeal Argonaute (aAgo), and eukaryotic Argonaute (eAgo)); a variant thereof; and a combination thereof. The recognition moiety may include a polynucleotide (e.g., at least 2, 3, 4, 5, 6, 7, 8, 9, 10, or more nucleotide-long sequence) that can be captured by a capturing system via one or more interactions, such as, for example, a polynucleotide sequence tagged with a biotin that can be captured by one or more avidin-functionalized magnetic beads. At least a portion of the polynucleotide may share complementarity to a recognition sequence of a target nucleic acid molecule.

The term "nickase," as used herein, generally refers to a molecule (e.g., an enzyme) that cleaves one strand of a double-stranded nucleic acid molecule (i.e., "nicks" a double-stranded molecule). The nickase may be a nuclease that cleaves only a single DNA strand, either due to its natural function or because it has been engineered (e.g., modified by mutation and/or deletion of one or more nucleotides) to cleave only a single DNA strand. The nickase may be a nicking enzyme (e.g., a restriction endonuclease, nicking endonuclease, etc.). The nickase may bind to a nicking site of a double-stranded nucleic acid molecule to create a nick (or a gap) in one strand of the double-stranded nucleic acid molecule. The nick may be generated within the nicking site. Alternatively, the nick may be generated adjacent to the nicking site. In some cases, the nickase may bind to a nickase binding site that is adjacent to the nicking site. The nick may be the length of at least 1, 2, 3, 4, 5, 6, 7, 8, 9, 10, or more nucleotides. The nick may be the length of at most 10, 9, 8, 7, 6, 5, 4, 3, 2, or 1 nucleotide. Examples of the nickase can include Cas systems (e.g., a Cas nickase, such as Cas9n), N.Alw I, Nb.BbvCI, Nt.BbvCI, Nb.BsmI, Nt.BsmAI, Nt.BspQ1, Nb.BsrDI, Nt.BstNBI, Nb.BstsCI, Nt.CviPII, Nb.Bpu 1 OI, Nt.Bpu 1 OI and Nt,Bst9I, variations thereof, and combinations thereof. In some examples, a nucleic acid molecule (e.g., a double-stranded nucleic acid molecule or a single-stranded nucleic acid molecule that is self-complementary) may comprise at least one nicking site that already includes at least one nick.

The terms "CRISPR-associated system," "Cas system," and "Cas complex," as used interchangeably herein, generally refer to a two component ribonucleoprotein complex with guide RNA (gRNA) and a Cas polypeptide or protein (e.g., a Cas endonuclease, a catalytic or a non-catalytic derivative thereof, etc.), or other protein having endonuclease activity. The term "CRISPR" refers to the Clustered Regularly Interspaced Short Palindromic Repeats and the related system thereof. At least a portion of the gRNA can have complementarity to at least a portion of the target region. The target region can comprise a "protospacer" and a "protospacer adjacent motif" (PAM), and both domains may be needed for a nuclease activity (e.g., cleavage) of the Cas polypeptide. The protospacer may be referred to as a target site (or a genomic target site). The gRNA may pair with (or hybridize) the opposite strand of the protospacer (binding site) to direct the Cas polypeptide to the target region. The PAM site generally refers to a short sequence recognized by the Cas polypeptide and, in some cases, can be required for the nuclease (or nickase) activity. The sequence and number of nucleotides for the PAM site can differ depending on the type of the Cas enzyme.

The Cas polypeptide may comprise a nuclease (or nickase) activity, and the gRNA may interact with the Cas polypeptide to direct the nuclease (or nickase) activity of the Cas polypeptide to a desired target region. Alternatively, the Cas polypeptide may be non-catalytic and may not comprise a nuclease activity. The non-catalytic Cas polypeptide may be referred to as a dead or inactive Cas (dCas).

A Cas protein may comprise a protein of or derived from a CRISPR-associated type I, type II, or type III system, which may have an RNA-guided polynucleotide-binding or nuclease activity. Examples of suitable Cas proteins include Cas3, Cas4, Cas5, Cas5e (or CasD), Cas6, Cas6e, Cas6f, Cas7, Cas8a1, Cas8a2, Cas8b, Cas8c, Cas9 (also known as Csn1 and Csx12), Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, homologues thereof, and modified versions (e.g., catalytic or non-catalytic) thereof. In some cases, a Cas protein may comprise a protein of or derived from a CRISPR-associated type V or type VI system, such as Cpf1 (or Cas12a), C2c1 (or Cas12b), C2c2, homologues thereof, and modified versions (e.g., catalytic or non-catalytic) thereof.

Although certain examples herein refer to a Cas protein, other proteins with endonuclease activity may be used. Such other proteins may not be Cas protein, but may be configured for use with a gRNA, for example.

The Cas polypeptide or protein may be engineered to modify the nuclease activity to a nickase activity. For example, an aspartate-to-alanine substitution (D10A) in the RuvC I catalytic domain of Cas9 from *S. pyogenes* can convert Cas9 from a nuclease that cleaves both strands to a Cas9n nickase that cleaves only a single strand. The Cas9n nickase mutants can introduce gRNA-targeted single-strand breaks in DNA instead of the double-strand breaks created by wild type Cas polypeptides. Other examples of mutations that render Cas9 a nickase can include H840A, N854A, and N863A.

The term "guide RNA (gRNA)," as used herein, generally refers to an RNA molecule that can bind to a Cas polypeptide and aid in targeting the Cas polypeptide to a specific location within a target nucleic acid region (e.g., a DNA or a gene). A degree of complementarity between a gRNA and the specific location within the target nucleic acid region can be at least 50%, 60%, 75%, 80%, 85%, 90%, 95%, 97.5%, 99%, or more. A guide RNA can comprise a CRISPR RNA (crRNA) segment and a trans-activating crRNA (tracrRNA) segment. The terms "crRNA" and "crRNA segment," as used interchangeably herein, generally refer to an RNA molecule or portion thereof that includes a polynucleotide-targeting guide sequence, a stem sequence, and, optionally, a 5'-overhang sequence. The terms "tracrRNA" and "tracrRNA segment," as used interchangeably herein, generally refer to an RNA molecule or portion thereof that includes a protein-binding segment (e.g., the protein-binding segment capable of interacting with a CRISPR-associated protein, such as a Cas9). In some cases, the guide RNA may be a single guide RNA (sgRNA), where the crRNA segment and the tracrRNA segment are located in the same RNA molecule. The gRNA may comprise one or more peptide nucleic acids.

The crRNA may comprise at least 15, 16, 17, 18, 19, 20, 21, 22, 23, 24, 25, 30, 35, 40, or more RNA bases. The crRNA may comprise at most 40, 35, 30, 25, 24, 23, 22, 21, 20, 19, 18, 17, 16, 15, or fewer RNA bases. The target nucleic acid sequence of the gRNA of the Cas system may comprise at least 15, 16, 17, 18, 19, 20, 21, 22, 23, 24, 25, 30, 35, 40, or more DNA bases. The target nucleic acid sequence of the gRNA of the Cas system may comprise at most 40, 35, 30, 25, 24, 23, 22, 21, 20, 19, 18, 17, 16, 15, or fewer DNA bases. The crRNA sequence can be selected to target any target sequence. A target sequence can be a sequence within a genome of a cell. A target sequence can include those that are unique in the target genome.

The term "polymerase," as used herein, generally refers to an enzyme (e.g., natural or synthetic) capable of catalyzing a polymerization reaction. Examples of polymerases can include a nucleic acid polymerase (e.g., a DNA polymerase or an RNA polyemrase), a transcriptase, and a liage. A polymerase can be a polymerization enzyme. The term "DNA polymerase" generally refers to an enzyme capable of catalyzing a polymerization reaction of DNA.

The term "linked polymerase," as used herein, generally refers to a polymerase such as a DNA polymerase that is coupled to (e.g., fused to) a linker. The linker may be capable of coupling to (e.g., binding or conjugating to) another entity (e.g., a nanopore, such as a protein nanopore or a solid state nanopore).

The terms "sequence variant" and "sequencing variant," as used interchangeably herein, generally refer to any variation in sequence relative to one or more reference sequences. Typically, a sequence variant occurs with a lower frequency than a reference sequence for a given population of individuals for whom the reference sequence is provided. For example, a particular bacterial genus may have a consensus reference sequence for the 16S rRNA gene, but individual species within that genus may have one or more sequence variants within the gene or a portion of a gene that are useful in identifying that species in a population of bacteria. As a further example, sequences for multiple individuals of the same species or multiple sequencing reads for the same individual may produce a consensus sequence when optimally aligned, and sequence variants with respect to that consensus may be used to identify mutants in the population indicative of dangerous contamination. In general, a "consensus sequence" refers to a nucleotide sequence that reflects the most common choice of base at each position in the sequence where the series of related nucleic acids has been subjected to intensive mathematical and/or sequence analysis, such as optimal sequence alignment according to any of a variety of sequence alignment algorithms. A reference sequence is a single known reference sequence, such as the genomic sequence of a single individual. A reference sequence can be a consensus sequence formed by aligning multiple known sequences, such as the genomic sequence of multiple individuals serving as a reference population, or multiple sequencing reads of polynucleotides from the same individual. A reference sequence can be a consensus sequence formed by optimally aligning the sequences from a sample under analysis, such that a sequence variant represents a variation relative to corresponding sequences in the same sample. A sequence variant can occur with a low frequency in the population (also referred to as a "rare" sequence variant). For example, a sequence variant may occur with a frequency of or less than 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. A sequence variant can occur with a frequency of or less than 0.1%.

A sequence variant can be any variation with respect to a reference sequence. A sequence variation may consist of a change in, insertion of, or deletion of a single nucleotide, or of a plurality of nucleotides such as, for example, 2, 3, 4, 5, 6, 7, 8, 9, 10, or more nucleotides. Where a sequence variant comprises two or more nucleotide differences, the nucleotides that are different may be contiguous with one another or discontinuous. Examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g., methylation differences).

The term "sequencing," as used herein, generally refers to a procedure for determining the order in which nucleotides occur in a target nucleotide sequence. Methods of sequencing can comprise high-throughput sequencing, such as, for example, next-generation sequencing (NGS). Sequencing may be, whole-genome sequencing or targeted sequencing. Sequencing may be single molecule sequencing or massively parallel sequencing. Next-generation sequencing methods can be useful in obtaining millions of sequences in a single run. In an example, sequencing may be performed using one or more nanopore sequencing methods, e.g., sequencing-by-synthesis, sequencing-by-ligation, or sequencing-by-cleavage.

The term "nanopore," as used herein, generally refers to a pore, channel, or passage formed or otherwise provided in a membrane. The membrane may be an organic membrane, such as a lipid bilayer, or a synthetic membrane, such as a membrane formed of a polymeric material such as a protein nanopore. The membrane may be a solid state membrane (e.g., silicon substrate). The nanopore may be disposed adjacent or in proximity to a sensing circuit or an electrode coupled to a sensing circuit, such as, for example, a complementary metal-oxide semiconductor (CMOS) or field effect transistor (FET) circuit. The nanopore may be part of the sensing circuit. A nanopore can have a characteristic width or diameter, for example, on the order of about 0.1 nanometer (nm) to 1000 nm. A nanopore can be a biological nanopore, solid state nanopore, hybrid biological-solid state nanopore, a variation thereof, or a combination thereof. Examples of the biological nanopore include, but are not limited to, OmpG from *E. coli*, sp., *Salmonella* sp., *Shigella* sp., and *Pseudomonas* sp., and alpha hemolysin (α-hemolysin) from *S. aureus* sp., MspA from *M. smegmatis* sp, a functional variant thereof, or a combination thereof. Sequencing may comprise forward sequencing and/or reverse sequencing. Examples of the solid state nanopore include, but are not limited to, silicon nitride, silicon oxide, graphene, molybdenum sulfide, a functional variant thereof, or a combination thereof. The solid state nanopore may be fabricated by high-energy beam manufacturing, imprinting (e.g., nanoimprinting), laser ablation, chemical etching, plasma etching (e.g., oxygen plasma etching), etc.

The term "nanopore sequencing complex," as used herein, generally refers to a nanopore linked or coupled to an enzyme, e.g., a polymerase, which in turn is associated with a polymer, e.g., a polynucleotide template. The nanopore sequencing complex may be positioned in a membrane, e.g., a lipid bilayer, where it functions to identify polymer components, e.g., nucleotides or amino acids.

The terms "nanopore sequencing" and "nanopore-based sequencing," as used interchangeably herein, generally refer to a method that determines the sequence of a polynucleotide with the aid of a nanopore. In some cases, the sequence of the polynucleotide may be determined in a template-dependent manner. In some cases, the methods, systems, or compositions disclosed herein may not be limited to any particular nanopore sequencing method, system, or device.

The term "barcode," as used herein, generally refers to a known nucleic acid sequence that allows some feature of a polynucleotide with which the barcode is associated to (e.g., a polynucleotide comprising at least a portion of the barcode or a polynucleotide having complementarity to at least a portion of the barcode) be identified. In some examples, the feature of the polynucleotide to be identified may be the sample from which the polynucleotide is derived. A barcode may be at least about 3, 4, 5, 6, 7, 8, 9, 10, 11, 12, 13, 14, 15, 16, 17, 18, 19, 20, or more nucleotides in length. A barcode may be at most 20, 19, 18, 17, 16, 15, 14, 13, 12, 11, 10, 9, 8, 7, 6, 5, 4, 3, or 2 nucleotides in length. A barcode associated with polynucleotides from a first sample may be different (e.g., different sequences and/or different lengths) than the barcode associated with polynucleotides from a second sample that is different than the first sample. In such a case, identification of the barcode in the respective polynucleotides may help identify the sample source of one or more of the polynucleotides. Thus, different samples with different barcodes can be analyzed (e.g., sequenced) together (e.g., in the batch), and separated during analysis based at least in part on the barcode. In some examples, a barcode may be identified accurately even after mutation, insertion, or deletion of one or more nucleotides in the barcode sequence (e.g., the mutation, insertion, or deletion of at least 1, 2, 3, 4, 5, 6, 7, 8, 9, 10, or more nucleotides). A plurality of polynucleotides from the same sample may have the same barcode. Alternatively, the plurality of polynucleotides from the same sample may have different barcodes. A first barcode may differ from a second barcode by at least three nucleotide positions, such as at least 3, 4, 5, 6, 7, 8, 9, 10, or more nucleotide positions. A plurality of barcodes may be represented in a pool of samples, each sample comprising polynucleotides comprising one or more barcodes that differ from the barcodes contained in the polynucleotides derived from the other samples in the pool. Samples of polynucleotides comprising one or more barcodes can be pooled based on the barcode sequences to which they are joined, such that all four of the nucleotide bases A, G, C, and T are approximately evenly represented at one or more positions along each barcode in the pool (such as at 1, 2, 3, 4, 5, 6, 7, 8, or more positions, or all positions of the barcode). In some examples, the methods of the invention may comprise identifying the sample from which a target polynucleotide is derived based on a barcode sequence to which the target polynucleotide is joined. The barcode may comprise a nucleic acid sequence that when joined to a target polynucleotide may serve as an identifier of the sample from which the target polynucleotide was derived. In an example, an oligonucleotide primer (e.g., an amplification primer) may comprise one or more barcodes. In another example, a nucleic acid molecule may be coupled (e.g., ligated) to an adaptor nucleic acid (e.g., for circularization), and the adaptor nucleic acid may comprise one or more barcodes.

The term "sample," as used herein, generally refers to any sample that may include one or more constituents (e.g., nucleic acid molecules) for processing or analysis. The sample may be a biological sample. The sample may be a cellular or tissue sample. The sample may be a cell-free sample, such as blood (e.g., whole blood), plasma, serum, sweat, saliva, or urine. The sample may be obtained in vivo or cultured in vitro.

The term "subject," as used herein, generally refers to an individual or entity from which a sample is derived, such as, for example, a vertebrate (e.g., a mammal, such as a human) or an invertebrate. A mammal may be a murine, simian, human, farm animal (e.g., cow, goat, pig, or chicken), or a pet (e.g., cat or dog). The subject may be a plant. The subject may be a patient. The subject may be asymptomatic with respect to a disease (e.g., cancer). Alternatively, the subject may be symptomatic with respect to the disease.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Overview

Currently available sequencing methods may be used to sequence one or more nucleic acids. Such methods, however, may be expensive and may not provide sequence information within a time period and at an accuracy range (or level) necessary to diagnose or treat a subject (e.g., an individual, a patient, etc.).

Large scale parallel nucleic acid sequencing may be useful in identifying one or more sequence variations within a population (e.g., a complex population). However, large scale parallel sequencing by currently available sequencing techniques may be limited by its error frequency, which may be larger than a frequency of the actual sequence variation(s) in the population. In an example, currently available high throughput sequencing methods may exhibit an error rate of about 0.1-1 percent (%). In some cases, detection of one or more sequence variants (e.g., one or more rare sequence variations) may be characterized by a high false positive rate when frequency of the sequence variant(s) is low, e.g., at or below the error rate.

Methods and Compositions for Sequencing

Adaptor Coupling for Sequencing

In an aspect, the present disclosure provides a method for processing or analyzing a double-stranded nucleic acid molecule. The method may comprise providing (i) the double-stranded nucleic acid molecule and (ii) a double-stranded adapter having a nicking site within a sense strand or an anti-sense strand of the double-stranded adapter. The method may comprise coupling the double-stranded adapter to the double-stranded nucleic acid molecule. The method may comprise circularizing the double-stranded nucleic acid molecule coupled to the double-stranded adapter to generate a circularized double-stranded nucleic acid molecule. The nicking site may comprise a nick prior to the coupling between the double-stranded adapter and the double-stranded nucleic acid molecule. The nick may be a break within a sense strand of the double-stranded adapter. Alternatively, the nick may be a break within an anti-sense strand of the double-stranded adapter.

A length of the double-stranded nucleic acid molecule may be at least 2, 3, 4, 5, 10, 50, 100, 500, 1,000, 5,000, 10,000, 50,000, 100,000, or more nucleotides long. The length of the double-stranded nucleic acid molecule may be at most 100,000, 50,000, 10,000, 5,000, 1,000, 500, 100, 50, 10, or fewer nucleotides long. A length of the double-stranded adaptor may be at least 3, 4, 5, 6, 7, 8, 9, 10, 11, 12, 13, 14, 15, 16, 17, 18, 19, 20, 25, 30, 35, 40, 45, 50, or more nucleotides long. The length of the double-stranded adaptor may be at most 50, 45, 40, 35, 30, 25, 20, 19, 18, 17, 16, 15, 14, 13, 12, 11, 10, 9, 8, 7, 6, 5, 4, 3, or fewer nucleotides long.

The double-stranded nucleic acid molecule and the double-stranded adapter may be heterologous to one another. The double-stranded nucleic acid molecule and the double-stranded adapter may be different portions of the same gene or different genes. One of the double-stranded nucleic acid molecule and the double-stranded adapter may be derived from one species, and the other of the double-stranded nucleic acid molecule and the double-stranded adapter may be from a different species. One of the double-stranded nucleic acid molecule and the double-stranded adapter may be natural, and the other of the double-stranded nucleic acid molecule and the double-stranded adapter may be synthetic (e.g., the double-stranded adaptor may be a synthetic molecule). Alternatively, both of the double-stranded nucleic acid molecule and the double-stranded adapter may be synthetic.

In an example, the double-stranded nucleic acid molecule may be a fragmented double-stranded nucleic acid molecule from a genomic sample of a subject (e.g., from a cell of a subject), and the double-stranded adapter may be a synthetic adaptor comprising the nicking site. In another example, the double-stranded nucleic acid molecule may be a cell-free double-stranded nucleic acid molecule from a cell-free biological sample (e.g., blood, plasma, urine, etc.) of a subject, and the double-stranded adapter may be a synthetic adaptor comprising the nicking site.

The double-stranded nucleic acid molecule and the double-stranded adapter may be provided in a cell-free composition. The cell-free composition may be substantially free of intact cells. The cell-free composition may comprise a cell lysate or extract. The cell lysate may comprise a fluid containing contents of one or more lysed cells. The cell lysate may be crude (i.e., unpurified) or at least partially purified (e.g., to remove cellular debris or particulate, such as damaged outer cell membranes). Methods of forming the cell lysate may comprise sonication, homogenization, enzymatic lysis using lysozyme, freezing, grinding, and high pressure lysis. Alternatively, the cell-free composition may be derived from a cell-free biological sample.

The coupling of the double-stranded adapter to the double-stranded nucleic acid molecule may be performed in a cell-free condition, or the circularizing the double-stranded nucleic acid molecule coupled to the double-stranded adapter to the circularized double-stranded nucleic acid molecule may be performed in a cell-free condition. The coupling of the double-stranded adapter to the double-stranded nucleic acid molecule may be performed in a cell-free condition, and the circularizing the double-stranded nucleic acid molecule coupled to the double-stranded adapter to the circularized double-stranded nucleic acid molecule may be performed in a cell-free condition. Alternatively, (i) the coupling of the double-stranded adapter to the double-stranded nucleic acid molecule may be performed, or (ii) the circularizing the double-stranded nucleic acid molecule coupled to the double-stranded adapter to the circularized double-stranded nucleic acid molecule may be performed in the presence of one or more cells. In an example, the one or more cells may be configured to express one or more enzymes capable of performing the process in (i) and/or (ii).

The coupling may comprises coupling the sense strand of the double-stranded adapter to a sense strand of the double-stranded nucleic acid molecule. Alternatively, the coupling may comprise coupling the anti-sense strand of the double-stranded adapter to an anti-sense strand of the double-stranded nucleic acid molecule. In a different alternatively, the coupling may comprises (i) coupling the sense strand of the double-stranded adapter to a sense strand of the double-stranded nucleic acid molecule, and (ii) coupling the anti-sense strand of the double-stranded adapter to an anti-sense strand of the double-stranded nucleic acid molecule. Coupling of two nucleic acid molecules may comprise ligation (e.g., by an enzyme, such as a ligase), hybridization (e.g., in the absence of an enzyme), or both.

The nicking site may be part of a sense strand of the circularized double-stranded nucleic acid molecule. The nicking site may be neither the 5' end nor the 3' end of the sense strand. The nicking site may be at least 1, 2, 3, 4, 5, 10, 15, 20, 25, 30, or more nucleotides away from the 5' end or the 3' end of the sense strand. The nicking site may be at most 30, 25, 20, 15, 10, 5, 4, 3, 2, or 1 nucleotide away from the 5' end or the 3' end of the sense strand. Alternatively or in addition to, the nicking site may be part of an anti-sense strand of the circularized double-stranded nucleic acid molecule. The nicking site may be neither the 5' end nor the 3' end of the anti-sense strand. The nicking site may be at least 1, 2, 3, 4, 5, 10, 15, 20, 25, 30, or more nucleotides away from the 5' end or the 3' end of the anti-sense strand. The nicking site may be at most 30, 25, 20, 15, 10, 5, 4, 3, 2, or 1 nucleotide away from the 5' end or the 3' end of the anti-sense strand.

The method may further comprise subjecting the double-stranded nucleic acid molecule to sequencing from the nicking site of the double-stranded adapter. The sequencing may be performed for whole-genome sequencing (or genome-wide sequencing) or targeted sequencing. The sequencing may comprise one or more NGS methods. The sequencing may comprise a nanopore-based sequencing. The nanopore may be a protein nanopore (e.g., α-hemolysin) or a solid state nanopore. Alternatively, the nanopore may be a hybrid nanopore comprising at least a portion of a protein nanopore (e.g., α-hemolysin) and at least a portion of a solid state nanopore. The nanopore-based sequencing may utilize at least one enzyme (e.g., a polymerase or a nuclease) to interact with at least the double-stranded nucleic acid molecule. The at least one enzyme may be coupled to the nanopore. The at least one enzyme maybe fused to, conjugated to, or bound to the protein nanopore or the membrane comprising the nanopore. The at least one enzyme may be conjugated to or bound to the solid state nanopore or the membrane comprising the solid state nanopore. In some examples, the at least one enzyme may have a binding moiety capable of binding to the nanopore (or the solid state nanopore) or the membrane.

The sequencing may comprise (i) subjecting the double-stranded nucleic acid molecule to an extension reaction from the nicking site of the double-stranded adapter to generate a growing strand having sequence complementarity to at least a portion of a strand of the double-stranded nucleic acid molecule, and (ii) obtaining sequence information of at least a portion of the growing strand. The strand of the double-stranded nucleic acid molecule may be its sense strand or its anti-sense strand. Thus, the growing strand may exhibit complementarity to at least a portion of the sense-strand or at least a portion of the anti-sense strand. Alternatively, the strand of the double-stranded nucleic acid molecule may be both sense strand and anti-sense strand. Thus, a first growing strand may exhibit complementarity to at least a portion of the sense-strand, and a second growing strand may exhibit complementarity to at least a portion of the anti-sense strand.

The extension reaction may comprise amplification of at least at portion of the double-stranded nucleic acid molecule (e.g., double-stranded nucleic acid molecule and at least a portion of the double-stranded adapter). The amplification may generate a plurality of copies (e.g., at least 1, 2, 3, 4, 5, 10, 15, 20, or more copies; at most 20, 15, 10, 5, 4, 3, 2, or 1 copy) of at least a portion of the sense strand and/or the anti-sense strand of the double-stranded nucleic acid molecule. In some examples, the double-stranded nucleic acid molecule may be part of a circular (or circularized) double-stranded nucleic acid molecule, and the extension reaction may be RCA. The RCA may generate a growing strand that comprises one or more copies (e.g., at least 1, 2, 3, 4, 5, 10, 15, 20, or more copies; at most 20, 15, 10, 5, 4, 3, 2, or 1 copy) of at least a portion of the sense strand or the anti-sense strand of the circular double-stranded nucleic acid molecule.

The obtaining the sequence information may comprise detecting the at least the portion of the growing strand. The extension reaction may comprise bringing the double-stranded nucleic acid molecule in contact with a nucleotide coupled to a tag under conditions sufficient to incorporate the nucleotide into the growing strand. In such a case, the obtaining the sequence information may comprise detecting the tag. In some cases, the method may further comprise releasing the tag from the nucleotide upon incorporation of the nucleotide into the growing strand, and detecting the released tag for sequencing.

The extension reaction may be performed with an oligonucleotide primer. Alternatively, the extension reaction may be performed without use of an oligonucleotide primer. The nick within the double-stranded adaptor may serve as a binding site for an enzyme (e.g., a polymerase) capable of performing the extension reaction, and thus any oligonucleotide primer may not be required.

Alternatively, sequencing may comprise (i) subjecting the double-stranded nucleic acid molecule to a cleavage reaction from the nicking site of the double-stranded adapter to cleave at least a portion of a strand of the double-stranded nucleic acid molecule, and (ii) obtaining sequence information of the at least the portion of the strand. The strand of the double-stranded nucleic acid molecule to be cleaved may be its sense strand or its anti-sense strand. Alternatively, the strand of the double-stranded nucleic acid molecule to be cleaved may be both the sense strand and the anti-sense strand. Afterwards, the obtaining the sequence information may comprise detecting the at least the portion of the strand.

At least a portion of the double-stranded nucleic acid molecule may have or may be suspected of having one or more sequencing variants (e.g., one or more mutations) in comparison to at least one reference sequence. Thus, the sequencing may be performed to identify a presence of the at least the portion of the double-stranded nucleic acid molecule. The one or more sequencing variants may indicate a mutation in a gene. The at least one reference sequence may comprise a consensus sequence of at least a portion of the gene. The consensus sequence and the double-stranded nucleic acid molecule may be derived from the same species or different species. The consensus sequence may be a representative sequence of a collection of a plurality of sequences of the gene obtained from a plurality of samples (e.g., at least 2, 3, 4, 5, 10, 15, 20, 30, 40, 50, or more samples; at most 50, 40, 30, 20, 15, 10, 4, 3, or 2 samples) of the same species. In an example, both the double-stranded nucleic acid molecule and the at least one reference sequence may be derived from a human sample, and the at least one reference sequence may be a consensus sequence of at least a portion of a human gene of interest, such as a portion of a gene known to be generally free of any mutation.

The method may comprise, prior to coupling the double-stranded adapter to the double-stranded nucleic acid molecule, amplifying the double-stranded nucleic acid molecule to generate a plurality of copies of the double-stranded nucleic acid molecule. The amplification may generate at least 1, 2, 3, 4, 5, 10, 15, 20, 30, 40, 50, 100, 150, 200, or more copies of the double-stranded nucleic acid molecule. The amplification may generate at most 200, 150, 100, 50, 40, 30, 20, 15, 10, 5, 4, 3, 2, or 1 copy of the double-stranded nucleic acid molecule. As such, the method may utilize a plurality of the double-stranded adapters, e.g., the same number or more than the number of the copies of the double-stranded nucleic acid molecule.

The double-stranded nucleic acid molecule may comprise a recognition sequence. The recognition sequence may be endogenous or exogenous to the double-stranded nucleic acid molecule. The recognition sequence may comprise at least one natural nucleotide, at least one synthetic nucleotide, or both. The recognition sequence may comprise at least 5, 6, 7, 8, 9, 10, 11, 12, 13, 14, 15, 16, 17, 18, 19, 20, 21, 22, 23, 24, 25, 30, 40, 50, 100, or more nucleotides. The recognition sequence may comprise at most 100, 50, 40, 30, 25, 24, 23, 22, 21, 20, 19, 18, 17, 16, 15, 14, 13, 12, 11, 10, 9, 8, 7, 6, 5, or fewer nucleotides. The method may further comprise enriching for the double-stranded nucleic acid molecule from a pool of random nucleic acid molecules based at least in part on the recognition sequence. The pool may comprise at least 2, 3, 4, 5, 10, 50, 100, 500, 1,000, 5,000, 10,000, 50,000, 100,000, 500,000, 1,000,000 or more random nucleic acid molecules. The pool may comprise at most 1,000,000, 500,000, 100,000, 50,000, 10,000, 5,000, 1,000, 500, 100, 50, 10, 5, 4, 3, or 2 random nucleic acid molecules. The enrichment may comprise isolating the double-stranded nucleic acid molecule (comprising the recognition sequence) from at least one different nucleic acid molecule that does not comprise the recognition sequence. The double-stranded nucleic acid molecule may be isolated from at least 1, 5, 10, 50, 100, 500, 1,000, 5,000, 10,000, 50,000, 100,000, 500,000, 1,000,000, or more different nucleic acid molecules that do not comprise the recognition sequence. The double-stranded nucleic acid molecule may be isolated from at most 1,000,000, 500,000, 100,000, 50,000, 10,000, 5,000, 1,000, 500, 100, 50, 10, 5, or 1 different nucleic acid molecule that does not comprise the recognition sequence.

The pool of random nucleic acid molecules, one of which being the double-stranded nucleic acid molecule comprising the recognition sequence, may be enriched for the double-stranded nucleic acid molecule prior to its amplification. Alternatively or in addition to, the pool of random nucleic acid molecules may be amplified prior to enriching for the double-stranded nucleic acid molecule.

The pool of random nucleic acid molecules, one of which being the double-stranded nucleic acid molecule comprising the recognition sequence, may be enriched for the double-stranded nucleic acid molecule prior to (i) coupling to at least the double-stranded adaptor and (ii) circularization. Alternatively, the pool of random nucleic acid molecules comprising the double-stranded nucleic acid molecule may be subjected to coupling to the double-stranded adaptor, and subsequently subjected to circularization. In a different alternative, the pool of random nucleic acid molecules comprising the double-stranded nucleic acid molecule may be subjected to (i) coupling to at least the double-stranded adaptor and (ii) circularization prior to the the enrichment for a circularized double-stranded nucleic acid molecule (and any excess linear double-stranded nucleic acid molecule thereof) that comprises the recognition sequence.

The enriching may comprise generating a selected library of double-stranded nucleic acid molecules (e.g., linear or circular). Each double-stranded nucleic acid molecule of at least 5%, 10%, 15%, 20%, 25%, 30%, 35%, 40%, 45%, 50%, 60%, 70%, 80%, 90%, 95%, or more of the selected library may comprise the at least the portion of the recognition sequence. Each double-stranded nucleic acid molecule of at most 100%, 95%, 90%, 80%, 70%, 60%, 50%, 45%, 40%, 35%, 30%, 25%, 20%, 15%, 10%, 5%, or less of the selected library may comprise the at least the portion of the recognition sequence.

The probability of occurrence of the recognition sequence without any mismatch may be at most once in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides. Alternatively, the probability of occurrence of the recognition sequence without any mismatch may be at most twice, three times, four times, five times, or more in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides.

The recognition sequence may comprise at least 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides. The recognition sequence may comprise at most 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, or fewer nucleotides.

The enriching may comprise (i) binding a recognition moiety having complementarity to the recognition sequence to the double-stranded nucleic acid molecule to form a recognition complex and (ii) extracting the recognition complex from a pool of random nucleic acid molecules. The recognition moiety may have at least 30%, 40%, 50%, 60%, 70%, 80%, 90%, 95%, or more complementarity to the recognition sequence. The recognition moiety may have at most 100%, 95%, 90%, 80%, 70%, 60%, 50%, 40%, 30%, or less complementarity to the recognition sequence.

A pool of random nucleic acid molecules may be enriched for one or more double-stranded nucleic acid molecules comprising the recognition sequence (i) prior to providing the one or more double-stranded nucleic acid molecules and one or more double-stranded adaptors having the nicking site, or (ii) subsequent to coupling at least one double-stranded adaptor to each of a plurality of double-stranded nucleic acid molecules from the pool. Alternatively, the pool of random nucleic acid molecules may be enriched for the one or more double-stranded nucleic acid molecules comprising the recognition sequence (i) prior to providing the one or more double-stranded nucleic acid molecules and one or more double-stranded adaptors having the nicking site, and (ii) subsequent to coupling at least one double-stranded adaptor to each of a plurality of double-stranded nucleic acid molecules from the pool.

Alternatively or in addition to, the double-stranded adaptor may comprise at least one recognition sequence. Subsequent to coupling (e.g., ligating) of the double-stranded adaptor to the double-stranded nucleic acid molecule, the at least one recognition sequence may be used (e.g., recognized by at least one recognition moiety provided herein) to enrich for the double-stranded nucleic acid molecule that is coupled to the double-stranded adaptor. The enrichment may deplete one or more double-stranded nucleic acid molecules that are not coupled to the double-stranded adaptor.

The recognition sequence of the double-stranded adaptor may comprise at least one natural nucleotide, at least one synthetic nucleotide, or both. The recognition sequence of the double-stranded adaptor may comprise at least 5, 6, 7, 8, 9, 10, 11, 12, 13, 14, 15, 16, 17, 18, 19, 20, 21, 22, 23, 24, 25, 30, 40, 50, 100, or more nucleotides. The recognition sequence of the double-stranded adaptor may comprise at most 100, 50, 40, 30, 25, 24, 23, 22, 21, 20, 19, 18, 17, 16, 15, 14, 13, 12, 11, 10, 9, 8, 7, 6, 5, or fewer nucleotides. The method may further comprise enriching for the double-stranded nucleic acid molecule that is coupled to the double-stranded adaptor from a pool of random nucleic acid molecules based at least in part on the recognition sequence of the double-stranded adaptor. The pool may comprise at least 2, 3, 4, 5, 10, 50, 100, 500, 1,000, 5,000, 10,000, 50,000, 100,000, 500,000, 1,000,000 or more random nucleic acid molecules. The pool may comprise at most 1,000,000, 500,000, 100,000, 50,000, 10,000, 5,000, 1,000, 500, 100, 50, 10, 5, 4, 3, or 2 random nucleic acid molecules. The enrichment may comprise isolating the double-stranded nucleic acid molecule (coupled to the double-stranded adaptor that comprises the recognition sequence) from at least one different nucleic acid molecule that does not comprise the recognition sequence. The double-stranded nucleic acid molecule may be isolated from at least 1, 5, 10, 50, 100, 500, 1,000, 5,000, 10,000, 50,000, 100,000, 500,000, 1,000,000, or more different nucleic acid molecules that do not comprise the recognition sequence. The double-stranded nucleic acid molecule may be isolated from at most 1,000,000, 500,000, 100,000, 50,000, 10,000, 5,000, 1,000, 500, 100, 50, 10, 5, or 1 different nucleic acid molecule that does not comprise the recognition sequence.

The double-stranded nucleic acid molecule may be from or derived from a biological sample of a subject. The biological sample may comprise a cell-free biological sample of the subject. The cell-free biological sample may be selected from the group consisting of: blood, plasma, serum, urine, perilymph fluid, feces, saliva, semen, amniotic fluid, cerebrospinal fluid, bile, sweat, tears, sputum, synovial fluid, vomit, and a combination thereof. The double-stranded nucleic acid molecule may be from or derived from a cell-free nucleic acid molecule from the cell-free biological sample. The cell-free nucleic acid molecule may comprise a circulating tumor nucleic acid molecule (e.g., ctDNA) or an amniotic fluid nucleic acid molecule.

The biological sample may comprise a tissue sample of the subject. The tissue sample may be derived from the group consisting of: bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye, brain, and a combination thereof. The double-stranded nucleic acid molecule may be from or derived from a genomic nucleic acid molecule from the tissue sample. The tissue sample may be derived from the group consisting of: infected tissue, diseased tissue, malignant tissue, calcified tissue, healthy tissue, and a combination thereof. The tissue sample may be from the malignant tissue comprising a tumor, sarcoma, leukemia, or a derivative thereof.

The double-stranded nucleic acid molecule may comprise DNA, cDNA, ctDNA, a derivative thereof, or a combination thereof. The double-stranded nucleic acid molecule comprises RNA.

In another aspect, the present disclosure provides a reaction mixture for processing or analyzing a double-stranded nucleic acid molecule. The reaction mixture may comprise a composition comprising (i) the double-stranded nucleic acid molecule and (ii) a double-stranded adapter having a nicking site within a sense strand or an anti-sense strand of the double-stranded adapter. The reaction mixture may comprise at least one enzyme that (i) couples the double-stranded adapter to the double-stranded nucleic acid molecule, or (ii) circularizes the double-stranded nucleic acid molecule coupled to the double-stranded adapter to generate a circularized double-stranded nucleic acid molecule. The nicking site may comprise a nick prior to the coupling between the double-stranded adapter and the double-stranded nucleic acid molecule. The nick may be break within a sense strand of the double-stranded adapter. Alternatively, the nick may be break within an anti-sense strand of the double-stranded adapter. The reaction mixture may be used or identified in any one of the subject methods for adaptor ligation, as provided in the present disclosure. The reaction mixture may be used to prepare one or more libraries (e.g., libraries of nucleic acid molecules, enzymes, or combinations thereof) or compositions for one or more sequencing methods. One or more components of the reaction mixture may be used simultaneously in the same reaction. In an example, the reaction may be performed in one reaction vial (e.g., a reaction tube), thereby reducing a purification step and/or sample loss, and/or sequencing with a small amount of nucleic acid sample input. One or more components of the reaction mixture may be used separately in different reactions.

The reaction mixture may comprise at least 1, 2, 3, 4, 5, 10, 50, 100, 500, 1,000, 5,000, 10,000, 50,000, 100,000, 500,000, 1,000,000, or more double-stranded nucleic acid molecules. The reaction mixture may comprise at most 1,000,000, 500,000, 100,000, 50,000, 10,000, 5,000, 1,000, 500, 100, 50, 10, 5, 4, 3, or 1 double-stranded nucleic acid molecules. The reaction mixture may comprise at least 1, 2, 3, 4, 5, 10, 50, 100, 500, 1,000, 5,000, 10,000, 50,000, 100,000, 500,000, 1,000,000, or more double-stranded adaptors. The reaction mixture may comprise at most 1,000,000, 500,000, 100,000, 50,000, 10,000, 5,000, 1,000, 500, 100, 50, 10, 5, 4, 3, or 1 double-stranded adaptor.

The at least one enzyme may be capable of (i) coupling the double-stranded adapter to the double-stranded nucleic acid molecule, and (ii) circularizing the double-stranded nucleic acid molecule coupled to the double-stranded adapter to generate the circularized double-stranded nucleic acid molecule. The reaction mixture may comprise at least 0.01, 0.1, 1, 10, 100, 1,000, 10,000, or more unit (e.g., Weiss unit or Modrich-Lehman unit) of the at least one enzyme. The reaction mixture may comprise at most 10,000, 1,000, 100, 10, 1, 0.1, 0.01, or less unit of the at least one enzyme. Alternatively, the reaction mixture may comprise (i) an enzyme that couples the double-stranded adapter to the double-stranded nucleic acid molecule, and (ii) an additional enzyme that circularizes the double-stranded nucleic acid molecule coupled to the double-stranded adapter to generate a circularized double-stranded nucleic acid molecule. The enzyme and the additional enzyme may be different. The reaction mixture may comprise at least 0.01, 0.1, 1, 10, 100, 1,000, 10,000, or more unit of the enzyme, and at least 0.01, 0.1, 1, 10, 100, 1,000, 10,000, or more unit of the additional enzyme. The reaction mixture may comprise at most 10,000, 1,000, 100, 10, 1, 0.1, 0.01, or less unit of the enzyme, and at most 10,000, 1,000, 100, 10, 1, 0.1, 0.01, or less unit of the additional enzyme.

The reaction mixture may be a cell-free reaction mixture. The cell-free reaction mixture may be substantially free of intact cells. The cell-free reaction mixture comprises a cell lysate or extract. The cell lysate may comprise a fluid containing contents of one or more lysed cells. The cell lysate may be crude (i.e., unpurified) or at least partially purified (e.g., to remove cellular debris or particulate, such as damaged outer cell membranes). The cell-free reaction mixture may be a product of sonication, homogenization, enzymatic lysis using lysozyme, freezing, grinding, and high pressure lysis of one or more cells. Alternatively, the cell-free reaction mixture may be derived from a cell-free biological sample.

The at least one enzyme may be capable of coupling (i) the sense strand of the double-stranded adapter to a sense strand of the double-stranded nucleic acid molecule, or (ii) the anti-sense strand of the double-stranded adapter to an anti-sense strand of the double-stranded nucleic acid molecule. The at least one enzyme may be capable of coupling (i) the sense strand of the double-stranded adapter to the sense strand of the double-stranded nucleic acid molecule and (ii) the anti-sense strand of the double-stranded adapter to the anti-sense strand of the double-stranded nucleic acid molecule. Alternatively, (i) a first enzyme may be capable of coupling the sense strand of the double-stranded adapter to a sense strand of the double-stranded nucleic acid molecule, and (ii) a second enzyme different than the first enzyme may be capable of coupling the anti-sense strand of the double-stranded adapter to an anti-sense strand of the double-stranded nucleic acid molecule. The at least one enzyme may comprise a ligase, a recombinase, a polymerase, a functional variant thereof, or a combination thereof. In some examples, the at least one enzyme may be capable of ligating the double-stranded adapter to the double-stranded nucleic acid molecule.

The reaction mixture may further comprise at least a second enzyme that performs an extension reaction to generate a growing strand having sequence complementarity to at least a portion of a strand of the double-stranded nucleic acid molecule. Prior to coupling of the double-stranded adapter to the double-stranded nucleic acid molecule, the at least the second enzyme may generate the growing strand. In some examples, the at least the second enzyme may generate a plurality of the growing strands to amplify the double-stranded nucleic acid molecule. Amplified copies of the double-stranded nucleic acid molecule may be used in the same reaction mixture. Alternatively, the amplified copies of the double-stranded nucleic acid molecule may be split into a plurality of reaction samples to be subjected under the same reaction condition or different reaction conditions. The at least the second enzyme may comprise a polymerase. The at least the second enzyme may comprise a polymerase and a recombinase, e.g., a recombinase polymerase amplification, which may be useful for a single tube, isothermal amplification alternative to a polymerase chain reaction (PCR) reaction amplification.

Subsequent to coupling of the double-stranded adapter to the double-stranded nucleic acid molecule, the at least the second enzyme may be capable of performing the extension reaction from the nicking site (or the nick of the nicking site) of the double-stranded adapter to generate the growing strand. The reaction mixture may further comprise at least one nucleotide coupled to a tag, wherein the at least the second enzyme incorporates the nucleotide into the growing strand. The tag may be a small molecule, nucleotide, polynucleotides, amino acid, polypeptide, polymers, metallic and/or ceramic particles, etc. In some examples, each of the nucleotides G, C, A, T, and U may comprise a different tag that is distinguishable from one another. In some examples, the tag may not be released from the nucleotide upon incorporation of the nucleotide into the growing strand. Alternatively, the at least the second enzyme may be capable of releasing the tag from the nucleotide upon incorporation of the nucleotide into the growing strand. The at least the second enzyme may perform the extension reaction with the help of at least one oligonucleotide primer. Alternatively, the at least the second enzyme may be capable of performing the extension reaction without use of an oligonucleotide primer. In an example, the extension reaction may comprise RCA, wherein the at least the second enzyme comprises a polymerase. The polymerase may bind to the nick of the nicking site for RCA.

The reaction mixture may further comprise at least a third enzyme that performs a cleavage reaction from the nicking site of the double-stranded adapter to cleave at least a portion of a strand of the double-stranded nucleic acid molecule. Starting from the nick of the nicking site, the at least the third enzyme may displace and cleave (i) at least a portion of the strand of the double-stranded adapter that comprises the nicking site and (ii) at least a portion of the strand of the double-stranded nucleic acid molecule coupled to the strand of the double-stranded adapter. The at least the third enzyme may comprise a nuclease (e.g., an endonuclease, such as a restriction endonuclease).

At least a portion of the double-stranded nucleic acid molecule may have or be suspected of having one or more variants in comparison to at least one reference sequence, as provided in the present disclosure. The reaction mixture may be used to prepare at least one composition for sequencing to identify a presence of the at least the portion of the double-stranded nucleic acid molecule.

The double-stranded nucleic acid molecule may comprise a recognition sequence, as provided in the present disclosure. The reaction mixture, thus, may further comprise a recognition moiety that associates with the recognition sequence to enrich for at least the double-stranded nucleic acid molecule from a pool of random nucleic acid molecules in the composition based at least in part on the recognition sequence. The recognition moiety may comprise at least one oligonucleotide (e.g., at least a portion of a gRNA for a variation of a Cas system) having complementarity to at least the recognition sequence. The oligonucleotide of the recognition moiety may have at least 30%, 40%, 50%, 60%, 70%, 80%, 90%, 95%, or more complementarity to the recognition sequence. The oligonucleotide of the recognition moiety may have at most 100%, 95%, 90%, 80%, 70%, 60%, 50%, 40%, 30%, or less complementarity to the recognition sequence.

The composition of the reaction mixture may comprise a selected library of double-stranded nucleic acid molecules (e.g., linear or circular). Each double-stranded nucleic acid molecule of at least 5%, 10%, 15%, 20%, 25%, 30%, 35%, 40%, 45%, 50%, 60%, 70%, 80%, 90%, 95%, or more of the selected library may comprise the at least the portion of the recognition sequence. Each double-stranded nucleic acid molecule of at most 100%, 95%, 90%, 80%, 70%, 60%, 50%, 45%, 40%, 35%, 30%, 25%, 20%, 15%, 10%, 5%, or less of the selected library may comprise the at least the portion of the recognition sequence.

The probability of occurrence of the recognition sequence without any mismatch may be at most once in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs). Alternatively, the probability of occurrence of the recognition sequence without any mismatch may be at most twice, three times, four times, five times, or more in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs).

The recognition sequence may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The recognition sequence may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

In a different aspect, the present disclosure provides a library of circularized double-stranded nucleic acid molecules. The library may comprise (i) a double-stranded nucleic acid domain that is coupled to (ii) a double-stranded adapter domain that comprises a nicking site within a sense strand or an anti-sense strand of the double-stranded adapter domain. Each circularized double-stranded nucleic acid molecule of at least 5% of the library may comprise a recognition sequence. The library of circularized double-stranded nucleic acid molecules may be a starting material or a product of any one of the subject methods or reaction mixtures provided in the present disclosure.

The nicking site may be present within the double-stranded adapter domain prior to coupling of the double-stranded adapter domain to the double-stranded nucleic acid domain. The nicking site may comprise a nick prior to the coupling between the double-stranded adapter and the double-stranded nucleic acid molecule.

The double-stranded nucleic acid domain and the double-stranded adapter domain may be heterologous to one another. Alternatively, the double-stranded nucleic acid domain and the double-stranded adapter domain may not be heterologous to one another. The library may be in a cell-free composition. Alternatively, the library may not be in a cell-free composition.

At least a portion of the circularized double-stranded nucleic acid domain in the library may have or be suspected of having one or more sequencing variants in comparison to at least one reference sequence. The one or more sequencing variants may indicate a mutation in a gene. The at least one reference sequence may comprise a consensus sequence of at least a portion of the gene.

Each circularized double-stranded nucleic acid molecule of at least 5%, 10%, 15%, 20%, 25%, 30%, 35%, 40%, 45%, 50%, 60%, 70%, 80%, 90%, 95%, or more of the selected library may comprise the at least the portion of the recognition sequence. Each circularized double-stranded nucleic acid molecule of at most 100%, 95%, 90%, 80%, 70%, 60%, 50%, 45%, 40%, 35%, 30%, 25%, 20%, 15%, 10%, 5%, or less of the selected library may comprise the at least the portion of the recognition sequence.

The probability of occurrence of the recognition sequence without any mismatch may be at most once in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs). Alternatively, the probability of occurrence of the recognition sequence without any mismatch may be at most twice, three times, four times, five times, or more in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs).

The recognition sequence may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The recognition sequence may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

The nicking site may be part of a sense strand of the circularized double-stranded nucleic acid molecule. Alternatively or in addition to, the nicking site may be part of an anti-sense strand of the circularized double-stranded nucleic acid molecule.

The circularized double-stranded nucleic acid molecule may be from or derived from a biological sample of a subject. The biological sample may comprise a cell-free biological sample of the subject. The circularized double-stranded nucleic acid molecule may be from or derived from a cell-free nucleic acid molecule from the cell-free biological sample. The cell-free nucleic acid molecule may comprise a circulating tumor nucleic acid (e.g., ctDNA) molecule or an amniotic fluid nucleic acid molecule. Alternatively, the biological sample may comprise a tissue sample of the subject. The circularized double-stranded nucleic acid molecule may be from or derived from a genomic nucleic acid molecule from the tissue sample. The tissue sample may be derived from the group consisting of: infected tissue, diseased tissue, malignant tissue, calcified tissue, healthy tissue, and a combination thereof. The tissue sample may be from the malignant tissue comprising a tumor, sarcoma, leukemia, or a derivative thereof.

The circularized double-stranded nucleic acid molecule may comprise DNA, cDNA, ctDNA, a derivative thereof, or a combination thereof. The circularized double-stranded nucleic acid molecule comprises RNA.

FIG. 1A schematically illustrates an example method for providing a circular nucleic acid with a nick. A first double-stranded nucleic acid molecule 110 and a second double-stranded nucleic acid molecule 120 may be provided. The nucleic acid molecule may be at least a portion of a biological sample or derived from a biological sample. The nucleic acid molecule 120 may be an adaptor (e.g., an adaptor for circularization, polymerization, nuclease activity, etc.). The first double-stranded nucleic acid molecule 110 may comprise a recognition sequence 112 and a target site 114. The target site 114 may have or be suspected of having one or more mutations compared to at least a reference sequence (e.g., a consensus sequence of a portion of a gene of a species or multiple species). The second double-stranded nucleic acid molecule 112 may comprise a nick 122 within the nucleic acid molecule 112. The nick 122 may not be positioned directly at either 5' or 3' ends of the (i) sense strand or (ii) anti-sense strand of the nucleic acid molecule 112. Alternatively, the nucleic acid molecule 112 may be characterized by having a removed phosphate group at either forward strand 5' end or reverse strand 5' end. In some examples, the nucleic acid molecule 112 with the phosphate group removed may be generated by DNA synthesis. In other examples, the nucleic acid molecule 112 with the phosphate group removed may be generated by PCR primers.

Referring to FIG. 1A, the first nucleic acid molecule 110 and the second nucleic acid molecule 120 may be coupled (e.g., via ligation and/or hybridization), to generate a coupled double-stranded nucleic acid molecule 130. The coupling may be performed at a constant temperature or at a plurality of temperatures (e.g., steps or gradient or temperatures). The coupling may be performed by one or more enzymes, e.g., a ligase and/or a recombinase. Subsequently, the nucleic acid molecule 130 may be circularized (e.g., via ligation and/or hybridization) to form a circular nucleic acid molecule 140. The circular nucleic acid molecule 140 may comprise at least a portion of the nucleic acid molecule 110 (e.g., the recognition sequence 112 and the target site 114), and at least a portion of the nucleic acid molecule 120 (e.g., the nick 122). The circular nucleic acid molecule 140 may be a template for sequencing (e.g., nanopore sequencing). In an example, information about the target site 114 of the circular nucleic acid molecule 140 may be obtained by nanopore sequencing using at least one enzyme (e.g., a polymerase or a nuclease), and the at least one enzyme may initiate its activity (e.g., extension reaction or cleavage) at the nick 122 of the circular nucleic acid molecule 140.

Figure 1B:
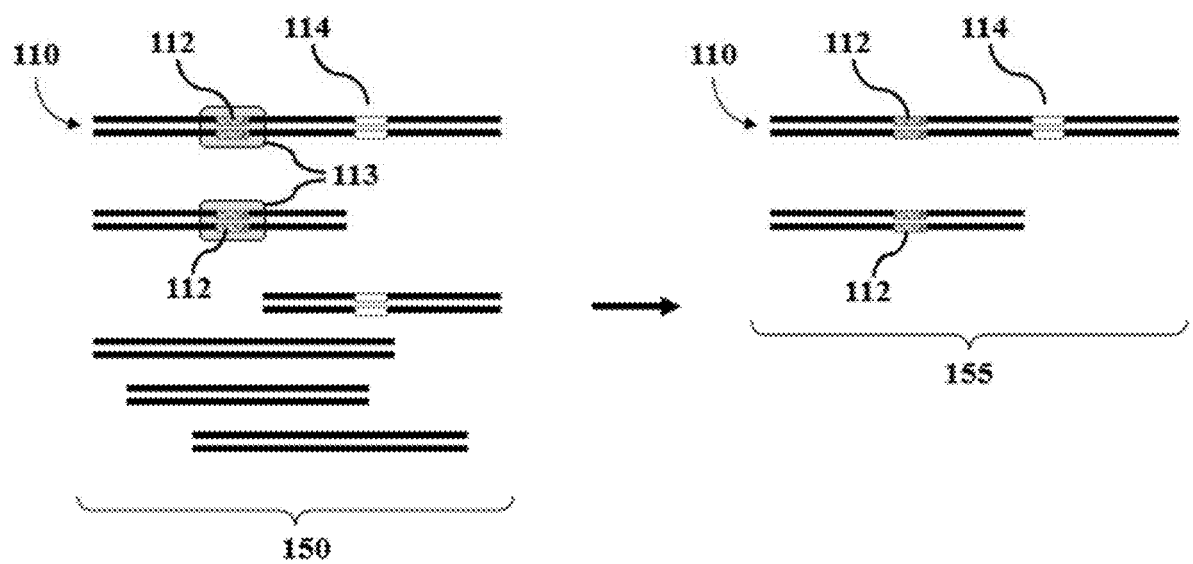
FIGS. 1B and 1C schematically illustrate example methods for isolating or enriching for a linear or circular nucleic acid comprising a recognition site.
Figure 1C:
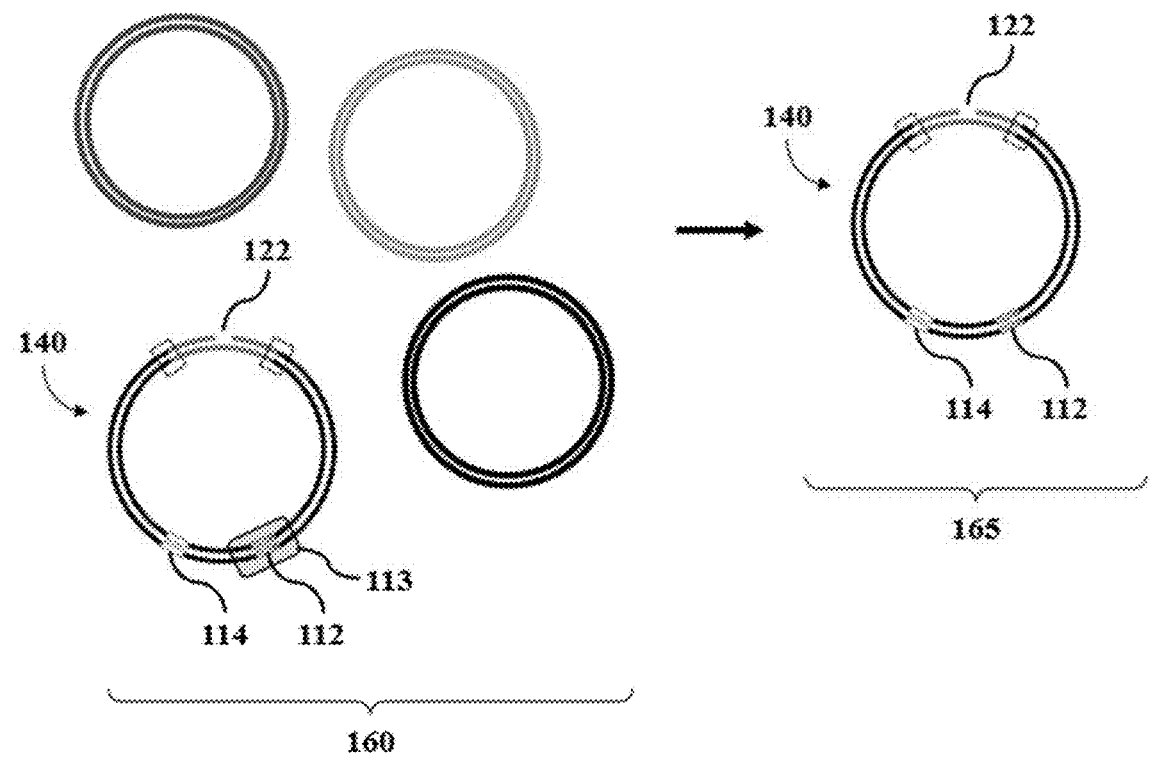

FIGS. 1B and 1C schematically illustrate example methods for isolating or enriching for a linear or circular nucleic acid comprising a recognition site. Referring to FIG. 1B, a pool of random nucleic acid molecules 150 may comprise the first double-stranded nucleic acid molecule 110 comprising the recognition site 112 and the target site 114. The pool 150 may also comprise a linear nucleic acid molecule comprising the recognition site 112, but not the target site 114. The pool 150 may further comprise linear nucleic acid molecules that do not comprise the recognition site 112. The pool 150 may be treated with at least one recognition moiety (e.g., dCas system) 113 to bind to the recognition site 112 and form a recognition complex at the recognition site 112. Any linear nucleic acid molecules comprising such recognition complex may be isolated from one or more nucleic acid molecules that do not comprise the recognition complex to generate a purified or enriched pool 155. In some examples, at least 5% of the nucleic acid molecules of the pool 155 may be characterized to have the recognition sequence 112. In additional examples, In some examples, at least a majority of the nucleic acid molecules of the pool 155 may be characterized to have the recognition sequence 112. The recognition moiety 113 may be removed (detached) from the recognition site 112 upon the purification or enrichment.

Referring to FIG. 1C, a pool of random circular nucleic acid molecules 160 may comprise the double-stranded nucleic acid molecule 140 comprising the recognition site 112 and the target site 114. The pool 160 may further comprise other circular nucleic acid molecules that do not comprise the recognition site 112. The pool 160 may be treated with at least one recognition moiety (e.g., dCas system) 113 to bind to the recognition site 112 and form a recognition complex at the recognition site 112. Any circular nucleic acid molecules comprising such recognition complex may be isolated from one or more circular nucleic acid molecules that do not comprise the recognition complex to generate a purified or enriched pool 165. In some examples, at least 5% (or a majority) of the circular nucleic acid molecules of the pool 165 may be characterized to have the recognition sequence 112. In some examples, at least a majority of the circular nucleic acid molecules of the pool 165 may be characterized to have the recognition sequence 112. The recognition moiety 113 may be removed (detached) from the recognition site 112 upon the purification or enrichment.

Figure 1D:
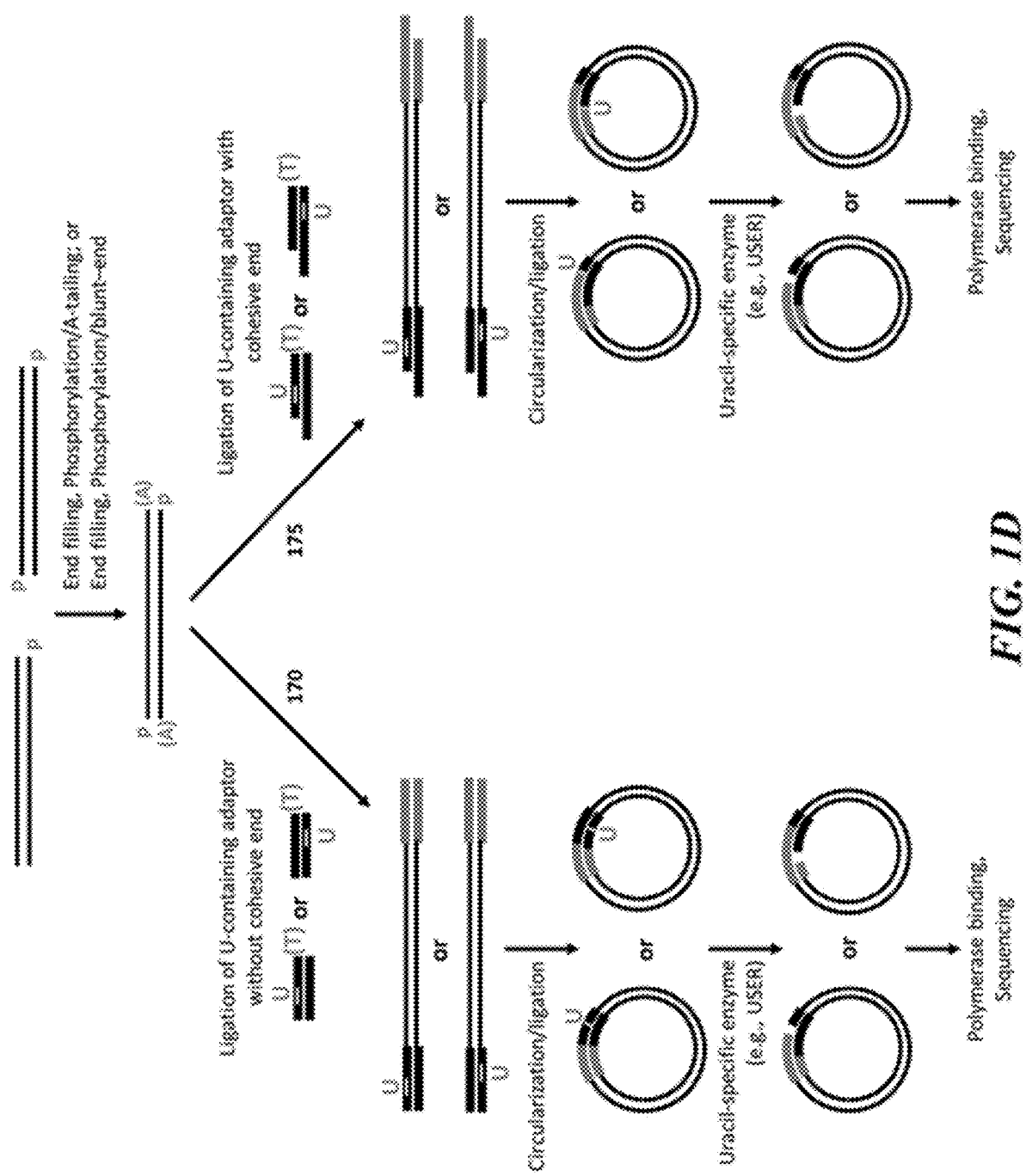
FIG. 1D schematically illustrates an example method for providing a circular nucleic acid comprising a nick at a specific location within the circular nucleic acid by using one or more uracil-specific enzymes.

FIG. 1D schematically illustrates an example method for providing a circular nucleic acid comprising a nick at a specific location within the circular nucleic acid by using one or more uracil-specific enzymes. A double-stranded nucleic acid molecule may be provided. The double-stranded nucleic acid molecule may be a fragmented or whole nucleic acid molecule from a biological sample. The double-stranded nucleic acid molecule may comprise two blunt ends. The double-stranded nucleic acid molecule may not comprise two blunt ends (e.g., only 1 or no blunt end). In such a case, end repair may be necessary, such that a repaired double-stranded nucleic acid molecule may (i) be free of overhangs, and (ii) contain 5' phosphate and 3' hydroxyl groups in the sense strand and the anti-send strand. Blunt ends may be obtained by end filing by one or more enzyme, e.g., restriction enzymes and/or exonucleases. The 5' phosphorylation may be achieved by one or more enzymes, e.g., a kinase such as a T4 Polynucleotide Kinase. Alternatively or in addition to, incorporation of a non-templated deoxyadenosine 5'-monophosphate (dAMP) onto the 3' end of a blunt end of the double-stranded nucleic acid molecule (i.e., dA-tailing) may be performed. The dA-tailing may prevent concatemer formation (e.g., during one or more ligation steps). The dA-tailing may enable the double-stranded nucleic acid molecule to be ligated to one or more adaptors comprising a complementary deoxythymidine monophosphate (dTMP or "dT")-overhang.

Referring to FIG. 1D, in process 170, the modified double-stranded nucleic acid molecule may be coupled to one or more adaptors. The adaptor may comprise one or more uracil (U) nucleotides (e.g., within one or more strands of the adaptor). The adaptor may comprise a dT overhang complementary to the dA tail of the modified double-stranded nucleic acid molecule. The coupling may comprise ligating (e.g., via a DNA ligase) the end of the modified double-stranded nucleic acid molecule comprising the dA tail to the end of the adaptor comprising the dT overhang. In this example, the modified double-stranded nucleic acid molecule may be conjugated to two adaptors, wherein a first adaptor comprises the one or more uracil residues and a second adaptor does not comprise any uracil residue. Subsequently, the free end of the first adaptor and the second adaptor may be coupled (e.g., ligated) to one another to generate a circular nucleic acid molecule comprising at least a portion of the original double-stranded nucleic acid molecule, at least a portion of the first adaptor comprising the one or more uracil residues, and at least a portion of the second adaptor. Following, the circular nucleic acid molecule may be treated with one or more uracil-specific enzymes (e.g., uracil-specific excision reagent or "USER") to generate a single nucleotide gap (i.e., nick) at the location of the uracil residue. The resulting circular nucleic acid molecule with a nick at the specific site may be analyzed for sequencing.

Referring to FIG. 1D, in process 175, the modified double-stranded nucleic acid molecule may be coupled to one or more adaptors. The adaptor may comprise one or more uracil (U) nucleotides (e.g., within one or more strands of the adaptor). The adaptor may comprise a dT overhang complementary to the dA tail of the modified double-stranded nucleic acid molecule. The adaptor may further comprise a cohesive end for hybridization. The coupling may comprise ligating (e.g., via a DNA ligase) the end of the modified double-stranded nucleic acid molecule comprising the dA tail to the end of the adaptor comprising the dT overhang. In this example, the modified double-stranded nucleic acid molecule may be conjugated to two adaptors, wherein a first adaptor comprises the one or more uracil residues and a second adaptor does not comprise any uracil residue. Both adaptors may comprise a free cohesive end after the coupling. Subsequently, the free ends of the first adaptor and the second adaptor may be coupled (e.g., via hybridization of the cohesive ends and ligation) to one another to generate a circular nucleic acid molecule comprising at least a portion of the original double-stranded nucleic acid molecule, at least a portion of the first adaptor comprising the one or more uracil residues, and at least a portion of the second adaptor. Following, the circular nucleic acid molecule may be treated with one or more uracil-specific enzymes (e.g., uracil-specific excision reagent) to generate a single nucleotide gap (i.e., nick) at the location of the uracil residue. The resulting circular nucleic acid molecule with a nick at the specific site may be analyzed for sequencing.

Additional examples of the uracil-specific enzymes may include, but are not limited to, uracil-dna glycosylase (UDG) and/or Afu uracil-dna glycosylase (Afu UDG), e.g., to cleave N-glycosidic bond of deoxyuridine and generate a nick for DNA polymerase to perform a DNA extension reaction. Alteranteively, UDG and/or Afu UDG may be in combination with one or more repair enzymes specific for apurinic/apyrimidinic sites, e.g., FPG, hOGG1, hNEIL1 etc.

Controlling Nick-to-Target Site Distance for Sequencing

In an aspect, the present disclosure provides a method for processing or analyzing a circular nucleic acid molecule. The method may comprise providing a cell-free composition comprising the circular nucleic acid molecule that comprises (i) a target region and (ii) a nicking site at a known distance away from the target region. The method may comprise generating a nick at the nicking site of the circular nucleic acid molecule. The target region may be a gene of interest. The target region may be a suspected mutation site or an additional site that is adjacent to a suspected mutation site. In an example, a suspected mutation site of a particular disease may be known, and sequences of the gene comprise that suspected mutation site may also be known. Thus, by assigning a nicking site to a particular region of the gene that is characterized by a low chance of mutation, the circular nucleic acid molecule that comprises (i) the target region and (ii) the nicking site at the known distance away from the target region.

During sequencing, positioning the nick at a known distance away from the target site may be advantageous in one or more ways, including, but are not limited to: (i) increasing a chance of amplifying the target site more than once during amplification (e.g., RCA), (ii) increasing a chance of amplifying the target site at least one prior to exhaustion of the activity of an enzyme (e.g., polymerase) responsible for the amplification, and (ii) decreasing sequencing error (e.g., enzymatic error due to enzymatic fatigue).

In some examples, a plurality of nickases (e.g., a plurality of different types of nickases or different variations of the same nickase, such as, for example, a Cas nickase with different gRNAs) may be prepared to bind to a plurality of nicking sites of the circular nucleic acid molecule. The plurality of nickases may be assessed for binding to the respective nicking site, any off-target binding, or a nicking activity. At least one nicking site from the plurality of nicking sites may be selected to yield low off-target binding and/or high nicking activity. Thus, by selecting the nicking site from the plurality of nicking sites, the distance between the nicking site and the target site may be known prior to processing or analyzing one or more additional circular nucleic acid molecules. The nicking site may be selected from at least 2, 3, 4, 5, 6, 7, 8, 9, 10, 15, 20, 30, 40, 50, 100, or more nicking sites of the circular nucleic acid molecule. The nicking site may be selected from at most 100, 50, 40, 30, 20, 15, 10, 9, 8, 7, 6, 5, 4, 3, or 2 nicking sites of the circular nucleic acid molecule.

The generation of the nick at the nicking site of the circular nucleic acid molecule may be performed in a cell-free condition. The cell-free condition may be substantially free of intact cells. The cell-free condition may include that of a cell lysate or extract. The cell lysate may comprise a fluid containing contents of one or more lysed cells. The cell lysate may be crude (i.e., unpurified) or at least partially purified (e.g., to remove cellular debris or particulate, such as damaged outer cell membranes). Methods of forming the cell lysate may comprise sonication, homogenization, enzymatic lysis using lysozyme, freezing, grinding, and high pressure lysis. Alternatively, the cell-free condition may include that of a cell-free biological sample. Alternatively, the generation of the nick at the nicking site of the circular nucleic acid molecule may be performed in the presence of one or more cells (e.g., live or dead).

The nicking site may be at no more than 100,000, 50,000, 10,000, 5,000, 1,000, 500, 400, 300, 200, 100, 90, 80, 70, 60, 50, 40, 30, 25, 20, 15, 10, 5, or fewer nucleotides away from the target site. The nicking site may be at least 5, 10, 15, 20, 25, 30, 40, 50, 60, 70, 80, 90, 100, 200, 300, 400, 500, 1,000, 5,000, 10,000, 50,000, 100,000, or more nucleotides away from the target site.

The circular nucleic acid molecule may comprise a circular double-stranded nucleic acid molecule. The nicking site may be part of a sense strand of the circular nucleic acid molecule. Alternatively or in addition to, the nicking site may be part of an anti-sense strand of the circular nucleic acid molecule. The method may further comprise determining the nicking site based at least in part on a positon of the target site relative to at least one reference sequence. The at least one reference sequence may comprise a consensus sequence of at least a portion of the gene. The nicking site may be endogenous to the circular nucleic acid molecule. Thus, the determination of the nicking site may comprise selecting an endogenous sequence of the circular nucleic acid molecule. Alternatively, the nicking site may be exogenous to the circular nucleic acid molecule. Thus, the determining may comprise inserting the exogenous nicking site to the circular nucleic acid molecule. In some examples, an endogenous sequence of the circular nucleic acid molecule may be selected, and subsequently the exogenous nicking site may be inserted within or adjacent to the endogenous sequence of the circular nucleic acid molecule. As such, the distance between the exogenous nicking site and the target site may be controlled or known.

The circular nucleic acid molecule may further comprise a nickase binding site specific for the nickase. In such a case, the method may further comprise providing a nickase to the circular nucleic acid molecule under conditions sufficient for the nickase to associate with the nickase binding site and generate the nick. The probability of occurrence of the nickase binding site without any mismatch may be at most once in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs). Alternatively, the probability of occurrence of the nickase binding site without any mismatch may be at most twice, three times, four times, five times, or more in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs).

The nickase binding site may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The nickase binding site may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

The nickase binding site may be endogenous to the circular nucleic acid molecule. In an example, a linear nucleic acid molecule comprising an endogenous nickase binding site may be circularized to form the circular nucleic acid molecule. Alternatively, the nickase binding site may be exogenous to the circular nucleic acid molecule. In such a case, the method may further comprise, prior to generating the nick, inserting the exogenous nickase binding site to the circular nucleic acid molecule or its starting material (e.g., a linear nucleic acid molecule). In some examples, the exogenous nickase binding site may be inserted to a linear nucleic acid molecule prior to its circularization into the circular nucleic acid molecule. The linear nucleic acid molecule may comprise at least one recognition site, as provided herein, and a recognition moiety (e.g., a catalytically active recognition moiety, such as Cas9) may be used to (i) bind to the recognition site, (ii) cleave the linear nucleic acid molecule at the recognition site, and (iii) assist in insertion of the exogenous nickase binding site to the linear nucleic acid molecule at or adjacent to the at least one recognition site (e.g., via a homology-directed repair). The method may further comprise circularizing the nucleic acid molecule subsequent to inserting the exogenous nickase binding site. In other examples, the method may further comprise circularizing the linear nucleic acid molecule into the circular nucleic acid molecule prior to inserting the exogenous nickase binding site to the circular nucleic acid molecule. Upon circularization, a recognition moiety (e.g., a catalytically active recognition moiety, such as Cas9) may be used to (i) bind to a recognition site of the circular nucleic acid molecule, (ii) cleave the circular nucleic acid molecule at the recognition site, and (iii) assist in insertion of the exogenous nickase binding site to the circular nucleic acid molecule at or adjacent to the at least one recognition site (e.g., via a homology-directed repair).

The nickase binding site may be at no more than 30, 25, 20, 19, 18, 17, 16, 15, 14, 13, 12, 11, 10, 9, 8, 7, 6, 5, 4, 3, 2, or 1 nucleotide away from the nicking site. The nickase binding site may be at least 1, 2, 3, 4, 5, 6, 7, 8, 9, 10, 11, 12, 13, 14, 15, 16, 17, 18, 19, 20, 25, 30, or more nucleotides away from the nicking site. In some examples, the nickase binding site may comprise the nicking site. In such a case, the nicking site may be within the nickase binding site.

The method may further comprise subjecting the circular (or circularized) nucleic acid molecule to sequencing from the nick of the circular nucleic acid molecule. The sequencing may be performed for whole-genome sequencing (or genome-wide sequencing) or targeted sequencing. The sequencing may comprise one or more NGS methods. The sequencing may comprise a nanopore-based sequencing. The nanopore may be a protein nanopore (e.g., α-hemolysin) or a solid state nanopore. Alternatively, the nanopore may be a hybrid nanopore comprising at least a portion of a protein nanopore (e.g., α-hemolysin) and at least a portion of a solid state nanopore. The nanopore-based sequencing may utilize at least one enzyme (e.g., a polymerase or a nuclease) to interact with at least the circular nucleic acid molecule. The at least one enzyme may be coupled to the nanopore. The at least one enzyme maybe fused to, conjugated to, or bound to the protein nanopore or the membrane comprising the nanopore. The at least one enzyme may be conjugated to or bound to the solid state nanopore or the membrane comprising the solid state nanopore. In some examples, the at least one enzyme may have a binding moiety capable of binding to the nanopore (or the solid state nanopore) or the membrane.

The sequencing may comprise subjecting the circular (or circularized) nucleic acid molecule to sequencing. The sequencing may comprise subjecting the circular nucleic acid molecule to an extension reaction beginning from the nick to generate a growing strand having sequence complementarity to at least a portion of a strand of the circular nucleic acid molecule. The method may further comprise obtaining sequence information of at least a portion of the growing strand. The obtaining the sequence information may comprise detecting the at least the portion of the growing strand. The extension reaction may comprise bringing the circular nucleic acid molecule in contact with a nucleotide coupled to a tag under conditions sufficient to incorporate the nucleotide into the growing strand. The obtaining the sequence information may comprise detecting at least a portion of the tag. The at least the portion of the tag may be linked to the growing strand when analyzed for sequencing. Alternatively, the method may further comprise releasing the tag from the nucleotide upon incorporation of the nucleotide into the growing strand, and detecting the released tag for sequencing.

The extension reaction may be performed with an oligonucleotide primer. Alternatively, the extension reaction may be performed without use of an oligonucleotide primer. The nick within the double-stranded adaptor may serve as a binding site for an enzyme (e.g., a polymerase) capable of performing the extension reaction (e.g., rolling circle amplification), and thus no oligonucleotide primer may be required.

Alternatively, the sequencing may comprise (i) subjecting the circular nucleic acid molecule to a cleavage reaction from the nick to cleave at least a portion of a strand of the double-stranded nucleic acid molecule, and (ii) obtaining sequence information of the at least the portion of the strand. The strand of the circular nucleic acid molecule may be its sense strand or its anti-sense strand. Thus, the growing strand may exhibit complementarity to at least a portion of the sense-strand or at least a portion of the anti-sense strand. Alternatively, the strand of the double-stranded nucleic acid molecule may be both sense strand and anti-sense strand. Thus, a first growing strand may exhibit complementarity to at least a portion of the sense-strand, and a second growing strand may exhibit complementarity to at least a portion of the anti-sense strand.

The extension reaction may comprise amplification of at least at portion of the circular nucleic acid molecule (e.g., at least a portion of the nicking site and at least a portion of the target site). The amplification (e.g., RCA) may generate a plurality of copies (e.g., at least 1, 2, 3, 4, 5, 10, 15, 20, or more copies; at most 20, 15, 10, 5, 4, 3, 2, or 1 copy) of at least a portion of the sense strand and/or the anti-sense strand of the circular nucleic acid molecule. Extension products based on the circular nucleic acid molecules will have a first domain complementary to the at least the portion of the nicking site and a second domain complementary to at least the portion of the target site, and a distance between the first domain and the second domain may be substantially the same as the known distance between the target site and the nicking site in the circular nucleic acid molecule. Afterwards, the obtaining the sequence information may comprise detecting the at least the portion of the strand.

At least a portion of the circular nucleic acid molecule may have or may be suspected of having one or more sequencing variants (e.g., one or more mutations) in comparison to at least one reference sequence. Thus, the sequencing may be performed to identify a presence of the at least the portion of the circular nucleic acid molecule. The one or more sequencing variants may indicate a mutation in a gene. The at least one reference sequence may comprise a consensus sequence of at least a portion of the gene. The consensus sequence and the double-stranded nucleic acid molecule may be derived from the same species or different species. The consensus sequence may be a representative sequence of a collection of a plurality of sequences of the gene obtained from a plurality of samples (e.g., at least 2, 3, 4, 5, 10, 15, 20, 30, 40, 50, or more samples; at most 50, 40, 30, 20, 15, 10, 4, 3, or 2 samples) of the same species. In an example, both the circular nucleic acid molecule and the at least one reference sequence may be derived from a human sample, and the at least one reference sequence may be a consensus sequence of at least a portion of a human gene of interest, such as a portion of a gene known to be generally free of any mutation.

The method may comprise circularizing at least a linear nucleic acid molecule to generate the circular nucleic acid molecule. In some cases, the method may further comprise amplifying the linear nucleic acid molecule to generate a plurality of copies of the linear nucleic acid molecule. The amplification may generate at least 1, 2, 3, 4, 5, 10, 15, 20, 30, 40, 50, 100, 150, 200, or more copies of the linear nucleic acid molecule. The amplification may generate at most 200, 150, 100, 50, 40, 30, 20, 15, 10, 5, 4, 3, 2, or 1 copy of the linear nucleic acid molecule. The method may further comprise circularizing one or more of the copies of the linear nucleic acid molecule to generate a plurality of the circular nucleic acid molecule. The circularizing may comprise self-ligation (e.g., via one or more ligases), ligation via adaptors, hybridization via adaptors, or a combination thereof.

Alternatively or in addition to, the method may comprise amplifying the circular nucleic acid molecule to generate a plurality of copies of the circular nucleic acid molecule. The amplification may generate at least 1, 2, 3, 4, 5, 10, 15, 20, 30, 40, 50, 100, 150, 200, or more copies of the circular nucleic acid molecule. The amplification may generate at most 200, 150, 100, 50, 40, 30, 20, 15, 10, 5, 4, 3, 2, or 1 copy of the circular nucleic acid molecule.

The circular nucleic acid molecule may comprise a recognition sequence. The recognition sequence may be endogenous or exogenous to the circular nucleic acid molecule. The recognition sequence may comprise at least one natural nucleotide, at least one synthetic nucleotide, or both. The recognition sequence may comprise at least 5, 6, 7, 8, 9, 10, 11, 12, 13, 14, 15, 16, 17, 18, 19, 20, 21, 22, 23, 24, 25, 30, 40, 50, 100, or more nucleotides. The recognition sequence may comprise at most 100, 50, 40, 30, 25, 24, 23, 22, 21, 20, 19, 18, 17, 16, 15, 14, 13, 12, 11, 10, 9, 8, 7, 6, 5, or fewer nucleotides. The method may further comprise enriching for the circular nucleic acid molecule from a pool of random nucleic acid molecules based at least in part on the recognition sequence. The pool may comprise at least 2, 3, 4, 5, 10, 50, 100, 500, 1,000, 5,000, 10,000, 50,000, 100,000, 500,000, 1,000,000 or more random nucleic acid molecules. The pool may comprise at most 1,000,000, 500,000, 100,000, 50,000, 10,000, 5,000, 1,000, 500, 100, 50, 10, 5, 4, 3, or 2 random nucleic acid molecules. The enrichment may comprise isolating the circular nucleic acid molecule (comprising the recognition sequence) from at least one different nucleic acid molecule that does not comprise the recognition sequence. The circular nucleic acid molecule may be isolated from at least 1, 5, 10, 50, 100, 500, 1,000, 5,000, 10,000, 50,000, 100,000, 500,000, 1,000,000, or more different nucleic acid molecules that do not comprise the recognition sequence. The circular nucleic acid molecule may be isolated from at most 1,000,000, 500,000, 100,000, 50,000, 10,000, 5,000, 1,000, 500, 100, 50, 10, 5, or 1 different nucleic acid molecule that does not comprise the recognition sequence.

The pool of random nucleic acid molecules, one of which being the linear nucleic acid molecule comprising the recognition sequence, may be enriched for the linear nucleic acid molecule comprising the recognition sequence prior to its amplification. Alternatively or in addition to, the pool of random nucleic acid molecules may be amplified prior to enriching for the linear nucleic acid molecule comprising the recognition sequence. Alternatively or in addition to, the pool of random nucleic acid molecules, one of which being the circular nucleic acid molecule comprising the recognition sequence, may be enriched for the circular nucleic acid molecule prior to its amplification. Alternatively or in addition to, the pool of random nucleic acid molecules may be amplified prior to enriching for the circular nucleic acid molecule.

The enriching may comprise generating a selected library of circular nucleic acid molecules. Each circular nucleic acid molecule of at least 5%, 10%, 15%, 20%, 25%, 30%, 35%, 40%, 45%, 50%, 60%, 70%, 80%, 90%, 95%, or more of the selected library may comprise the at least the portion of the recognition sequence. Each circular nucleic acid molecule of at most 100%, 95%, 90%, 80%, 70%, 60%, 50%, 45%, 40%, 35%, 30%, 25%, 20%, 15%, 10%, 5%, or less of the selected library may comprise the at least the portion of the recognition sequence.

The probability of occurrence of the recognition sequence without any mismatch may be at most once in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs). Alternatively, the probability of occurrence of the recognition sequence without any mismatch may be at most twice, three times, four times, five times, or more in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs).

The recognition sequence may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The recognition sequence may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

The enriching may comprise (i) binding a recognition moiety having complementarity to the recognition sequence to the circular nucleic acid molecule to form a recognition complex and (ii) extracting the recognition complex from a pool of random nucleic acid molecules. The recognition moiety may have at least 30%, 40%, 50%, 60%, 70%, 80%, 90%, 95%, or more complementarity to the recognition sequence. The recognition moiety may have at most 100%, 95%, 90%, 80%, 70%, 60%, 50%, 40%, 30%, or less complementarity to the recognition sequence.

A pool of random nucleic acid molecules may be enriched for one or more circular nucleic acid molecules comprising the recognition sequence (i) prior to providing the cell-free composition comprising the circular nucleic acid molecule that comprises the target region and the nicking site at the known distance away from the target region, or (ii) subsequent to generating the nick at the nicking site of the circular nucleic acid molecule. Alternatively, the pool of random nucleic acid molecules may be enriched for one or more circular nucleic acid molecules comprising the recognition sequence (i) prior to providing the cell-free composition comprising the circular nucleic acid molecule that comprises the target region and the nicking site at the known distance away from the target region, and (ii) subsequent to generating the nick at the nicking site of the circular nucleic acid molecule.

The circular nucleic acid molecule may be from or derived from a biological sample of a subject. The biological sample may comprise a cell-free biological sample of the subject. The cell-free biological sample may be selected from the group consisting of: blood, plasma, serum, urine, perilymph fluid, feces, saliva, semen, amniotic fluid, cerebrospinal fluid, bile, sweat, tears, sputum, synovial fluid, vomit, and a combination thereof. The circular nucleic acid molecule may be from or derived from a cell-free nucleic acid molecule from the cell-free biological sample. The cell-free nucleic acid molecule may comprise a circulating tumor nucleic acid molecule (e.g., ctDNA) or an amniotic fluid nucleic acid molecule.

The biological sample may comprise a tissue sample of the subject. The tissue sample may be derived from the group consisting of: bone, heart, thymus, artery, blood vessel, lung, muscle, stomach, intestine, liver, pancreas, spleen, kidney, gall bladder, thyroid gland, adrenal gland, mammary gland, ovary, prostate gland, testicle, skin, adipose, eye, brain, and a combination thereof. The circular nucleic acid molecule may be from or derived from a genomic nucleic acid molecule from the tissue sample. The tissue sample may be derived from the group consisting of: infected tissue, diseased tissue, malignant tissue, calcified tissue, healthy tissue, and a combination thereof. The tissue sample may be from the malignant tissue comprising a tumor, sarcoma, leukemia, or a derivative thereof.

The circular nucleic acid molecule may comprise DNA, cDNA, ctDNA, a derivative thereof, or a combination thereof. The circular nucleic acid molecule comprises RNA.

In another aspect, the present disclosure provides a reaction mixture for processing or analyzing a circular nucleic acid molecule. The reaction mixture may comprise a cell-free composition comprising the circular nucleic acid molecule. The circular nucleic acid molecule may comprise (i) a target site and (ii) a nicking site at a known distance away from the target site. The reaction mixture may comprise at least one enzyme that generates a nick at the nicking site of the circular nucleic acid molecule. The at least one enzyme may comprise a nuclease (e.g., restriction endonuclease) or a nickase (e.g., Cas9n nickase). The at least one enzyme may comprise a nuclease and a nickase. The reaction mixture may be used or identified in any one of the subject methods for sequencing with a known nick-to-target site distance, as provided in the present disclosure. The reaction mixture may be used to prepare one or more libraries (e.g., libraries of nucleic acid molecules, enzymes, or combinations thereof) or compositions for one or more sequencing methods. One or more components of the reaction mixture may be used simultaneously in the same reaction. In an example, the reaction may be performed in one reaction vial (e.g., a reaction tube), thereby reducing a purification step and/or sample loss, and/or sequencing with a small amount of nucleic acid sample input. One or more components of the reaction mixture may be used separately in different reactions. The reaction mixture may be a cell-free reaction mixture. Alternatively, the reaction mixture may not be a cell-free reaction mixture.

The nicking site may be at no more than 100,000, 50,000, 10,000, 5,000, 1,000, 500, 400, 300, 200, 100, 90, 80, 70, 60, 50, 40, 30, 25, 20, 15, 10, 5, or fewer nucleotides away from the target site. The nicking site may be at least 5, 10, 15, 20, 25, 30, 40, 50, 60, 70, 80, 90, 100, 200, 300, 400, 500, 1,000, 5,000, 10,000, 50,000, 100,000, or more nucleotides away from the target site.

The circular nucleic acid molecule may comprise a circular double-stranded nucleic acid molecule. The nicking site may be part of a sense strand of the circular nucleic acid molecule. Alternatively or in addition to, the nicking site may be part of an anti-sense strand of the circular nucleic acid molecule. The method may further comprise determining the nicking site based at least in part on a positon of the target site relative to at least one reference sequence. The at least one reference sequence may comprise a consensus sequence of at least a portion of the gene. The nicking site may be endogenous to the circular nucleic acid molecule. Thus, the determination of the nicking site may comprise selecting an endogenous sequence of the circular nucleic acid molecule. Alternatively, the nicking site may be exogenous to the circular nucleic acid molecule. Thus, the determining may comprise inserting the exogenous nicking site to the circular nucleic acid molecule. In some examples, an endogenous sequence of the circular nucleic acid molecule may be selected, and subsequently the exogenous nicking site may be inserted within or adjacent to the endogenous sequence of the circular nucleic acid molecule. As such, the distance between the exogenous nicking site and the target site may be controlled or known.

The nucleic acid molecule may further comprise an enzyme binding site specific for the at least one enzyme. The at least one enzyme may comprise In some examples, the at least one enzyme may exhibit an activity of a nickase, and the enzyme binding site may be the same as the nickase binding site, as provided in the present disclosure.

The probability of occurrence of the enzyme binding site without any mismatch may be at most once in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs). Alternatively, the probability of occurrence of the enzyme binding site without any mismatch may be at most twice, three times, four times, five times, or more in every $1\times10^4$, $5\times10^4$, $7\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$, $5\times10^{11}$, $1\times10^{12}$, $5\times10^{12}$, or more nucleotides (or base pairs).

The enzyme binding site may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The enzyme binding site may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

The enzyme binding site may be endogenous to the circular nucleic acid molecule. In an example, a linear nucleic acid molecule comprising an endogenous enzyme binding site may be circularized to form the circular nucleic acid molecule. Alternatively, the enzyme binding site may be exogenous to the circular nucleic acid molecule. In such a case, the method may further comprise, prior to generating the nick, inserting the exogenous enzyme binding site to the circular nucleic acid molecule or its starting material (e.g., a linear nucleic acid molecule). In some examples, the exogenous enzyme binding site may be inserted to a linear nucleic acid molecule prior to its circularization into the circular nucleic acid molecule. The linear nucleic acid molecule may comprise at least one recognition site, as provided herein, and a recognition moiety (e.g., a catalytically active recognition moiety, such as Cas9) may be used to (i) bind to the recognition site, (ii) cleave the linear nucleic acid molecule at the recognition site, and (iii) assist in insertion of the exogenous enzyme binding site to the linear nucleic acid molecule at or adjacent to the at least one recognition site (e.g., via a homology-directed repair). The method may further comprise circularizing the linear nucleic acid molecule subsequent to inserting the exogenous enzyme binding site. In other examples, the method may further comprise circularizing the linear nucleic acid molecule into the circular nucleic acid molecule prior to inserting the enzyme nickase binding site to the circular nucleic acid molecule. Upon circularization, a recognition moiety (e.g., a catalytically active recognition moiety, such as Cas9) may be used to (i) bind to a recognition site of the circular nucleic acid molecule, (ii) cleave the circular nucleic acid molecule at the recognition site, and (iii) assist in insertion of the exogenous enzyme binding site to the circular nucleic acid molecule at or adjacent to the at least one recognition site (e.g., via a homology-directed repair).

The enzyme binding site may be at no more than 30, 25, 20, 19, 18, 17, 16, 15, 14, 13, 12, 11, 10, 9, 8, 7, 6, 5, 4, 3, 2, or 1 nucleotide away from the nicking site. The enzyme binding site may be at least 1, 2, 3, 4, 5, 6, 7, 8, 9, 10, 11, 12, 13, 14, 15, 16, 17, 18, 19, 20, 25, 30, or more nucleotides away from the nicking site. In some examples, the enzyme binding site may comprise the nicking site. In such a case, the nicking site may be within the enzyme binding site.

The reaction mixture may further comprise at least a second enzyme that performs an extension reaction from the nick to generate a growing strand having sequence complementarity to at least a portion of the circular nucleic acid molecule. The circular nucleic acid molecule may be a circular double-stranded nucleic acid molecule, and the growing strand may exhibit sequence complementarity to at least a portion of a strand of the circular double-stranded nucleic acid molecule. The strand of the circular double-stranded nucleic acid molecule may be its sense strand, anti-sense strand, or both. In some examples, the at least the second enzyme may be a polymerase. The reaction mixture may further comprise at least one nucleotide coupled to a tag, wherein the at least the second enzyme incorporates the nucleotide into the growing strand. The tag may be a small molecule, nucleotide, polynucleotides, amino acid, polypeptide, polymers, metallic and/or ceramic particles, etc. In some examples, each of the nucleotides G, C, A, T, and U may comprise a different tag that is distinguishable from one another. In some examples, the tag may not be released from the nucleotide upon incorporation of the nucleotide into the growing strand. Alternatively, the at least the second enzyme may be capable of releasing the tag from the nucleotide upon incorporation of the nucleotide into the growing strand. The at least the second enzyme may perform the extension reaction with the help of at least one oligonucleotide primer. Alternatively, the at least the second enzyme may be capable of performing the extension reaction without use of an oligonucleotide primer. In an example, the extension reaction may comprise RCA, wherein the at least the second enzyme comprises a polymerase. The polymerase may bind to the nick of the nicking site for RCA.

The reaction mixture may further comprise at least a third enzyme that performs a cleavage reaction from the nick to cleave at least a portion of the circular nucleic acid molecule. Starting from the nick, the at least the third enzyme may displace and cleave at least a portion of a strand of the circular nucleic acid molecule. The at least the third enzyme may comprise a nuclease (e.g., an endonuclease, such as a restriction endonuclease).

At least a portion of the circular nucleic acid molecule may have or be suspected of having one or more variants in comparison to at least one reference sequence, as provided in the present disclosure. The reaction mixture may be used to prepare at least one composition for sequencing to identify a presence of the at least the portion of the circular nucleic acid molecule.

The circular nucleic acid molecule may comprise a recognition sequence, as provided in the present disclosure. The reaction mixture, thus, may further comprise a recognition moiety that associates with the recognition sequence to enrich for at least the circular nucleic acid molecule from a pool of random nucleic acid molecules in the composition based at least in part on the recognition sequence. The recognition moiety may comprise at least one oligonucleotide (e.g., at least a portion of a gRNA for a variation of a Cas system) having complementarity to at least the recognition sequence. The oligonucleotide of the recognition moiety may have at least 30%, 40%, 50%, 60%, 70%, 80%, 90%, 95%, or more complementarity to the recognition sequence. The oligonucleotide of the recognition moiety may have at most 100%, 95%, 90%, 80%, 70%, 60%, 50%, 40%, 30%, or less complementarity to the recognition sequence.

The composition of the reaction mixture may comprise a selected library of circular nucleic acid molecules (e.g., single-stranded or double-stranded). Each circular nucleic acid molecule of at least 5%, 10%, 15%, 20%, 25%, 30%, 35%, 40%, 45%, 50%, 60%, 70%, 80%, 90%, 95%, or more of the selected library may comprise the at least the portion of the recognition sequence. Each circular nucleic acid molecule of at most 100%, 95%, 90%, 80%, 70%, 60%, 50%, 45%, 40%, 35%, 30%, 25%, 20%, 15%, 10%, 5%, or less of the selected library may comprise the at least the portion of the recognition sequence.

The probability of occurrence of the recognition sequence without any mismatch may be at most once in every $1 \times 10^4$, $5 \times 10^4$, $7 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, or more nucleotides (or base pairs). Alternatively, the probability of occurrence of the recognition sequence without any mismatch may be at most twice, three times, four times, five times, or more in every $1 \times 10^4$, $5 \times 10^4$, $7 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$ $1 \times 10^{10}$, $5 \times 10^{10}$, $1 \times 10^{11}$, $5 \times 10^{11}$, $1 \times 10^{12}$, $5 \times 10^{12}$, or more nucleotides (or base pairs).

The recognition sequence may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The recognition sequence may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

In a different aspect, the present disclosure provides a cell-free library of circular nucleic acid molecules. Each individual circular nucleic acid molecule of at least 5% of the library may comprise (i) a target site and (ii) a nick at a known distance away from the target site. The library of circular nucleic acid molecules may be a starting material or a product of any one of the subject methods or reaction mixtures provided in the present disclosure.

The cell-free library of circular nucleic acid molecules may be a product or by-product of enrichment of a pool of random nucleic acid molecules for any nucleic acid molecule comprising a recognition site. In an example, a pool of random circular nucleic acid molecules may be enriched for at least one circular nucleic acid molecule comprising the recognition site, and treated with at least one enzyme (e.g., a nickase, such as a Cas9n nickase) to generate the nick at the known distance away from the target site. In another example, a pool of random circular nucleic acid molecules may be treated with at least one enzyme to generate the nick at the known distance away from the target site, and enriched for at least one circular nucleic acid molecule comprising the recognition site. In a different example, a pool of random linear nucleic acid molecules may be enriched for at least one linear nucleic acid molecule comprising the recognition site, treated with at least a first enzyme (e.g., ligase and/or recombinase) to circularize one or more of the linear nucleic acid molecules, and treated with at least a second enzyme (e.g., a nickase, such as a Cas9n nickase) to generate the nick at the known distance away from the target site. In a different example, a pool of random circular nucleic acid molecules may be enriched for at least one circular nucleic acid molecule comprising the recognition site, and treated with at least one enzyme (e.g., a recognition moiety) to insert a nicking site that may or may not have a nick present prior to the insertion. In a different example, a pool of random circular nucleic acid molecules may be treated with at least one enzyme (e.g., a recognition moiety) to insert a nicking site that may or may not have a nick present prior to the insertion, and enriched for at least one circular nucleic acid molecule comprising the recognition site. In a different example, a pool of random linear nucleic acid molecules may be treated with at least a first enzyme (e.g., a recognition moiety) to insert a nicking site that may or may not have a nick present prior to the insertion, treated with at least a second enzyme (e.g., ligase and/or recombinase) to circularize one or more of the linear nucleic acid molecules, and enriched for at least one circular nucleic acid molecule comprising the recognition site. In a different example, a pool of random linear nucleic acid molecules may be treated with at least a first enzyme (e.g., a recognition moiety) to insert a nicking site that may or may not have a nick present prior to the insertion, enriched for at least one linear nucleic acid molecule comprising the recognition site, and treated with at least a second enzyme (e.g., ligase and/or recombinase) to circularize one or more of the linear nucleic acid molecules. In another different example, a pool of random linear nucleic acid molecules may be enriched for at least one linear nucleic acid molecule comprising the recognition site, treated with at least a first enzyme (e.g., a recognition moiety) to insert a nicking site that may or may not have a nick present prior to the insertion, and treated with at least a second enzyme (e.g., ligase and/or recombinase) to circularize one or more of the linear nucleic acid molecules.

Each individual circular nucleic acid molecule of at least 5%, 10%, 20%, 25%, 30%, 35%, 40%, 45%, 50%, 55%, 60%, 65%, 70%, 75%, 80%, 85%, 90%, 95%, or more of the library may comprise (i) the target site and (ii) the nick at the known distance away from the target site. Each individual circular nucleic acid molecule of at most 100%, 95%, 90%, 85%, 80%, 75%, 70%, 65%, 60%, 55%, 50%, 45%, 40%, 35%, 30%, 25%, 20%, or less of the library may comprise (i) the target site and (ii) the nick at the known distance away from the target site.

The individual circular nucleic acid molecule may further comprise a recognition sequence. The probability of occurrence of the recognition sequence without any mismatch may be at most once in every $1 \times 10^4$, $5 \times 10^4$, $7 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, or more nucleotides (or base pairs). Alternatively, the probability of occurrence of the recognition sequence without any mismatch may be at most twice, three times, four times, five times, or more in every $1 \times 10^4$, $5 \times 10^4$, $7 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, or more nucleotides (or base pairs).

The recognition sequence may comprise at least 9, 10, 11, 12, 13, 14, 15, 16, 17, 18, 19, 20, 21, 22, 23, 24, 25, 26, 27, 28, 29, 30, 35, 40, 45, 50, or more nucleotides (or base pairs). The recognition sequence may comprise at most 50, 45, 40, 35, 30, 29, 28, 27, 26, 25, 24, 23, 22, 21, 20, 19, 18, 17, 16, 15, 14, 13, 12, 11, 10, 9, or fewer nucleotides (or base pairs).

The cell-free library may comprise at least a first individual nucleic acid molecule and a second individual nucleic acid molecule. In some examples, (i) a first target site of the first individual nucleic acid molecule and (ii) a second target site of the second individual nucleic acid molecule may be the same. In such a case, (1) a first known distance between a first nick and the first target site of the first individual nucleic acid molecule and (2) a second known distance between a second nick and the second target site of the second individual nucleic acid molecule may be the same. Alternatively, (1) a first known distance between a first nick and the first target site of the first individual nucleic acid molecule and (2) a second known distance between a second nick and the second target site of the second individual nucleic acid molecule may be different. In some examples, (i) a first target site of the first individual nucleic acid molecule and (ii) a second target site of the second individual nucleic acid molecule may be different. In such a case, (1) a first known distance between a first nick and the first target site of the first individual nucleic acid molecule and (2) a second known distance between a second nick and the second target site of the second individual nucleic acid molecule may be the same. Alternatively, (1) a first known distance between a first nick and the first target site of the first individual nucleic acid molecule and (2) a second known distance between a second nick and the second target site of the second individual nucleic acid molecule may be different.

The nicking site may be at no more than 100,000, 50,000, 10,000, 5,000, 1,000, 500, 400, 300, 200, 100, 90, 80, 70, 60, 50, 40, 30, 25, 20, 15, 10, 5, or fewer nucleotides away from the target site. The nicking site may be at least 5, 10, 15, 20, 25, 30, 40, 50, 60, 70, 80, 90, 100, 200, 300, 400, 500, 1,000, 5,000, 10,000, 50,000, 100,000, or more nucleotides away from the target site.

The circular nucleic acid molecule of the selected library may comprise a circular double-stranded nucleic acid molecule. The nick may be at a sense strand of the circular double-stranded nucleic acid molecule or at an anti-sense strand of the circular double-stranded nucleic acid molecule. The nick may be at a sense strand of the circular double-stranded nucleic acid molecule and at an anti-sense strand of the circular double-stranded nucleic acid molecule.

FIGS. 2A and 2B schematically illustrate example methods for generating a nick within a circular nucleic acid at a known distance away from a target site. Referring to FIG. 2A, a circular nucleic acid 210a may be provided. The circular nucleic acid 210a may comprise a target site 214 and a nickase binding site 212 specific for a nickase 220 (e.g., Cas9n). The target site 214 may have or be suspected of having one or more mutations compared to at least a reference sequence (e.g., a consensus sequence of a portion of a gene of a species or multiple species). The nickase binding site 212 may be at a known distance 216 away from the target site 214 (e.g., a known number of nucleotides between the nickase binding site 212 and the target site 214). The circular nucleic acid 210a may further comprise a recognition sequence 218, that is specifically recognizable by a recognition moiety 230 (e.g., Cas or dCas). The circular nucleic acid 210a may be treated with the nickase 220. The nickase 220 may bind to the nickase binding site 212 and create a nick, thereby forming a circular nucleic acid 210b with a nick 222 at, adjacent to, or within the nickase binding site 212. The nickase 220 may be removed or detached (e.g., automatically detached) upon creation of the nick 222. The nickase binding site 212 may be endogenous or exogenous to the circular nucleic acid 210a.

Referring to FIG. 2B, a circular nucleic acid 220a may be provided. The circular nucleic acid 220a may comprise the target site 214, as provided herein, and the recognition sequence 218 that is specifically recognizable by the recognition moiety 230 (e.g., Cas). The circular nucleic acid 220a may be treated with the recognition moiety 230 to generate a cleavage at, adjacent to, or within the recognition site 218. Upon generation of the cleavage, the nickase binding site 212 may be inserted (e.g., via homology-directed repair) into the cleavage, and the circular nucleic acid may be closed to form the circular nuclei acid molecule 220b. Subsequently, the nickase 220 may bind to the nickase binding site 212 and create a nick, thereby forming a circular nucleic acid molecule 220c with a nick 222 at, adjacent to, or within the nickase binding site 212. The nickase 220 may be removed or detached (e.g., automatically detached) upon creation of the nick 222.

FIGS. 2C and 2D schematically illustrate example methods for isolating or enriching for a circular nucleic acid comprising a recognition site and a target site. Referring to FIG. 2C, a pool of random nucleic acid molecules may comprise the circular nucleic acid molecule 210a that comprises the target site 214, the nickase binding site 212 at the known distance 216 away from the target site 214, and the recognition site 218. The pool of random nucleic acid molecules may be treated with at least the recognition moiety 150 (e.g., dCas) to form a recognition complex. In some examples, the recognition moiety 150 may be conjugated to a magnetic bead. Alternatively, the recognition moiety 150 may comprise one or more biotin molecules, which can subsequently be coupled to an avidin-presenting magnetic bead via avidin-biotin interaction. The resulting recognition complex may be pulled (separated) from other nucleic acid molecules lacking the recognition site 218 by magnetic bead separation. Similarly, a pool of random nucleic acid molecules comprising the circular nucleic acid molecule 210b may be enriched (e.g., by using the recognition moiety 150) for the circular nucleic acid molecule 210b.

Referring to FIG. 2D, a pool of random nucleic acid molecules may comprise the circular nucleic acid molecule 220a that comprises the target site 214 and the recognition site 218. Using a similar method provided in FIG. 2C (e.g., by using the recognition moiety), the pool may be enriched for the circular nucleic acid molecule 220a, or the circular nucleic acid molecule 220a may be isolated from the pool. Alternatively, a pool of random nucleic acid molecules may comprise the circular nucleic acid molecule 220b that comprises the target site 214, the nicking site 212 at the known distance 216 away from the target site 214, and the recognition site 218. Using a similar method provided in FIG. 2C (e.g., by using the recognition moiety), the pool may be enriched for the circular nucleic acid molecule 220b, or the circular nucleic acid molecule 220b may be isolated from the pool. In a different alternative, a pool of random nucleic acid molecules may comprise the circular nucleic acid molecule 220c that comprises the target site 214, the nick 222 at the known distance 216 away from the target site 214, and the recognition site 218. Using a similar method provided in FIG. 2C (e.g., by using the recognition moiety), the pool may be enriched for the circular nucleic acid molecule 220x, or the circular nucleic acid molecule 220c may be isolated from the pool.

Figure 3:
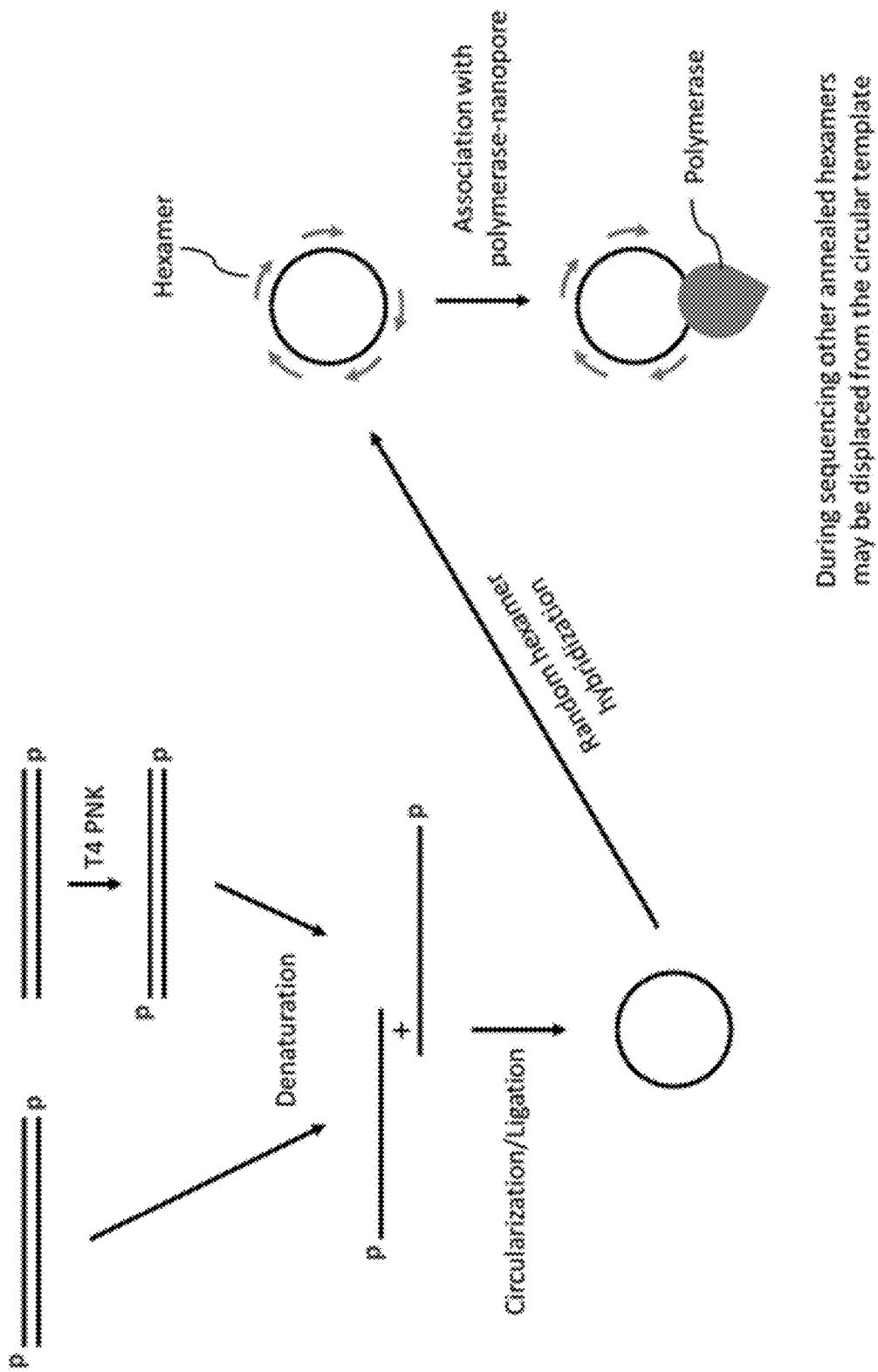
FIG. 3 schematically illustrates an example method for sequencing a double-stranded nucleic acid sequencing.

FIG. 3 schematically illustrates an example method for sequencing a double-stranded nucleic acid sequencing. A double-stranded nucleic acid molecule may be provided. The double-stranded nucleic acid molecule may be a fragmented or whole nucleic acid molecule from a biological sample. The double-stranded nucleic acid molecule may comprise two blunt ends. Alternatively, the double-stranded nucleic acid molecule may not comprise two blunt ends (e.g., only 1 or no blunt end). In such a case, end repair may be necessary, such that a repaired double-stranded nucleic acid molecule may (i) be free of overhangs, or (ii) contain 5' phosphate and 3' hydroxyl groups in the sense strand and the anti-send strand, as provided in FIG. 1D. Referring to FIG. 3, with or without such repair, the double-stranded nucleic acid molecule may be denatured into separate single-stranded nucleic acid molecules. Each individual single-stranded nucleic acid molecule may be circularized to form a single-stranded circular nucleic acid molecule. In some examples, the separated single-stranded nucleic acid molecules (e.g., a sense strand and an anti-sense strand that are at least partially or entirely complementary to one another) may be coupled (e.g., ligated), then circularized into one single-stranded circular nucleic acid molecule. Following, the circular nucleic acid molecules may be subjected under conditions sufficient for one or more random hexamer primers to hybridize to complementary domains of the circular nucleic acid molecules. The resulting circular nucleic acid molecules with one or more hybridized hexamers may be analyzed via sequencing-by-synthesis, e.g., detection of electrical signals or visualization by optical imaging.

In an example, nanopore sequencing can be used. A polymerase may bind to one of the hybridized hexamers and initiate extension reaction. During the extension reaction, other hybridized hexamers may be displaced from the circular nucleic acid molecule via direct or indirect activity of the polymerase. The polymerase may be positioned adjacent to or coupled to the nanopore (e.g., protein nanopore or a solid state nanopore).

Whole Genome and Targeted Sequencing

For whole genome sequencing, a binding site of the polymerase within a circular polynucleotide may not be controlled. A non-specific nicking enzyme may be used to nick a strand of the circular polynucleotide at a random location, and the polymerase may be bound to the non-specific nicking site, e.g., to perform an extension reaction. Alternatively, the binding site of the polymerase within a circular polynucleotide may not be controlled. A nickase that recognizes a specific sequence to bind and generate a nick may be used, e.g., Cas systems (e.g., a Cas nickase, such as Cas9n), N.Alw I, Nb.BbvCI, Nt.BbvCI, Nb.BsmI, Nt.BsmAI, Nt.BspQ1, Nb.BsrDI, Nt.BstNBI, Nb.BstsCI, Nt.CviPII, Nb.Bpu 1 OI, Nt.Bpu 1 OI and Nt,Bst9I, variations thereof, and combinations thereof.

Targeted polynucleotide sequencing may be useful for detecting a sequence variation (e.g., one or more mutations) at a specific location of the polynucleotide. The sequence variation may be, for example, a single nucleotide polymorphism (SNP). For targeted sequencing, it may be desirable that the polymerase be bound close to the polynucleotide sequence of interest (e.g., target site) such as the segment potentially containing a sequence variant (e.g., a mutation). In some examples, a Cas system comprising a Cas nickase and a sgRNA may be used. A polynucleotide segment having base pairs complementary to a polynucleotide sequence adjacent the polynucleotide segment of interest may be produced as a portion of the sgRNA. The sgRNA may be bound to a Cas9n nickase to form the sgRNA/Cas9n complex, which may be capable of binding to a polynucleotide at a segment identified by the at least a portion of the sgRNA, and generate the nick.

Figure 4A:
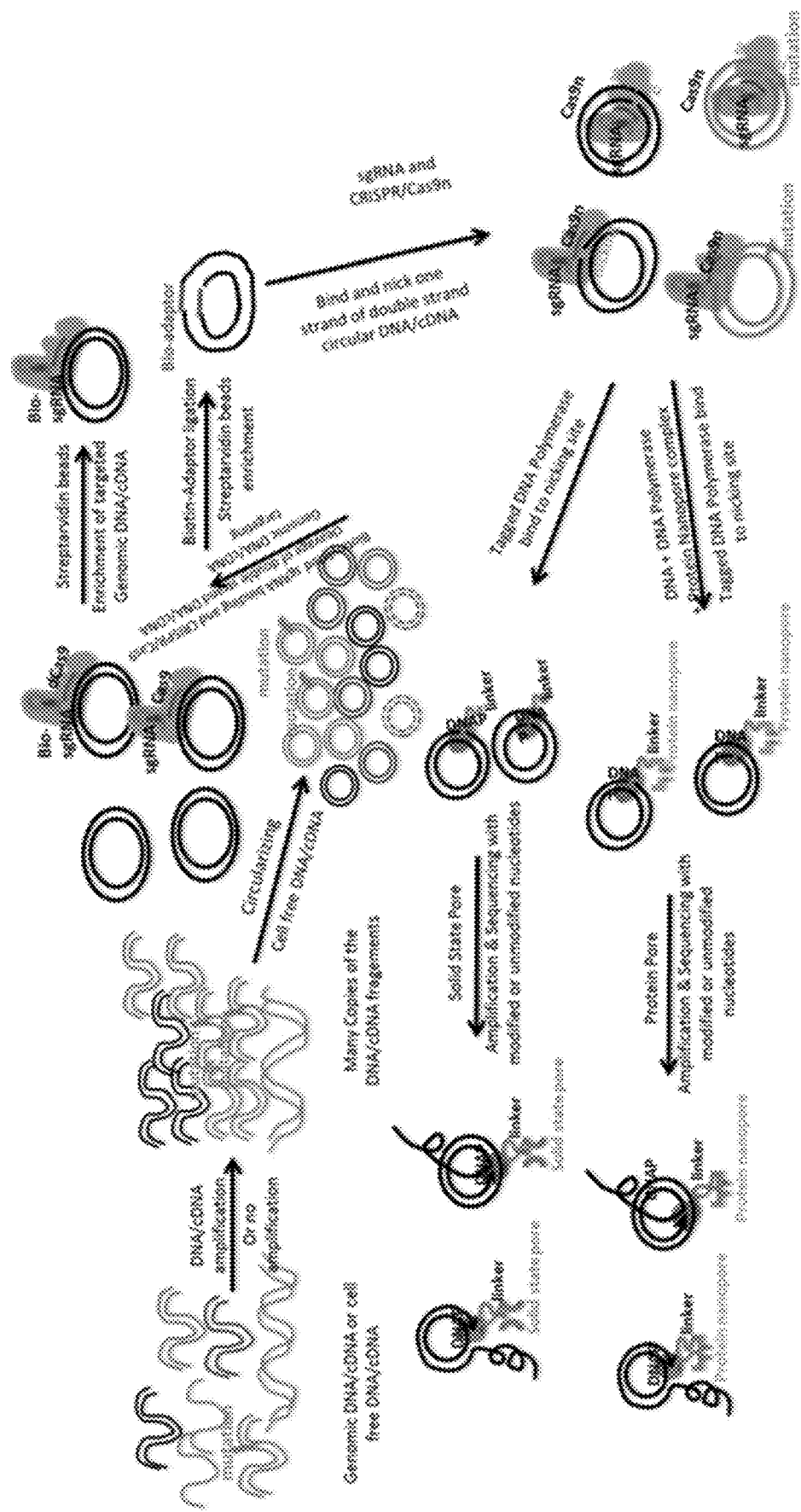
FIG. 4A schematically illustrates an example method for targeted sequencing using nanopore sequencing.

FIG. 4A schematically illustrates an example method for targeted sequencing using nanopore sequencing. A sample comprising genomic DNA/cDNA or cell free DNA/cfDNA can be amplified. To enrich the DNA/cDNA mixture with a targeted polynucleotide sequence, the genomic DNA/cDNA can be reacted with a biotinylated sgRNA/CRISPER/Cas9 complex to cleave the DNA/cDNA in a region of interest. The DNA mixture can be enriched with the targeted DNA segments by purifying using Streptarvidin beads. The enriched targeted DNA sample or cell free DNA, such as ctDNA, can then be circularized. The circular DNA can be bound to a sgRNA/CRISPR/Cas9n nickase to provide a nicking site in a DNA strand. The sgRNA comprises a nucleotide sequence complimentary to a nucleotide sequence of the DNA proximate to a region of interest such as a region potentially having a sequence variant. A polymerase is then bound to the nicking site. The polymerase/DNA complex is then associated with a nanopore and the DNA can be sequenced using rolling circle amplification and transcription.

Figure 4B:
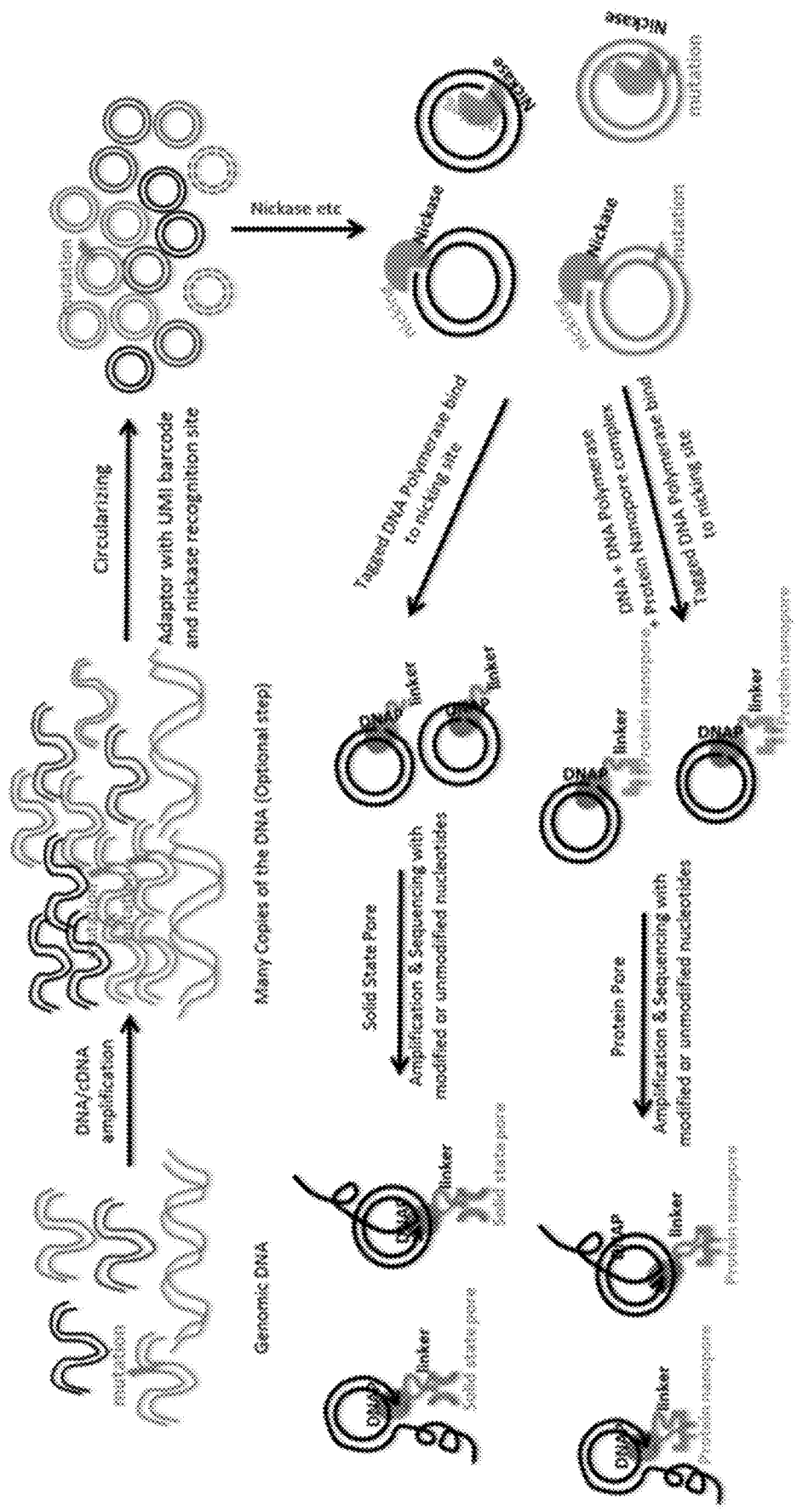
FIG. 4B schematically illustrates an example method for genomic sequencing using nanopore sequencing.

FIG. 4B schematically illustrates an example method for genomic sequencing using nanopore sequencing. The method can include the steps of providing a sample comprising genomic DNA, amplifying the genomic DNA, circularizing the genomic DNA to provide circular DNA, nicking the circular DNA with a nicking enzyme, to provide a nicking site on a strand of the circular DNA, binding a DNA polymerase to the nicking site, and amplifying and sequencing the circular DNA using a nanopore. In some examples, a restriction nickase may be used to generate a nick at its respective recognition sequence, and thus a distance between the nick and a target site (e.g., a mutated site) may not be controlled. Alternatively, a nickase (e.g., Cas9n complex) may be used to target a specific sequence of interest to generate a nick near or within the specific sequence of interest, thereby controlling a distance between the nick and a target site (e.g., a mutated site). A nicking site may be section of a single strand of DNA that has been removed to expose a 3' and 5' end. The 3' end may serve as a template from which the polymerase can bind and amplify.

Sample

Samples for analysis can comprise a plurality of polynucleotides. A polynucleotide can be single stranded DNA, double stranded DNA, or a combination thereof. The polynucleotides can comprise genomic DNA, genomic cDNA, cell free DNA, cell free cDNA, or a combination of any of the foregoing.

A polynucleotide can include cell-free DNA, circulating tumor DNA, genomic DNA, and DNA from formalin fixed and paraffin embedded (FFPE) samples. In some examples, an extracted DNA from a FFPE sample may be damaged, and such damaged DNA may be repaired by an available FFPE DNA repair kit. A sample can comprise any suitable DNA and/or cDNA sample such as for example, urine, stool, blood, saliva, tissue, biopsy, bodily fluid, or tumor cells.

The plurality of polynucleotides can be single-stranded or double-stranded.

A polynucleotide sample can be derived from any suitable source. For example, a sample can be obtained from a patient, from an animal, from a plant, or from the environment such as, for example, a naturally occurring or artificial atmosphere, a water system, soil, an atmospheric pathogen collection system, a sub-surface sediment, groundwater, or a sewage treatment plant.

Polynucleotides from a sample may include one more different polynucleotides, such as, for example, DNA, RNA, ribosomal RNA (rRNA), transfer RNA (tRNA), micro RNA (miRNA), messenger RNA (mRNA), fragments of any of foregoing, or combinations of any of the foregoing. A sample can comprise DNA. A sample can comprise genomic DNA. A sample can comprise mitochondrial DNA, chloroplast DNA, plasmid DNA, bacterial artificial chromosomes, yeast artificial chromosomes, oligonucleotide tags, or a combination of any of the foregoing.

The polynucleotides may be single-stranded, double-stranded, or a combination thereof. A polynucleotide can be a single-stranded polynucleotide, which may or may not be in the presence of double-stranded polynucleotides.

The starting amount of polynucleotides in a sample can be, for example, less than 50 ng, such as less than 45 ng, 40 ng, 35 ng, 30 ng, 25 ng, 20 ng, 15 ng, 10 ng, 5 ng, 4 ng, 3 ng, 2 ng, 1 ng, 0.5 ng, 0.1 ng, or less. The starting amount of polynucleotides in a sample can be, for example, more than 0.1 ng, such as more than 0.5 ng, 1 ng, 2 ng, 3 ng, 4 ng, 5 ng, 10 ng, 15 ng, 20 ng, 25 ng, 30 ng, 35 ng, 40 ng, 45 ng, 50 ng, or more. An amount of starting polynucleotides can be, for example, from 0.1 ng to 100 ng, from 1 ng to 75 ng, 5 ng to 50 ng, or from 10 ng to 20 ng.

The polynucleotides in a sample can be single-stranded, either as obtained or by way of treatment (e.g., denaturation). Further examples of suitable polynucleotides are described herein, such as with respect to any of the various aspects of the disclosure. Polynucleotides can be subjected to subsequent steps (e.g., circularization and amplification) without an extraction step, and/or without a purification step. For example, a fluid sample may be treated to remove cells without an extraction step to produce a purified liquid sample and a cell sample, followed by isolation of the polynucleotides from the purified fluid sample. A variety of procedures for isolation of polynucleotides are available, such as by precipitation or non-specific binding to a substrate followed by washing the substrate to release bound polynucleotides. Where polynucleotides are isolated from a sample without a cellular extraction step, polynucleotides will largely be extracellular or "cell-free" polynucleotides, which may correspond to dead or damaged cells. The identity of such cells may be used to characterize the cells or population of cells from which they are derived, such as in a microbial community.

A sample can be from a subject. A subject can be any suitable organism including, for example, plants, animals, fungi, protists, monerans, viruses, mitochondria, and chloroplasts. Sample polynucleotides can be isolated from a subject, such as a cell sample, tissue sample, bodily fluid sample, or organ sample or cell cultures derived from any of these, including, for example, cultured cell lines, biopsy, blood sample, cheek swab, or fluid sample containing a cell such as saliva. The subject may be an animal such as a cow, a pig, a mouse, a rat, a chicken, a cat, a dog, or a mammal, such as a human. A sample can comprise tumor cells, such as in a sample of tumor tissue from a subject.

A sample may not comprise intact cells, can be treated to remove cells, or polynucleotides are isolated without a cellular extractions step such as to isolate cell-free polynucleotides, such as cell-free DNA.

Other examples of sample sources include those from blood, urine, feces, nares, the lungs, the gut, other bodily fluids or excretions, a derivative thereof, or a combination thereof.

A sample from a single individual can be divided into multiple separate samples, such as 2, 3, 4, 5, 6, 7, 8, 9, 10, or more separate samples that are subjected to methods of the disclosure independently, such as analysis in duplicate, triplicate, quadruplicate, or more. Where a sample is from a subject, a reference sequence may also be derived from the subject, such as a consensus sequence from the sample under analysis or the sequence of polynucleotides from another sample or tissue of the same subject. For example, a blood sample may be analyzed for ctDNA mutations, and cellular DNA from another sample from the subject such as a buccal or skin sample, can be analyzed to determine a reference sequence.

Polynucleotides can be extracted from a sample, with or without extraction from cells in a sample, according to any suitable method.

A plurality of polynucleotides can comprise cell-free polynucleotides, such as cell-free DNA (cfDNA) or circulating tumor DNA (ctDNA). Cell-free DNA circulates in both healthy and diseased individuals. cfDNA from tumors (ctDNA) is not confined to any specific cancer type, but appears to be a common finding across different malignancies. The free circulating DNA concentration in plasma can be lower in control subjects in comparison to that in patients having or suspected of having a condition. In an example, the free circulating DNA concentration in plasma can be, for example, from 14 ng/mL to 18 ng/mL in control subjects and from 18 ng/mL to 318 ng/mL in patients with neoplasia.

Apoptotic and necrotic cell death may contribute to cell-free circulating DNA in bodily fluids. For example, significantly increased circulating DNA levels may be observed in plasma of prostate cancer patients and other prostate diseases, such as Benign Prostate Hyperplasia and Prostatits. In addition, circulating tumor DNA may be present in fluids originating from the organs where the primary tumor occurs. In an example, breast cancer detection can be achieved in ductal lavages; colorectal cancer detection in stool; lung cancer detection in sputum, and prostate cancer detection in urine or ejaculate. Cell-free DNA may be obtained from a variety of sources. An example source may be blood samples of a subject. However, cfDNA or other fragmented DNA may be derived from a variety of other sources including, for example, urine and stool samples can be a source of cfDNA, including ctDNA.

Methods for sequencing polynucleotides provided by the present disclosure can include retrieving a biological sample having a polynucleotide or collection of polynucleotides to be sequenced, extracting or otherwise isolating the polynucleotide sample from the biological sample, and, optionally, preparing the polynucleotide sample for sequencing.

Methods for sequencing a polynucleotide sample can comprise isolating the polynucleotide from a biological sample (e.g., tissue sample, fluid sample), and preparing the polynucleotide sample for sequencing. In some instances, the polynucleotide sample is extracted from a cell. Examples of techniques for extracting polynucleotides are using lysozyme, sonication, extraction, high pressures or any combination thereof. The polynucleotide is cell-free polynucleotide in some cases and does not require extraction from a cell.

In some cases, a polynucleotide sample may be prepared for sequencing by a process that involves removing proteins, cell wall debris and other components from the polynucleotide sample. There are many commercial products available for accomplishing this, such as, for example, spin columns. Alternatively or in addition to, ethanol precipitation and centrifugation may be used.

Nuclei Acid Fragmentation

Polynucleotides from a sample may be fragmented prior to further processing. Fragmentation may be accomplished by any suitable method, including chemical, enzymatic, and mechanical fragmentation. Fragments can have an average or median length of at least 10 nucleotides in length. Fragments can have an average or median length of at least 10, 50, 100, 500, 1,000, 5,000, 10,000, 50,000, or more nucleotides in length. Fragments can have an average or median length of at most 50,000, 10,000, 5,000, 1,000, 500, 100, 50, 10, or fewer nucleotides in length. Fragments can range from 90 nucleotides to 200 nucleotides, and/or have an average length of 150 nucleotides or any other suitable average length. Fragmentation of the polynucleotides can be accomplished mechanically comprising subjecting sample polynucleotides to acoustic sonication. Fragmentation can comprise treating the sample polynucleotides with one or more enzymes under conditions suitable for the one or more enzymes to generate double-stranded polynucleotide breaks. Examples of fragmentation enzymes include sequence specific and non-sequence specific nucleases. Examples of suitable nucleases include DNase I, Fragmentase, restriction endonucleases, variants thereof, and combinations of any of the foregoing. Fragmentation can comprise treating the sample polynucleotides with one or more restriction endonucleases. Fragmentation can produce fragments having 5' overhangs, 3' overhangs, blunt ends, or a combination thereof. When fragmentation comprises the use of one or more restriction endonucleases, cleavage of sample polynucleotides leaves overhangs having a predictable sequence. Fragmented polynucleotides may be subjected to a step of size selecting the fragments via standard methods such as column purification or isolation from an agarose gel.

Linear Nucleic Acid Amplification

Polynucleotides in a sample can be amplified. The polynucleotides can be amplified using methods such as by primer extension reaction using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof.

Amplified polynucleotides can be subjected to sequencing with or without enrichment, such as enriching for one or more target polynucleotides among the amplified polynucleotides by performing an enrichment step prior to sequencing. An enrichment step can comprise hybridizing amplified polynucleotides to a plurality of probes attached to a substrate. An enrichment step can comprise amplifying a target sequence comprising sequence A and sequence B oriented in a 5' to 3' direction in an amplification reaction mixture comprising: (a) the amplified polynucleotides; (b) a first primer comprising sequence A', wherein the first primer specifically hybridizes to sequence A of the target sequence via sequence complementarity between sequence A and sequence A; (c) a second primer comprising sequence B, wherein the second primer specifically hybridizes to sequence B' present in a complementary polynucleotide comprising a complement of the target sequence via sequence complementarity between B and B; and (d) a polymerase that extends the first primer and the second primer to produce amplified polynucleotides; wherein the distance between the 5' end of sequence A and the 3' end of sequence B of the target sequence is 75nt or less.

Enrichment of Samples

Regions of genomic DNA and cDNA of interest can be selectively targeted and amplified. A targeted region can comprise, for example, a region comprising a sequence variant of interest for diagnostic purposes.

A polynucleotide region of interest can be cleaved by binding a biotinylated sgRNA/CRISPR/Cas9 complex to a region of the polynucleotide proximate to the region of interest. The sgRNA can comprise a sequence complimentary to that of the polynucleotide at a region proximate to the region of interest. The sgRNA/CRISPR/Cas9 complex can cleave the double-stranded polynucleotide into polynucleotide segments. The composition comprising targeted polynucleotide segments and non-target polynucleotide segments can be enriched with the targeted polynucleotide segments using one or more purification methods such as binding the targeted segments to streptarvidin beads.

Polynucleotide mixtures enriched with polynucleotide segments of interest can then be circularized.

Linear Nucleic Acid Circularization

A polynucleotide sample can comprise single-stranded polynucleotides. Circularizing such polynucleotides can be accomplished by subjecting the plurality of polynucleotides to a ligation reaction. A circular polynucleotide can have a junction that is unique among the circularized polynucleotides.

Circularization can include joining the 5' end of a polynucleotide to the 3' end of the same polynucleotide, to the 3' end of another polynucleotide in the sample, or to the 3' end of a polynucleotide from a different source (e.g., an artificial polynucleotide, such as an oligonucleotide adapter). For example, the 5' end of a polynucleotide can be joined to the 3' end of the same polynucleotide (also referred to as "self-joining"). Conditions of the circularization reaction can be selected to favor self-joining of polynucleotides within a particular range of lengths, so as to produce a plurality of circularized polynucleotides characterized by a particular average length. For example, circularization reaction conditions can be selected to favor self-joining of polynucleotides shorter than 5,000, 2,500, 1,000, 750, 500, 400, 300, 200, 150, 100, 50, or fewer nucleotides in length. Polynucleotide fragments having lengths between 50 to 5000 nucleotides, 100 to 2500 nucleotides, or 150 to 500 nucleotides can be favored, such that the average length of circularized polynucleotides is within a desired range. For example, 80% or more of the circularized polynucleotide fragments can be between 50 to 500 nucleotides in length, such as between 50 to 200 nucleotides in length. Reaction conditions that may be optimized include the length of time for a joining reaction, the concentration of various reagents, and/or the concentration of the polynucleotides to be joined. A circularization reaction can preserve the distribution of fragment lengths present in a sample prior to circularization. For example, one or more of the mean, median, mode, and standard deviation of fragment lengths in a sample before circularization and of circularized polynucleotides are within 75%, 80%, 85%, 90%, 95%, or more of one another.

Rather than forming self-joined circular polynucleotides, one or more adapter oligonucleotides can be used, such that the 5' end and 3' end of a polynucleotide in the sample is joined by way of one or more intervening adapter oligonucleotides to form a circular polynucleotide. For example, the 5' end of a polynucleotide can be joined to the 3' end of an adapter, and the 5' end of the same adapter can be joined to the 3' end of the same polynucleotide. An adapter oligonucleotide can include any suitable oligonucleotide having a sequence, at least a portion of which is known, that can be joined to a sample polynucleotide. Adapter oligonucleotides can comprise, for example, DNA, RNA, nucleotide analogs, non-canonical nucleotides, labeled nucleotides, modified nucleotides, or combinations of any of the foregoing. Adapter oligonucleotides can be single-stranded, double-stranded, or partial duplex. A partial-duplex adapter can comprise one or more single-stranded regions and one or more double-stranded regions. Double-stranded adapters can comprise two separate oligonucleotides hybridized to one another, such as an oligonucleotide duplex, and hybridization may leave one or more blunt ends, one or more 3' overhangs, one or more 5' overhangs, one or more bulges resulting from mismatched and/or unpaired nucleotides, or a combination of any of the foregoing. When two hybridized regions of an adapter are separated from one another by a non-hybridized region, a "bubble" structure results. Adapters having different nucleotide sequences can be used. Different adapters can be joined to sample polynucleotides in sequential reactions or simultaneously. Identical adapters can be added to both ends of a target polynucleotide. For example, first and second adapters can be added to the same reaction. Adapters can be manipulated prior to combining with sample polynucleotides. For example, terminal phosphates can be added or removed.

Any suitable method can be used for circularizing the polynucleotides. For example, circularization can comprise an enzymatic reaction, such as use of a ligase, such as an RNA or DNA ligase. Examples of suitable ligases include Circligase™ (Epicentre; Madison, Wis.), RNA ligase, T4 RNA Ligase 1 (ssRNA Ligase), NAD-dependent ligases such as Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, ATP-dependent ligases such as T4 RNA ligase, T4 DNA ligase, T3 DNA ligase, T7 DNA ligase, Pfu DNA ligase, DNA ligase 1, DNA ligase III, and DNA ligase IV.

For self-joining circularization, the concentration of polynucleotides and enzyme can be adjusted to facilitate the formation of intramolecular circles rather than intermolecular structures. Reaction temperatures and times can also be adjusted. An exonuclease step can be included to digest any unligated polynucleotides after the circularization reaction. For example, circular polynucleotides do not contain a free 5' or 3' end, and thus the introduction of a 5' or 3' exonuclease will not digest the closed circles but will digest the unligated polynucleotides.

Joining ends of a polynucleotide to one-another to form a circular polynucleotide, either directly, or with one or more intermediate adapter oligonucleotides, can produce a junction having a junction sequence. Where the 5' end and 3' end of a polynucleotide are joined via an adapter polynucleotide, a junction may be referred to a junction between the polynucleotide and the adapter (e.g., one of the 5' end junction or the 3' end junction), or to the junction between the 5' end and the 3' end of the polynucleotide as formed by and including the adapter polynucleotide. Where the 5' end and the 3' end of a polynucleotide are joined without an intervening adapter, such as the 5' end and 3' end of a single-stranded DNA, a junction may be referred to the point at which the two ends are joined. A junction may be identified by the sequence of nucleotides comprising the junction, i.e., the junction sequence. Samples comprising polynucleotides having a mixture of ends formed by natural degradation processes such as cell lysis, cell death, and other processes by which DNA is released from a cell to its surrounding environment in which it may be further degraded, such as in cell-free polynucleotides, fragmentation that is a byproduct of sample processing such as fixing, staining, and/or storage procedures, and fragmentation by methods that cleave DNA without restriction to specific target sequences such as mechanical fragmentation or non-sequence specific nuclease treatment using for example, DNase I, fragmentase. Where samples can comprise polynucleotides having a mixture of ends, the likelihood that two polynucleotides will have the same 5' end or 3' end is low, and the likelihood that two polynucleotides will independently have both the same 5' end and 3' end is extremely low. In such mixtures, junctions may be used to distinguish different polynucleotides, even where the two polynucleotides comprise a portion having the same target sequence. Where polynucleotide ends are joined without an intervening adapter, a junction sequence may be identified by alignment to a reference sequence. For example, where the order of two component sequences appears to be reversed with respect to the reference sequence, the point at which the reversal appears to occur may be an indication of a junction. Where polynucleotide ends are joined via one or more adapter sequences, a junction may be identified by proximity to the known adapter sequence, or by alignment as above if a sequencing read is of sufficient length to obtain sequence from both the 5' and 3' ends of the circularized polynucleotide. The formation of a particular junction can be sufficiently rare event such that it is unique among the circularized polynucleotides of a sample.

Circular Nucleic Acid Amplification

Methods provided by the present disclosure can include amplifying the circular polynucleotides. For example, a plurality of different circular polynucleotides comprising a target sequence, wherein the target sequence comprises sequence A and sequence B oriented in a 5' to 3' direction, can be amplified. A method of amplifying circular DNA can comprise subjecting circular DNA to a polynucleotide amplification reaction wherein the reaction amplification reaction mixture comprises (a) the plurality of circular polynucleotides, wherein individual circular polynucleotides in the plurality comprise different junctions formed by circularizing individual polynucleotides having a 5' end and a 3' end; (b) a first primer comprising sequence A', wherein the first primer specifically hybridizes to sequence A of the target sequence via sequence complementarity between sequence A and sequence A; (c) a second primer comprising sequence B, wherein the second primer specifically hybridizes to sequence B' present in a complementary polynucleotide comprising a complement of the target sequence via sequence complementarity between sequence B and B; and (d) a polymerase that extends the first primer and the second primer to produce amplified polynucleotides; wherein sequence A and sequence B are endogenous sequences, and the distance between the 5' end of sequence A and the 3' end of sequence B of the target sequence is 75 nucleotide or less.

After circularization, the circular double-stranded polynucleotides can be amplified. A variety of methods for amplifying circular polynucleotides (e.g., DNA and/or RNA) are available. Amplification may be linear, exponential, or involve both linear and exponential phases in a multi-phase amplification process. Amplification methods may involve changes in temperature, such as a heat denaturation step, or may be isothermal processes that do not require heat denaturation. Examples of suitable amplification processes include rolling circle amplification (RCA). In RCA, the reaction mixture can comprise one or more primers, a polymerase, and dNTPs, and produces concatemers. A polymerase in an RCA reaction can be a polymerase having strand-displacement activity. Various suitable polymerases are available, including, for example, exonuclease minus DNA Polymerase I large (Klenow) Fragment, Phi29 DNA polymerase, and Taq DNA Polymerase. As a result of RCA, a concatemer polynucleotide amplification product comprising is formed having two or more copies of a target sequence from a template polynucleotide, such as, for example, 2, 3, 4, 5, 6, 7, 8, 9, 10, or more copies of the target sequence. Amplification primers may be of any suitable length, such as, for example, at least 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes. RCA processes can employ, for example, random primers, target-specific primers, adapter-targeted primers, or no primer.

Purification

After circularization of the polynucleotides such as double-stranded DNA to provide circular dsDNA, the circular dsDNA can be purified prior to amplification or sequencing to increase the relative concentration or purity of circular polynucleotides for use in subsequence steps such as by isolation of circular polynucleotides or removal of one or more other molecules in the reaction). For example, the mixture containing double-stranded polynucleotides can be treated to remove a non-circularized polynucleotides (e.g., single-stranded or double-stranded) with an exonuclease or can be subjected to size exclusion chromatography, whereby small reagents are retained and discarded or circularization products are retained and released in a separate volume. Purification can comprise treatment to remove or to degrade ligase used in the circularization reaction, and/or to purify circularized polynucleotides away from such ligase. Treating to degrade ligase can comprise treatment with a protease.

Nicking

A mixture of circular polynucleotides, such as a mixture of circular DNA, circular cDNA, circular ctDNA, or a combination thereof, can be reacted with a nicking enzyme (e.g., a CRISPR/Cas9n complex) to cleave a segment of a single strand of the circular polynucleotide, thereby forming a nick in a strand of the polynucleotide. For circular double-stranded polynucleotides, the CRISPR/Cas9n complex can bind to and cleave a segment of either the inner strand or the outer strand.

A CRISPR/Cas9n nickase complex can be used to remove a segment, i.e., form a nick at a portion of the polynucleotide targeted by at least a portion of a gRNA of the CRISPR/Cas9n complex. This approach can be appropriate for whole genome sequencing and/or targeted sequencing. In some examples, the CRISPR-Cas9n system can be adapted to target specific nucleotide sequences by complexing with a short RNA molecule to recognize a specific DNA target, referred to as a short guide RNA (sgRNA). To target a particular polynucleotide region of interest, a sgRNA/CRISPR/Cas9n complex can be used to bind the nickase to a region of the polynucleotide proximate a region of interest. The nicking enzyme can expose a 3' and 5' ends of the circular DNA, and the 3' end may serve as a binding site for amplification and/or reverse transcription sequencing (e.g., using a polymerase such as a DNA polymerase).

Therapeutic Applications

Methods, systems, and compositions provided herein can be directed to one or more therapeutic applications, such as in the characterization of a patient sample and optionally diagnosis of a condition of a subject. Therapeutic applications can include informing the selection of therapies to which a patient may be most responsive and/or treatment of a subject in need of therapeutic intervention based on the results of methods provided by the present disclosure.

For example, methods provided by the present disclosure can be used to diagnose tumor presence, progression and/or metastasis of tumors, such as when the polynucleotides analyzed comprise or consist of cfDNA, ctDNA, or fragmented tumor DNA. A subject may be monitored for tumor treatment efficacy, for example, by monitoring ctDNA over time, a decrease in ctDNA can be used as an indication of treatment efficacy, and increases in ctDNA can inform selection of different treatments and/or different dosages. Other uses include evaluations of organ rejection in transplant recipients such as where increases in the amount of circulating DNA corresponding to the transplant donor genome is used as an early indicator of transplant rejection, and genotyping/isotyping of pathogen infections, such as viral or bacterial infections. Detection of sequence variants in circulating fetal DNA may be used to diagnose a condition of a fetus.

Methods provided by the present disclosure can comprise diagnosing a subject based on a result of the sequencing, such as diagnosing the subject with a disease associated with a detected causal genetic variant, or reporting a likelihood that the patient has or will develop such disease.

A causal genetic variant can include sequence variants associated with a particular type or stage of cancer, or of cancer having a particular characteristic such as metastatic potential, drug resistance, and/or drug responsiveness. Methods provided by the present disclosure can be used to inform therapeutic decisions, guidance and monitoring, of cancer therapies. For example, treatment efficacy can be monitored by comparing patient ctDNA samples from before, during, and after treatment with particular including molecular targeted therapies such as monoclonal drugs, chemotherapeutic drugs, radiation protocols, and combinations of any of the foregoing. For example, the ctDNA can be monitored to see if certain mutations increase or decrease, or new mutations appear, after treatment, which can allow a physician to modify a treatment in a much shorter period of time than afforded by methods of monitoring that track patient symptoms. Methods can comprise diagnosing a subject based on the results of polynucleotide sequencing, such as diagnosing the subject with a particular stage or type of cancer associated with a detected sequence variant, or reporting a likelihood that the patient has or will develop such cancer.

For example, for therapies that are specifically targeted to patients on the basis of molecular markers, patients can be tested to find out if certain mutations are present in their tumor, and these mutations can be used to predict response or resistance to the therapy and guide the decision whether to use the therapy. Detecting and monitoring ctDNA during the course of treatment can be useful in guiding treatment selections.

Sequence variants associated with one or more kinds of cancer that may be used for diagnosis, prognosis, or treatment decisions. For example, suitable target sequences of oncological significance include alterations in the TP53 gene, the ALK gene, the KRAS gene, the PIK3CA gene, the BRAF gene, the EGFR gene, and the KIT gene. A target sequence the may be specifically amplified, and/or specifically analyzed for sequence variants may be all or part of a cancer-associated gene.

Methods provided by the present disclosure can be useful in discovering new, rare mutations that are associated with one or more cancer types, stages, or cancer characteristics. For example, in populations of individuals sharing a characteristic under analysis such as a particular disease, type of cancer, and/or stage of cancer, using methods provided by the present disclosure sequence variants can be identified reflecting mutations in particular genes or parts of genes. Identified sequence variants occurring with a statistically significantly greater frequency among the group of individuals sharing the characteristic than in individuals without the characteristic may be assigned a degree of association with that characteristic. The sequence variants or types of sequence variants so identified may then be used in diagnosing or treating individuals discovered to harbor them.

Additional therapeutic applications can include use in non-invasive fetal diagnostics. Fetal DNA can be found in the blood of a pregnant woman. Methods provided by the present disclosure can be used to identify sequence variants in circulating fetal DNA, and thus may be used to diagnose one or more genetic diseases in the fetus, such as those associated with one or more causal genetic variants. Examples of causal genetic variants include trisomies, cystic fibrosis, sickle-cell anemia, and Tay-Saks disease. The mother may provide a control sample and a blood sample to be used for comparison. The control sample may be any suitable tissue, and can then be sequenced to provide a reference sequence. Sequences of cfDNA corresponding to fetal genomic DNA can then be identified as sequence variants relative to the maternal reference. The father may also provide a reference sample to aid in identifying fetal sequences, and sequence variants.

Different therapeutic applications can include detection of exogenous polynucleotides, including from pathogens such as bacteria, viruses, fungi, and microbes, which information may inform a treatment.

Sequencing Apparatus

Impedance-Based Sequencing

In an aspect, the present disclosure provides a method for processing or analyzing a nucleic acid molecule. The method may comprise providing the nucleic acid molecule adjacent to a nanopore. The method may comprise bringing the nucleic acid molecule in contact with a nucleotide having a tag under conditions sufficient to incorporate the nucleotide into a nucleic acid strand that is complementary to at least a portion of the nucleic acid molecule. Upon incorporation of the nucleotide into the nucleic acid strand, at least a portion of the tag may be disposed within the nanopore. The method may comprise detecting one or more signals indicative of an impedance or impedance change in the nanopore when at least a portion of the tag is within the nanopore. The method may comprise using the one or more signals to identify the nucleotide incorporated into the nucleic acid strand. The method may further comprise measuring an electrical current or change thereof when at least the portion of the tag is disposed within the nanopore.

The nanopore may be disposed adjacent to or in proximity to a sensing circuit or an electrode coupled to an electrical circuit (e.g., CMOS or FET circuit). The electrical circuit may be coupled to a voltage source. Alternatively, the nanopore may be part of the electrical circuit. A constant voltage may be applied to the electrical circuit, and a change in the current may be measured. Alternatively, a change in voltage necessary to maintain a steady state current may be measured. The nanopore may be part of an electrical circuit that comprises a tunneling junction. The nanopore may be the tunneling junction of the nanopore. Alternatively, the nanopore may not be part of an electrical circuit that comprises a tunneling junction. The nanopore may be in an electrolytic solution (e.g., 0.5 M Potassium Acetate and 10 mM KCl). Alternatively, the nanopore may not be in an electrolytic solution.

The one or more signals may be a current or voltage measured from the sensing circuit. The one or more signals may be a current and voltage measured from the sensing circuit. The signal may be a tunneling current. Alternatively, the signal may not be a tunneling current. The current may be a Faradaic current. Alternatively, the current may not be a Faradaic current. The current may be at least 1 picoamp (pA), 10 pA, 100 pA, 1 nanoamp (nA), 10 nA, 100 nA, 1 microamp (mA), 10 mA, 100 mA, or more. The current may be at most 100 mA, 10 mA, 1 mA, 100 nA, 10 nA, 1 nA, 100 pA, 10 pA, 1 pA, or less. The current may be at least in the picoamp (pA) range, tens of pA range, hundreds of pA range, nanoamp (nA) range, tens of nA range, hundreds of nA range, microamp (mA) range, tens of mA range, or higher. The current may be at most in the tens of mA range, mA range, hundreds of nA range, tens of nA range, nA range, hundreds of pA range, tens of pA range, pA range, or lower. The voltage may be at least 0.1 millivolt (mV), 0.5 mV, 1 mV, 5 mV, 10 mV, 50 mV, 100 mV, 500 mV, or more. The voltage may be at most 500 mV, 100 mV, 50 mV, 10 mV, 5 mV, 1 mV, 0.5 mV, 0.1 mV, or less. The voltage may be at least in the millivolt (mV) range, tens of mV range, hundreds of mV range, or higher. The voltage may be at most in the hundreds of mV range, tens of mV range, mV range, or lower.

The electrical circuit may comprise a plurality of electrodes (e.g., metal electrodes). The electrical circuit may comprise at least 2, 3, 4, 5, 6, 7, 8, 9, 10, or more electrodes. The electrical circuit may comprise at most 10, 9, 8, 7, 6, 5, 4, 3, or 2 electrodes. The plurality of electrodes may not be in direct contact with the nanopore. Alternatively, the plurality of electrodes may be in direct contact with the nanopore. In another alternative, some electrodes may be in direct contact with the nanopore, while the other electrodes may not in direct contact with the nanopore. In some cases, the nanopore may include the plurality of electrodes. Alternatively, the nanopore may not include the plurality of electrodes. The identifying the nucleotide incorporated into the nucleic acid strand may comprise using the plurality of electrodes to detect the one or more signals.

The nanopore may comprise a protein nanopore or a solid state nanopore. The nanopore may comprise the protein nanopore and the solid state nanopore. The nanopore can have a characteristic width or diameter, for example, on the order of about 0.1 nm to 1,000 nm. The width or diameter of the nanopore may be at least 0.1 nm, 0.5 nm, 1 nm, 5 nm, 10 nm, 50 nm, 100 nm, 500 nm, 1,000 nm, or more. The width or diameter of the nanopore may be at most 1,000 nm, 500 nm, 100 nm, 50 nm, 10 nm, 5 nm, 1 nm, 0.5 nm, 0.1 nm, or less.

The method may further comprise, prior to detecting the one or more signals indicative of the impedance or impedance change in the nanopore, releasing the tag from the nucleotide upon incorporation of the nucleotide into the nucleic acid strand. At least one enzyme may incorporate the nucleotide into the nucleic acid strand that is complementary to the at least the portion of the nucleic acid molecule. The at least one enzyme may further release the tag from the nucleotide prior to, during, or subsequent to the incorporation. Alternatively or in addition to, an additional enzyme (which may be operatively coupled to the at least one enzyme) may release the tag from the nucleotide prior to, during, or subsequent to the incorporation. At least a portion of the released tag may enter the nanopore, and the method may comprise detecting one or more signals indicative of the impedance or impedance change in the nanopore when the at least the portion of the released tag is within the nanopore.

The nucleic acid molecule comprises a circular nucleic acid molecule. The circular nucleic acid molecule may be single-stranded or double-stranded. Alternatively, a first portion of the circular nucleic acid molecule may be single-stranded, and a second portion of the circular nucleic acid molecule may be double-stranded. In some examples, the nucleic acid molecule may comprise a linear nucleic acid molecule that is single-stranded or double-stranded.

The incorporation may be performed with use of at least one oligonucleotide primer. Alternatively, the incorporation may be performed without use of an oligonucleotide primer. The method may further comprise, prior to detecting the one or more signals indicative of the impedance or impedance change in the nanopore, subjecting the nucleic acid molecule to RCA to generate the nucleic acid strand. The RCA may generate the nucleic acid strand that comprises at least 1, 2, 3, 4, 5, 6, 7, 8, 9, 10, or more copies of at least a portion of the nucleic acid molecule (e.g., at least a portion of at least one strand of the nucleic acid molecule). The RCA may generate the nucleic acid strand that comprises at most 10, 9, 8, 7, 6, 5, 4, 3, 2, or 1 copy of the at least the portion of the nucleic acid molecule.

The providing may comprise coupling at least one enzyme that performs the incorporation to (i) at least a portion of the nanopore or (ii) a membrane having the nanopore. The providing may comprise coupling at least one enzyme that performs the incorporation to (i) at least a portion of the nanopore and (ii) a membrane having the nanopore. The coupling may comprise conjugating the at least one enzyme to the nanopore or the membrane. The coupling may comprise conjugating the at least one enzyme to the nanopore and the membrane. The coupling may be covalent (e.g., cross-linking or conjugating). The coupling may be performed via another enzyme, such as transglutaminase, sortase, subtilisin, tyrosinase, laccase, etc., or via a chemical cross-linker, such as 1-Ethyl-3-(3-dimethylaminopropyl)carbodiimide (EDC), N,N'-dicyclohexylcarbodiimide (DCC), N,N'-Diisopropylcarbodiimide (DIC), etc. Alternatively or in addition to, the coupling may be non-covalent, e.g., via hydrogen bonds, magnetic interaction, etc.

The membrane may be a lipid bilayer. The membrane may be a solid state membrane (e.g., a film). The membrane may be a combination of the lipid bilayer and the solid state membrane. The at least one enzyme may be a polymerase, a nuclease, a functional variant thereof, or a combination thereof.

In another aspect, the present disclosure provides a system for processing or analyzing a nucleic acid molecule. The system may comprise a nanopore configured to receive at least a portion of a tag upon incorporation of a nucleotide comprising the tag into a nucleic acid strand. The nucleic acid strand may be complementary to at least a portion of the nucleic acid molecule. The nanopore may be configured detect one or more signals indicative of an impedance or impedance change in the nanopore when the at least the portion of the tag is within the nanopore. The one or more signals may be usable to identify the nucleotide incorporated into the nucleic acid strand. The system for processing or analyzing the nucleic acid molecule may be configured to perform one or more subject methods provided in the present disclosure for processing or analyzing the nucleic acid molecule or a derivative thereof.

The one or more signals may be a current or voltage. The one or more signals may be a current and voltage. The current may be a Faradaic current. Alternatively, the current may not be a Faradaic current. The one or more signals may not be a tunneling current. Alternatively, the one or more signals may be a tunneling current. The nanopore may be part of an electrical circuit that comprises a tunneling junction. Alternatively, the nanopore may not be part of an electrical circuit that comprises a tunneling junction.

The nanopore may be configured to measure an electrical current or change thereof when at least the portion of the tag is disposed within the nanopore. Alternatively, the nanopore may be configured to measure an electrical current or change thereof when at least the portion of the tag is released from within the nanopore. The nanopore may include a plurality of electrodes configured to detect the one or more signals. Alternatively. the nanopore may not include a plurality of electrodes configured to detect the one or more signals, and the plurality of electrodes may be operatively coupled to the nanopore to detect the one or more signals.

The nanopore may comprise a protein nanopore or a solid state nanopore. The nanopore may comprise the protein nanopore and the solid state nanopore.

The system may further comprise at least one enzyme configured to perform the incorporation. The least one enzyme may incorporate the nucleotide into the nucleic acid strand that is complementary to the at least the portion of the nucleic acid molecule. The at least the portion of the tag may be released from the nucleotide upon incorporation of the nucleotide into the nucleic acid strand. The at least one enzyme may release the tag from the nucleotide prior to, during, or subsequent to the incorporation. Alternatively or in addition to, an additional enzyme (which may be operatively coupled to the at least one enzyme) may release the tag from the nucleotide prior to, during, or subsequent to the incorporation. At least a portion of the released tag may enter the nanopore, and the method may comprise detecting one or more signals indicative of the impedance or impedance change in the nanopore when the at least the portion of the released tag is within the nanopore. The at least one enzyme may be a polymerase, a nuclease, a functional variant thereof, or a combination thereof.

The incorporation may be performed with use of at least one oligonucleotide primer. Thus, the system may further comprise the at least one oligonucleotide primer. Alternatively, the incorporation may be performed without use of an oligonucleotide primer. Thus, the system may not comprise the oligonucleotide primer.

The at least one enzyme (and/or the additional enzyme) may be coupled to (i) at least a portion of the nanopore or (ii) a membrane having the nanopore. The at least one enzyme (and/or the additional enzyme) may be coupled to (i) at least a portion of the nanopore and (ii) a membrane having the nanopore. The at least one enzyme (and/or the additional enzyme) may be conjugated to (i) at least a portion of the nanopore or (ii) a membrane having the nanopore. The at least one enzyme (and/or the additional enzyme) may be conjugated to (i) at least a portion of the nanopore and (ii) a membrane having the nanopore. The membrane may be a lipid bilayer or a solid state membrane. The membrane may be a lipid bilayer and a solid state membrane.

The coupling may be performed by a coupling enzyme and/or a chemical cross-linker. The system may further comprise the coupling enzyme (e.g., transglutaminase, sortase, subtilisin, tyrosinase, laccase, etc.) or the chemical cross-linker (e.g., EDC, DCC, DIC, etc.). The system may comprise the coupling enzyme and the chemical cross-linker. Alternatively, the nanopore or the membrane may be configured to bind to at least a portion of the at least one enzyme (and/or the additional enzyme). The nanopore or the membrane may comprise a binding moiety (e.g., a small molecule, nucleotide, peptide, polymer, a combination thereof, etc.) capable of binding to the at least the portion of the at least one enzyme. In a different alternative, the at least one enzyme may be configured to bind to at least a portion of the nanopore or at least a portion of the membrane. The at least one enzyme may comprise a binding moiety (e.g., a small molecule, nucleotide, peptide, polymer, a combination thereof, etc.) capable of binding to the at least the portion of the membrane.

Figure 5A:
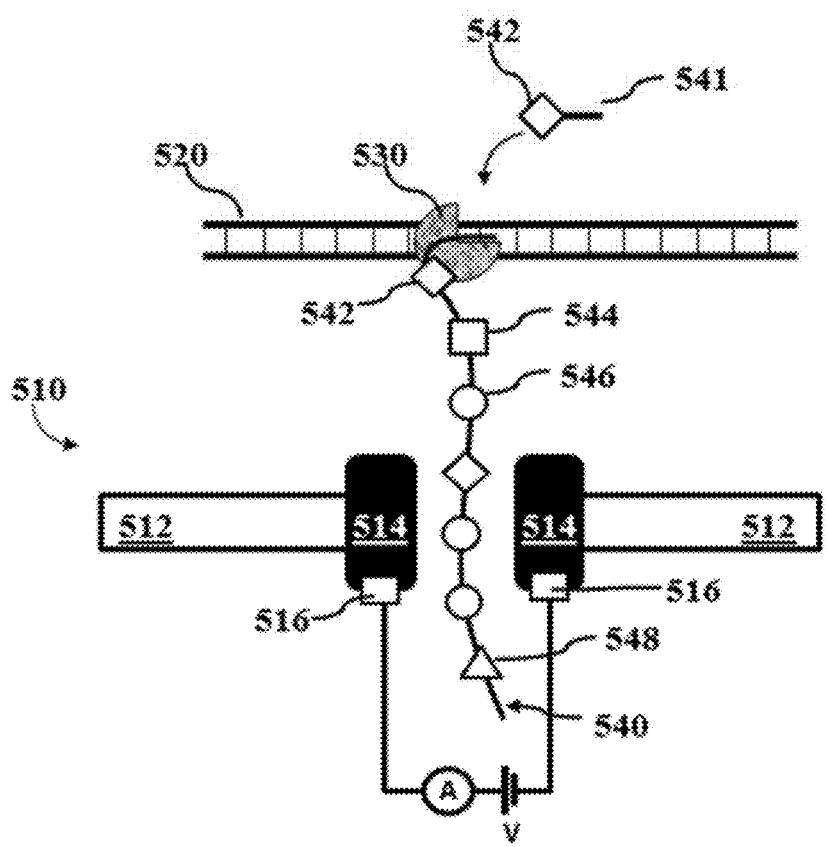
FIGS. 5A through 5D schematically illustrate example nanopore sequencing systems to obtain sequence information of one or more nucleic acid samples.

FIGS. 5A through 5D schematically illustrate example nanopore sequencing systems to obtain sequence information of one or more nucleic acid samples. Referring to FIG. 5A, the nanopore sequencing system 510 may comprise a membrane 512 comprising at least one nanopore 514 (a cross-section of the nanopore 514 is shown). The membrane 512 may be a lipid bilayer and/or a solid state membrane. The nanopore 514 may include a plurality of electrodes 516 configured to detect the one or more signals from the electrical circuit comprising the nanopore 514. The plurality of electrodes 516 may be disposed on one side of the membrane 512. The plurality of electrodes 516 may be coupled to the nanopore 514. The electrical circuit may further comprise an ammeter and a voltage source. A nucleic acid molecule 520 may be provided adjacent to the nanopore 514. By using the enzyme 530 (e.g., a polymerase), the nucleic acid molecule 520 may be brought in contact with a nucleotide 541 having a tag 542 under conditions sufficient to incorporate the nucleotide 541 into a nucleic acid strand 540 that is complementary to at least a portion of the nucleic acid molecule 520. Different types of nucleotides may have different tags, 542, 544, 546, 548, respectively, for example. Upon incorporation of the nucleotide 541 into the nucleic acid strand 540, at least a portion of the tag 542 may be disposed within the nanopore 514. One or more signals indicative of an impedance or impedance change in the nanopore 514 may be detected when at least a portion of the tag 542 is within the nanopore. The one or more signals may comprise an electrical current or change thereof. In this example, the tag 542 may be attached to the nucleic acid strand 540 when it is disposed within the nanopore 514. The one or more signals may be used to identify the nucleotide 541 incorporated into the nucleic acid strand 540.

Figure 5B:
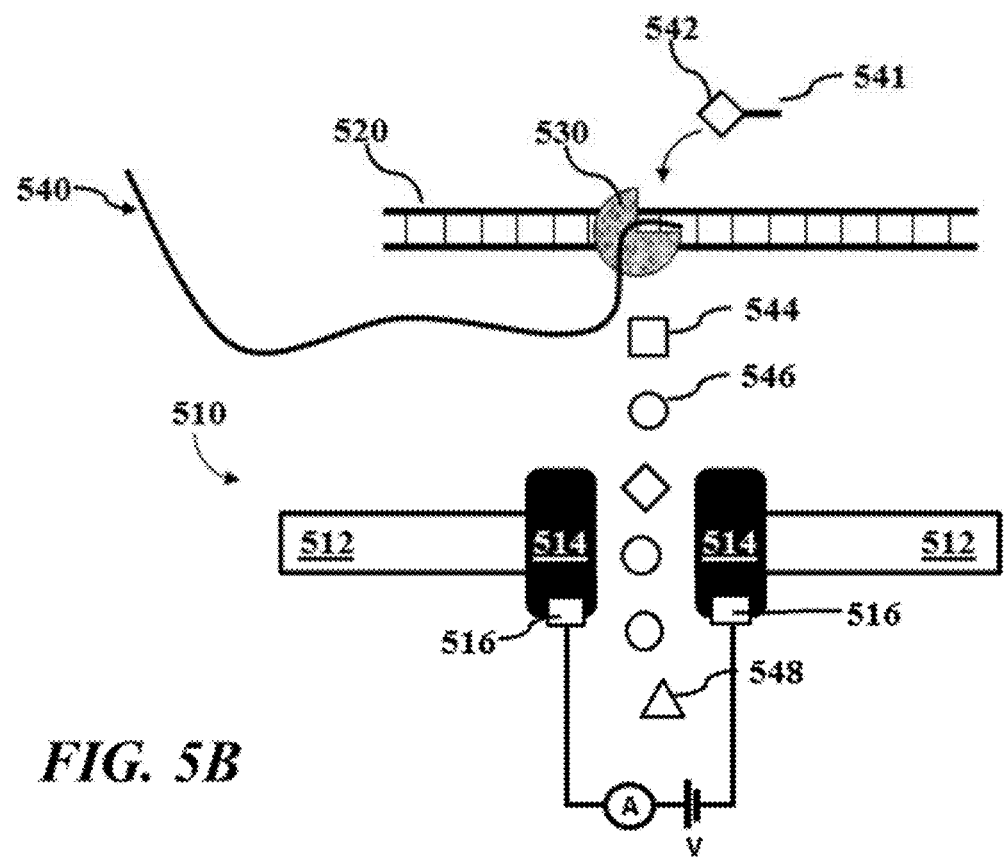

Referring to FIG. 5B, the nanopore sequencing system 510 may comprise a membrane 512 comprising at least one nanopore 514 (a cross-section of the nanopore 514 is shown). The membrane 512 may be a lipid bilayer and/or a solid state membrane. The nanopore 514 may include a plurality of electrodes 516 configured to detect the one or more signals from the electrical circuit comprising the nanopore 514. The plurality of electrodes 516 may be coupled to the nanopore 514. The electrical circuit may further comprise an ammeter and a voltage source. A nucleic acid molecule 520 may be provided adjacent to the nanopore 514. By using the enzyme 530 (e.g., a polymerase), the nucleic acid molecule 520 may be brought in contact with a nucleotide 541 having a tag 542 under conditions sufficient to incorporate the nucleotide 541 into a nucleic acid strand 540 that is complementary to at least a portion of the nucleic acid molecule 520. Different types of nucleotides may have different tags, 542, 544, 546, 548, respectively, for example. Upon incorporation of the nucleotide 541 into the nucleic acid strand 540, the tag 542 may be released from the nucleotide 541, and at least a portion of the released tag 542 may be disposed within the nanopore 514. One or more signals indicative of an impedance or impedance change in the nanopore 514 may be detected when at least a portion of the released tag 542 is within the nanopore. The one or more signals may be used to identify the nucleotide 541 incorporated into the nucleic acid strand 540.

Figure 5C:
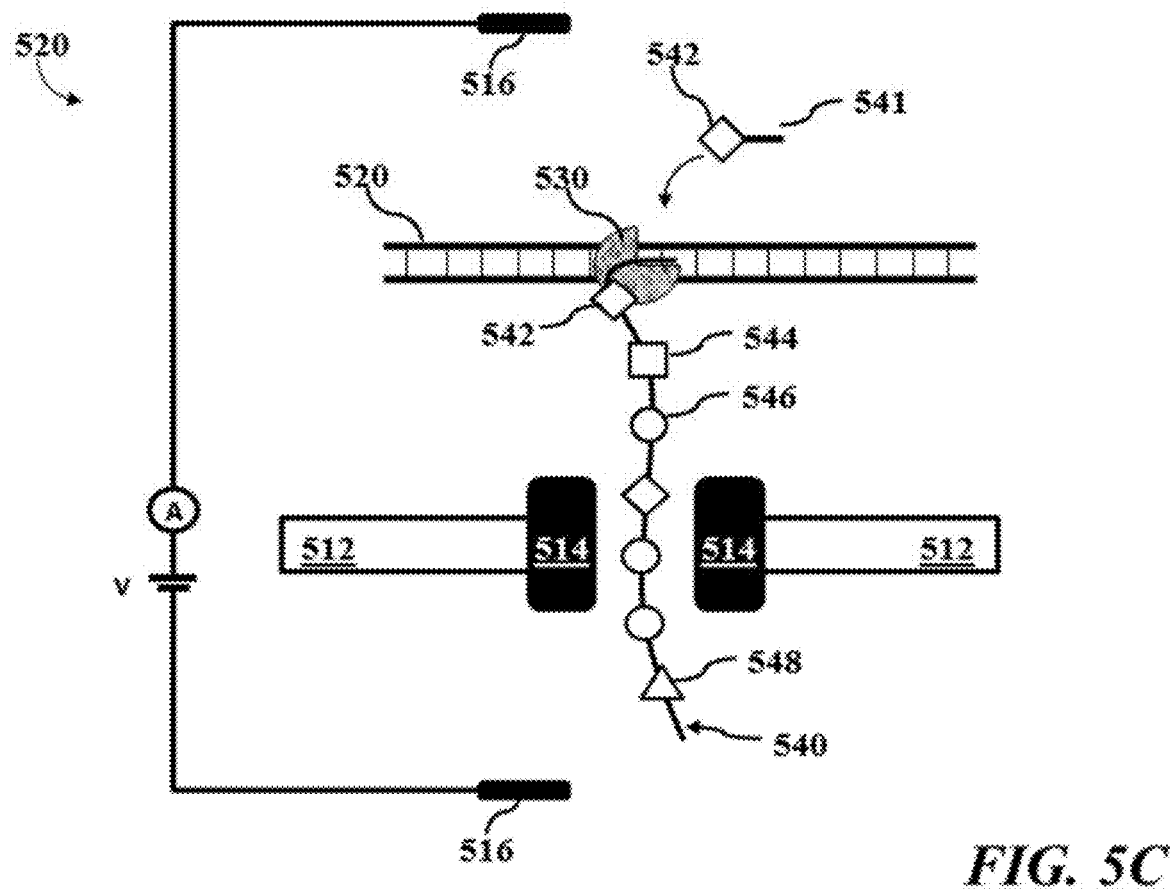

Referring to FIG. 5C, the nanopore sequencing system 510 may comprise a membrane 512 comprising at least one nanopore 514 (a cross-section of the nanopore 514 is shown). The membrane 512 may be a lipid bilayer and/or a solid state membrane. The nanopore 514 may be operatively coupled to a plurality of electrodes 516 configured to detect the one or more signals across the membrane 512 from the electrical circuit. The nanopore sequencing system 512 may be in an electrolytic solution. The electrical circuit may further comprise an ammeter and a voltage source. A nucleic acid molecule 520 may be provided adjacent to the nanopore 514. By using the enzyme 530 (e.g., a polymerase), the nucleic acid molecule 520 may be brought in contact with a nucleotide 541 having a tag 542 under conditions sufficient to incorporate the nucleotide 541 into a nucleic acid strand 540 that is complementary to at least a portion of the nucleic acid molecule 520. Different types of nucleotides may have different tags, 542, 544, 546, 548, respectively, for example. Upon incorporation of the nucleotide 541 into the nucleic acid strand 540, at least a portion of the tag 542 may be disposed within the nanopore 514. One or more signals indicative of an impedance or impedance change in the nanopore 514 may be detected when at least a portion of the tag 542 is within the nanopore. The one or more signals may comprise an electrical current or change thereof. In this example, the tag 542 may be attached to the nucleic acid strand 540 when it is disposed within the nanopore 514. The one or more signals may be used to identify the nucleotide 541 incorporated into the nucleic acid strand 540.

Figure 5D:
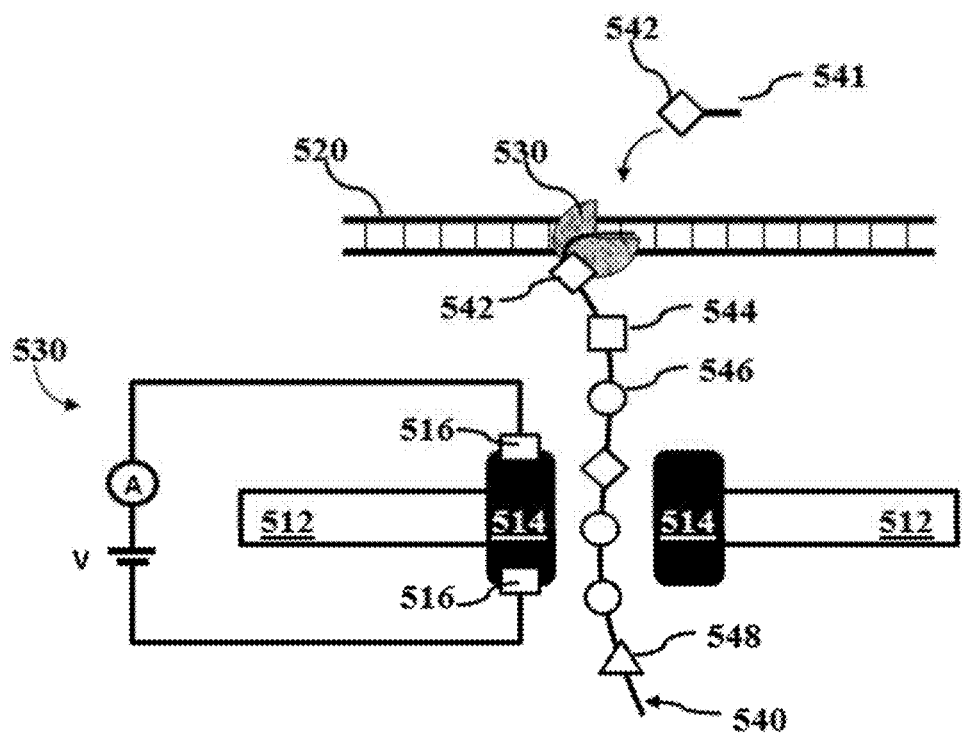

Referring to FIG. 5D, the nanopore sequencing system 510 may comprise a membrane 512 comprising at least one nanopore 514 (a cross-section of the nanopore 514 is shown). The membrane may be a lipid bilayer and/or a solid state membrane. The nanopore 514 may include a plurality of electrodes 516 configured to detect the one or more signals from the electrical circuit comprising the nanopore 514. The plurality of electrodes 516 may be disposed on opposite sides of the membrane 512. The plurality of electrodes 516 may be coupled to the nanopore 514. The electrical circuit may further comprise an ammeter and a voltage source. A nucleic acid molecule 520 may be provided adjacent to the nanopore 514. By using the enzyme 530 (e.g., a polymerase), the nucleic acid molecule 520 may be brought in contact with a nucleotide 541 having a tag 542 under conditions sufficient to incorporate the nucleotide 541 into a nucleic acid strand 540 that is complementary to at least a portion of the nucleic acid molecule 520. Different types of nucleotides may have different tags, 542, 544, 546, 548, respectively, for example. Upon incorporation of the nucleotide 541 into the nucleic acid strand 540, at least a portion of the tag 542 may be disposed within the nanopore 514. One or more signals indicative of an impedance or impedance change in the nanopore 514 may be detected when at least a portion of the tag 542 is within the nanopore. The one or more signals may comprise an electrical current or change thereof. In this example, the tag 542 may be attached to the nucleic acid strand 540 when it is disposed within the nanopore 514. The one or more signals may be used to identify the nucleotide 541 incorporated into the nucleic acid strand 540.

The nanopore 514 in the context of FIGS. 5A, 5B and 5D may be a solid state nanopore, such as, for example, a pore or passage directed through a solid state substrate. The nanopore in the context of FIG. 5C may be a pore protein, such as, for example, an alpha-hemolysin molecule, embedded in a lipid bilayer, for example.

Apparatus Overview

Methods and systems provided by the present disclosure can be performed and sequencing data acquired using any suitable sequencing apparatus such as an apparatus capable of performing large scale, parallel sequencing reactions. For example, a high-throughput sequencing system can be used.

Polynucleotide sequences can be analyzed, for example, to identify repeat unit length such as the monomer length)

the junction formed by circularization, and any true variation with respect to a reference sequence. Identifying a repeat unit length can include computing the regions of the repeated units, finding the reference loci of the sequences such as when one or more sequences are targeted for amplification, enrichment, and/or sequencing, the boundaries of each repeated region, and/or the number of repeats within each sequencing run. Sequence analysis can include analyzing sequence data for both strands of a duplex. For example, an identical variant that appears the sequences of reads from different polynucleotides from the sample such as circularized polynucleotides having different junctions can be considered a confirmed variant. A sequence variant can also be considered a genuine variant if it occurs in more than one repeated unit of the same polynucleotide, as the same sequence variation is likewise unlikely to occur at the same position in a repeated target sequence within the same concatemer. The quality score of a sequence may be considered in identifying variants and confirmed variants, for example, the sequence and bases with quality scores lower than a threshold may be filtered out. Other bioinformatics methods can be used to further increase the sensitivity and specificity of the variant calls.

A system for detecting a sequence variant provided by the present disclosure, for example, can comprise (a) a computer configured to receive a user request to perform a detection reaction on a sample; (b) a polynucleotide preparation system that performs a polynucleotide amplification reaction on the sample or a portion thereof in response to the user request, wherein the amplification reaction comprises the steps of (i) circularizing individual polynucleotides to form a plurality of circular polynucleotides, each of which having a junction between the 5' end and 3' end; and (ii) amplifying the circular polynucleotides, or alternatively, amplifying double stranded polynucleotides and circularizing the amplified double stranded polynucleotides; (iii) nicking a single strand of the circularized polynucleotides to provide a nicking site; (iv) coupling a polymerase to the nicking site to provide a polymerase/circular polynucleotide complex; (v) associating the polymerase/circular polynucleotide complex with a nanopore; and (c) a sequencing system that generates sequencing reads for the polynucleotides, identifies sequence differences between sequencing reads and a reference sequence, and calls a sequence difference that occurs in at least two circular polynucleotides having different junctions as the sequence variant; and (d) a report generator that sends a report to a recipient, wherein the report contains results for detection of the sequence variant. In some embodiments, the recipient is the user. In some cases, a sequencing apparatus can comprise an array of sensors for sequencing nucleic acids, e.g., an array of nanopores.

Each nanopore sequencing complex may be inserted in a membrane, e.g. a lipid bilayer, and disposed adjacent or in proximity to a sensing electrode of a sensing circuit, such as an integrated circuit of a nanopore based sensor. Multiple nanopore sensors may be provided as arrays, such as arrays present on a chip or biochip. The array of nanopores may have any suitable number of nanopores. The array may comprise about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, or more nanopores (or nanopore sequencing complexes).

During sequencing using one or more tagged nucleotides (or one or more tagged polynucleotides), the tagged nucleotides can be incorporated with an enzyme (e.g., a polymerase) of each nanopore sequencing complex. During polymerization, a tag can be detected by the nanopore such as by releasing and passing into or through the nanopore, or by being presented to the nanopore. A single tag can be released and/or presented upon incorporation of a single nucleotide and detected by a nanopore. A plurality of tags can be released and/or presented upon incorporation of a plurality of nucleotides. A nanopore sensor adjacent to a nanopore (or coupled to the nanopore) may detect an individual tag, or a plurality of tags. One or more signals associated with plurality of tags may be detected and processed to yield an averaged signal. Tags may be detected by the sensor as a function of time. Tags detected with time may be used to determine the nucleic acid sequence of the polynucleotide sample, such as with the aid of a computer system programmed to record sensor data and generate sequence information from the data.

Any apparatus and system suitable for sequencing by RCA and transcription can be used. In some cases, a sequencing system can generate sequencing reads for polynucleotides amplified by an amplification system, identify sequence differences between sequencing reads and a reference sequence, and call a sequence difference that occurs in at least two circular polynucleotides having different junctions as the sequence variant. The sequencing system and the amplification system may be the same, or comprise one or more overlapping equipment. In an example, both the amplification system and sequencing system may utilize the same thermocycler. A variety of sequencing platforms for use may be available, and may be selected based on the selected sequencing method. Amplification and sequencing may involve the use of liquid handlers. Several commercially available liquid handling systems can be utilized to run the automation of these processes.

A sequencing system can comprise, for example, a computer, computer-readable media comprising computer-executable code, storage devices, communications devices, control algorithms, analysis algorithms, and/or reporting algorithms.

The sequencing apparatus can be used for detecting a sequence variant. Detecting the sequence variant can comprise detecting mutations such as rare somatic mutations with respect to a reference sequence or in a background of no mutations, where the sequence variant is correlated with disease. Sequence variants for which there is statistical, biological, and/or functional evidence of association with a disease or trait are referred to as "causal genetic variants." A single causal genetic variant can be associated with more than one disease or trait. A causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification, for example, DNA methylation. A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease.

Nanopore Device

A sequencing system can include a reaction chamber that includes one or more nanopore devices. A nanopore device may be an individually addressable nanopore device. An individually addressable nanopore can be individually readable. An individually addressable nanopore can be individually writable. An individually addressable nanopore can be individually readable and individually writable. The system can include one or more computer processors for facilitating sample preparation and various operations of the disclosure, such as polynucleotide sequencing. The processor can be coupled to nanopore device.

A nanopore device may include a plurality of individually addressable sensing electrodes. Each sensing electrode can include a membrane adjacent to the electrode, and one or more nanopores in the membrane. A nanopore may be in a membrane such as a lipid bi-layer disposed adjacent or in sensing proximity to an electrode that is part of, or coupled to, an integrated circuit. A nanopore may be associated with an individual electrode and sensing integrated circuit or a plurality of electrodes and sensing integrated circuits. A nanopore can comprise a solid state nanopore.

Devices and systems for use in methods provided by the present disclosure may accurately detect individual nucleotide incorporation events, such as upon the incorporation of a nucleotide into a growing strand that is complementary to a template. An enzyme such as a DNA polymerase, RNA polymerase, or ligase can incorporate nucleotides to a growing polynucleotide chain. Enzymes such as polymerases can generate polynucleotide strands.

The added nucleotide can be complimentary to the corresponding template polynucleotide strand which is hybridized to the growing strand. A nucleotide can include a tag or tag species that is coupled to any location of the nucleotide including, but not limited to a phosphate such as a γ-phosphate, sugar or nitrogenous base moiety of the nucleotide. In some cases, tags are detected while tags are associated with a polymerase during the incorporation of nucleotide tags. The tag may continue to be detected until the tag translocates through the nanopore after nucleotide incorporation and subsequent cleavage and/or release of the tag. Nucleotide incorporation events can release tags from the nucleotides which pass through a nanopore and are detected. A tag can be released by the polymerase, or cleaved/released in any suitable manner including without limitation cleavage by an enzyme located near the polymerase. In this way, the incorporated base may be identified (i.e., A, C, G, T or U) because a unique tag is released from each type of nucleotide (i.e., adenine, cytosine, guanine, thymine or uracil). In nucleotide incorporation events that do not release, a tag coupled to an incorporated nucleotide is detected with the aid of a nanopore. In some examples, the tag can move through or in proximity to the nanopore and be detected with the aid of the nanopore.

Methods and systems of the disclosure can enable the detection of polynucleotide incorporation events, such as at a resolution of at least 1, 2, 3, 4, 5, 6, 7, 8, 9, 10, 20, 30, 40, 50, 100, 500, 1000, 5000, 10000, 50000, or 100000 polynucleotide bases within a given time period. For example, a nanopore device can be used to detect individual polynucleotide incorporation events, with each event being associated with an individual nucleic acid base. In other examples, a nanopore device can be used to detect an event that is associated with a plurality of bases. For example, a signal sensed by the nanopore device can be a combined signal from at least 2, 3, 4, or 5 bases.

In certain sequencing methods, tags do not pass through the nanopore. The tags can be detected by the nanopore and exit the nanopore without passing through the nanopore such as exiting from the inverse direction from which the tag entered the nanopore. A sequencing device can be configured to actively expel the tags from the nanopore.

In certain sequencing methods tags are not released upon nucleotide incorporation events. Nucleotide incorporation events can present tags to a nanopore without releasing the tags. The tags can be detected by the nanopore without being released. The tags may be attached to the nucleotides by a linker of sufficient length to present the tag to the nanopore for detection.

Nucleotide incorporation events may be detected in real-time as they occur by a nanopore. An enzyme such as a DNA polymerase attached to or in proximity to a nanopore can facilitate the flow of a polynucleotide through or adjacent to a nanopore. A nucleotide incorporation event, or the incorporation of a plurality of nucleotides, may release or present one or more tags, which may be detected by a nanopore. Detection can occur as the tags flow through or adjacent to the nanopore, as the tags reside in the nanopore and/or as the tags are presented to the nanopore. In some cases, an enzyme attached to or in proximity to the nanopore may aid in detecting tags upon the incorporation of one or more nucleotides.

A tag can be an atom, a molecule, a collection of atoms, or a collection of molecules. A tag may provide an optical, electrochemical, magnetic, or electrostatic such as an inductive or capacitive, signature, which signature may be detected with the aid of a nanopore.

The nanopore may be formed or otherwise embedded in a membrane disposed adjacent to a sensing electrode of a sensing circuit, such as an integrated circuit. An integrated circuit may be an application specific integrated circuit (ASIC). An integrated circuit can be a field effect transistor or a complementary metal-oxide semiconductor (CMOS). A sensing circuit may be situated in a chip or other device having the nanopore, or off of the chip or device, such as in an off-chip configuration.

As a nucleic acid or tag flows through or adjacent to the nanopore, the sensing circuit detects an electrical signal associated with the nucleic acid or tag. The nucleic acid may be a subunit of a larger strand. The tag may be a byproduct of a nucleotide incorporation event or other interaction between a tagged nucleic acid and the nanopore or a species adjacent to the nanopore, such as an enzyme that cleaves a tag from a nucleic acid. The tag may remain attached to the nucleotide. A detected signal may be collected and stored in a memory location, and later used to construct a sequence of the nucleic acid. The collected signal may be processed to account for any abnormalities in the detected signal, such as errors.

Nanopores may be used to sequence polynucleotides indirectly, in some cases with electrical detection. Indirect sequencing may be any method where an incorporated nucleotide in a growing strand does not pass through the nanopore. The polynucleotide may pass within any suitable distance from and/or proximity to the nanopore, in some cases within a distance such that tags released from nucleotide incorporation events are detected in the nanopore.

Byproducts of nucleotide incorporation events may be detected by the nanopore. Nucleotide incorporation events refer to the incorporation of a nucleotide into a growing polynucleotide chain. A byproduct may be correlated with the incorporation of a given type nucleotide. Nucleotide incorporation events can be catalyzed by an enzyme, such as DNA polymerase, and use base pair interactions with a template molecule to choose amongst the available nucleotides for incorporation at each location.

A nucleic acid sample may be sequenced using tagged nucleotides or nucleotide analogs. In some examples, a method for sequencing a nucleic acid molecule comprises (a) incorporating (e.g., polymerizing) tagged nucleotides, wherein a tag associated with an individual nucleotide is released upon incorporation, and (b) detecting the released tag with the aid of a nanopore. In some instances, the method further comprises directing the tag attached to or released from an individual nucleotide through the nanopore. The released or attached tag may be directed by any suitable technique, in some cases with the aid of an enzyme (or molecular motor) and/or a voltage difference across the pore. Alternative, the released or attached tag may be directed through the nanopore without the use of an enzyme. For example, the tag may be directed by a voltage difference across the nanopore as described herein.

A tag may be detected with the aid of a nanopore device having at least one nanopore in a membrane. The tag may be associated with an individual tagged nucleotide during incorporation of the individual tagged nucleotide. A nanopore device can detect a tag associated with an individual tagged nucleotide during incorporation. The tagged nucleotides, whether incorporated into a growing nucleic acid strand or unincorporated, can be detected, determined, or differentiated for a given period of time by the nanopore device, in some cases with the aid of an electrode and/or nanopore of the nanopore device. The time period within which the nanopore device detects the tag may be shorter, in some cases substantially shorter, than the time period in which the tag and/or nucleotide coupled to the tag is held by an enzyme, such as an enzyme facilitating the incorporation of the nucleotide into a nucleic acid strand (e.g., a polymerase). A tag can be detected by the electrode a plurality of times within the time period that the incorporated tagged nucleotide is associated with the enzyme. For instance, the tag can be detected by the electrode at least 1, 2, 3, 4, 5, 6, 7, 8, 9, 10, 20, 30, 40, 50, 60, 70, 80, 90, 100, 200, 300, 400, 500, 1000, 10,000, 100,000, or 1,000,000 times within the time period that the incorporated tagged nucleotide is associated with the enzyme.

Sequencing can be accomplished using pre-loaded tags. Pre-loading a tag can comprise directing at least a portion of the tag through at least a portion of a nanopore while the tag can be attached to a nucleotide, which nucleotide has been incorporated into a nucleic acid strand (e.g., growing nucleic acid strand), is undergoing incorporation into the nucleic acid strand, or has not yet been incorporated into the nucleic acid strand but may undergo incorporation into the nucleic acid strand. Pre-loading a tag can comprise directing at least a portion of the tag through at least a portion of the nanopore before the nucleotide has been incorporated into the nucleic acid strand or while the nucleotide is being incorporated into the nucleic acid strand. Pre-loading a tag can include directing at least a portion of the tag through at least a portion of the nanopore after the nucleotide has been incorporated into the nucleic acid strand.

A tag associated with an individual nucleotide can be detected by a nanopore without being released from the nucleotide upon incorporation. Tags can be detected without being released from incorporated nucleotides during synthesis of a nucleic acid strand that is complementary to a target strand. The tags can be attached to the nucleotides with a linker such that the tag is presented to the nanopore (e.g., the tag hangs down into or otherwise extend through at least a portion of the nanopore). The length of the linker may be sufficiently long so as to permit the tag to extend to or through at least a portion of the nanopore. In some instances, the tag is presented to (i.e., moved into) the nanopore by a voltage difference. Other ways to present the tag into the pore may also be suitable (e.g., use of enzymes, magnets, electric fields, pressure differential). In some instances, no active force is applied to the tag (i.e., the tag diffuses into the nanopore).

A chip for sequencing a nucleic acid sample can comprise a plurality of individually addressable nanopores. An individually addressable nanopore of the plurality can contain at least one nanopore formed in a membrane disposed adjacent to an integrated circuit. Each individually addressable nanopore can be capable of detecting a tag associated with an individual nucleotide. The nucleotide can be incorporated (e.g., polymerized) and the tag may not be released from the nucleotide upon incorporation.

Tags can be presented to the nanopore upon nucleotide incorporation events and are released from the nucleotide. The released tags can go through the nanopore. The tags do not pass through the nanopore in some instances. A tag that has been released upon a nucleotide incorporation event is distinguished from a tag that may flow through the nanopore, but has not been released upon a nucleotide incorporation event at least in part by the dwell time in the nanopore. In some cases, tags that dwell in the nanopore for at least 100 milliseconds (ms) are released upon nucleotide incorporation events and tags that dwell in the nanopore for less than 100 ms are not released upon nucleotide incorporation events. Tags may be captured and/or guided through the nanopore by a second enzyme or protein (e.g., a nucleic acid binding protein). The second enzyme may cleave a tag upon (e.g., during or after) nucleotide incorporation. A linker between the tag and the nucleotide may be cleaved.

A tag that is coupled to an incorporated nucleotide is distinguished from a tag associated with a nucleotide that has not been incorporated into a growing complementary strand based on the residence time of the tag in the nanopore or a signal detected from the unincorporated nucleotide with the aid of the nanopore. An unincorporated nucleotide may generate a signal (e.g., voltage difference, current) that is detectable for a time period between 1 nanosecond (ns) and 100 ms, or between 1 ns and 50 ms, whereas an incorporated nucleotide may generate a signal with a lifetime between 50 ms and 500 ms, or 100 ms and 200 ms. An unincorporated nucleotide may generate a signal that is detectable for a time period between 1 ns and 10 ms, or 1 ns and 1 ms. An unincorporated tag is detectable by a nanopore for a time period (average) that is longer than the time period in which an incorporated tag is detectable by the nanopore.

Incorporated nucleic acids can be detected by and/or are detectable by the nanopore for a shorter period of time than an un-incorporated nucleotide. Alternatively, incorporated nucleic acids can be detected by and/or are detectable by the nanopore for a longer period of time than an un-incorporated nucleotide. The difference and/or ratio between these times can be used to determine whether a nucleotide detected by the nanopore is incorporated or not, as described herein.

The detection period can be based on the free-flow of the nucleotide through the nanopore; an unincorporated nucleotide may dwell at or in proximity to the nanopore for a time period between 1 nanosecond (ns) and 100 ms, or between 1 ns and 50 ms, whereas an incorporated nucleotide may dwell at or in proximity to the nanopore for a time between 50 ms and 500 ms, or 100 ms and 200 ms. The time periods can vary based on processing conditions; however, an incorporated nucleotide may have a dwell time that is greater than that of an unincorporated nucleotide.

A tag or tag species can include a detectable atom or molecule, or a plurality of detectable atoms or molecules. A tag can include a one or more adenine, guanine, cytosine, thymine, uracil, or a derivative thereof linked to any position including a phosphate group, sugar or a nitrogenous base of a nucleic acid molecule. A tag can include one or more adenine, guanine, cytosine, thymine, uracil, or a derivative thereof covalently linked to a phosphate group of a nucleic acid base.

A tag can have a length of at least 0.1 nanometers (nm), 1 nm, 2 nm, 3 nm, 4, nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, or 1000 nm.

A tag can include a tail of repeating subunits, such as a plurality of adenine, guanine, cytosine, thymine, uracil, or a derivative thereof. For example, a tag can include a tail portion having at least 2, 3, 4, 5, 6, 7, 8, 9, 10, 20, 30, 40, 50, 60, 70, 80, 90, 100, 1000, 10,000, or 100,000 subunits of adenine, guanine, cytosine, thymine, uracil, or a derivative thereof. The subunits can be linked to one another, and at a terminal end linked to a phosphate group of the nucleic acid. Other examples of tag portions include any polymeric material, such as polyethylene glycol (PEG), polysulfonates, amino acids, or any completely or partially positively charged, negatively charged, or un-charged polymer.

Polymerase

A DNA polymerase can be bound to the 3' end of a nicked strand of the polynucleotide at the nicking site. DNA sequencing can be accomplished by using an enzyme such as a DNA polymerize to amplify and transcribe a polynucleotide in proximity to a nanopore and tagged nucleotides. Sequencing methods can involve incorporating or polymerizing tagged nucleotides using a polymerase such as a DNA polymerase, or transcriptase. The polymerase can be mutated to allow it to accept tagged nucleotides. The polymerase can also be mutated to increase the time for which the tag is detected by the nanopore.

A sequencing enzyme can be, for example, any suitable enzyme that creates a polynucleotide strand by phosphate linkage of nucleotides. The DNA polymerase can be, for example, a 9° Nm™ polymerase or a variant thereof, an E. Coli DNA polymerase I, a Bacteriophage T4 DNA polymerase, a Sequenase, a Taq DNA polymerase, a 9° Nm™ polymerase (exo-)A485L/Y409V, a φ29 DNA Polymerase, a Bst DNA polymerase, or variants, mutants, or homologs of any of the foregoing. A homolog can have any suitable percentage homology such as, for example, at least 30%, at least 40%, at least 50%, at least 60%, at least 70%, at least 80%, at least 90%, or at least 95% sequence identity.

In some examples, for nanopore sequencing, a polymerization enzyme can be attached to or situated in proximity to a nanopore. Suitable methods for attaching the polymerization enzyme to a nanopore include cross-linking the enzyme to the nanopore or in proximity to the nanopore such as via the formation of intra-molecular disulfide bonds. The nanopore and the enzyme may also be a fusion such as an encoded by a single polypeptide chain. Methods for producing fusion proteins may include fusing the coding sequence for the enzyme in frame and adjacent to the coding sequence for the nanopore and expressing this fusion sequence from a single promoter. A polymerization enzyme can be attached or coupled to a nanopore using molecular staples or protein fingers. A polymerization enzyme can be attached to a nanopore via an intermediate molecule, such as for example biotin conjugated to both the enzyme and the nanopore with streptavidin tetramers linked to both biotins. The intermediate molecule can be referred to as a linker.

The sequencing enzyme can also be attached to a nanopore with an antibody. Proteins that form a covalent bond between each other can be used to attach a polymerase to a nanopore. Phosphatase enzymes or an enzyme that cleaves a tag from a nucleotide can also be attached to the nanopore.

The polymerase can be mutated to facilitate and/or to improve the efficiency of the mutated polymerase for incorporation of tagged nucleotides into a growing polynucleotide relative to the non-mutated polymerase. The polymerase can be mutated to improve entry of the nucleotide analog such as a tagged nucleotide, into the active site region of the polymerase and/or mutated for coordinating with the nucleotide analogs in the active region.

Other mutations such as amino acid substitutions, insertions, deletions, and/or exogenous features to a polymerize can result in enhanced metal ion coordination, reduced exonuclease activity, reduced reaction rates at one or more steps of the polymerase kinetic cycle, decreased branching fraction, altered cofactor selectivity, increased yield, increased thermostability, increased accuracy, increased speed, increased read length, increased salt tolerance relative to the non-mutated polymerase.

A suitable polymerase can have a kinetic rate profile that is suitable for detection of the tags by a nanopore. The rate profile generally refers to the overall rate of nucleotide incorporation and/or a rate of any step of nucleotide incorporation such as nucleotide addition, enzymatic isomerization such as to or from a closed state, cofactor binding or release, product release, incorporation of polynucleotide into the growing polynucleotide, or translocation.

A polymerase can be adapted to permit the detection of sequencing events. The rate profile of a polymerase can be such that a tag is loaded into (and/or detected by) the nanopore for an average of 0.1 milliseconds (ms), 1 ms, 5 ms 10 ms, 20 ms, 30 ms, 40 ms, 50 ms, 60 ms, 80 ms, 100 ms, 120 ms, 140 ms, 160 ms, 180 ms, 200 ms, 220 ms, 240 ms, 260 ms, 280 ms, 300 ms, 400 ms, 500 ms, 600 ms, 800 ms, or 1000 ms. For example, the rate profile of a polymerase can be such that a tag is loaded into and/or detected by the nanopore for an average of at least 5 ms, at least 10 ms, at least 20 ms, at least 30 ms, at least 40 ms, at least 50 ms, at least 60 ms, at least 80 ms, at least 100 ms, at least 120 ms, at least 140 ms, at least 160 ms, at least 180 ms, at least 200 ms, at least 220 ms, at least 240 ms, at least 260 ms, at least 280 ms, at least 300 ms, at least 400 ms, at least 500 ms, at least 600 ms, at least 800 ms, or at least 1000 ms. A tag can be detected by the nanopore for an average between 80 ms and 260 ms, between 100 ms and 200 ms, or between 100 ms and 150 ms.

A nanopore/polymerase complex can be configured to permit the detection of one or more events associated with amplification and transcription of the circular polynucleotide. The one or more events may be kinetically observable and/or non-kinetically observable such as a nucleotide migrating through a nanopore without coming in contact with a polymerase.

In some cases, the polymerase reaction exhibits two kinetic steps which proceed from an intermediate in which a nucleotide or a polyphosphate product is bound to the polymerase enzyme, and two kinetic steps which proceed from an intermediate in which the nucleotide and the polyphosphate product are not bound to the polymerase enzyme. The two kinetic steps can include enzyme isomerization, nucleotide incorporation, and product release. In some cases, the two kinetic steps are template translocation and nucleotide binding.

A suitable polymerase can exhibit strong or enhanced strand displacement.

Linker

A polymerase can comprise a linker. A linker can serve to couple the polymerase to a nanopore. A polymerase comprising a linker can be bound to a protein nanopore and thereby form a polymerase/nanopore complex, which can be bound to a nicking site of a circular polynucleotide.

A polymerase comprising a linker can be reacted with a nicked circular polynucleotide to form a polymerase/circular polynucleotide complex. A polymerase/circular polynucleotide complex can be bound via the linker to a nanopore such as a protein nanopore such as alpha-hemolysin or a solid state nanopore.

The polymerase/circular polynucleotide/nanopore complex can be used for polynucleotide sequencing. The nature of the link between the DNA polymerase and the nanopore can increase effective tagged nucleotide concentration, thereby lowering the entropic barrier. Examples of aspects of the linker that can be optimized are the length of the connection, which can increase effective tagged nucleotide concentration, affect the kinetics of capture, and/or change the entropic barrier); the connection flexibility, which can influence the kinetics of the connector conformational changes; and the number and location of the connections between the polymerase and the nanopore, which can reduce the number of available conformational states, thereby increasing the likelihood of proper pore-polymerase orientation, increase effective tagged nucleotide concentration and reduce the entropic barrier.

A linker can be a polymer such as a polypeptide, a polynucleotide, or polyethylene glycol. A linker can be any suitable length. For example, a linker can be 5 nm, 10 nm, 15 nm, 20 nm, 40 nm, 50 nm, or 100 nm long. A linker can be at least 5 nm, at least 10 nm, at least 15 nm, at least 20 nm, at least 40 nm, at least 50 nm, or at least 100 nm long. A linker can be less than 5 nm, less than 10 nm, less than 15 nm, less than 20 nm, less than 40 nm, less than 50 nm, or less than 100 nm long. A linker can be rigid, flexible, or a combination thereof.

In some embodiments, no linker is used and the polymerase is attached directly to the nanopore.

A polymerase can be attached to a nanopore by two or more linkers. The number and location of the connection between a polymerase and a nanopore can be varied. Examples include the αHL C-terminus to polymerase N-terminus, the αHL N-terminus to polymerase C-terminus, and the connections between amino acids not at the terminus.

A linker can serve to orient a polymerase with respect to the nanopore such that a tag can be detected with the aid of the nanopore.

For example, in a method for sequencing a polynucleotide sample with the aid of a nanopore in a membrane adjacent to a sensing electrode comprises providing tagged nucleotides into a reaction chamber comprising the nanopore, where an individual tagged nucleotide of the tagged nucleotides contains a tag coupled to a nucleotide that is detectable with the aid of the nanopore. The method can include carrying out a polymerization reaction with the aid of a polymerase attached by a linker to the nanopore, thereby incorporating an individual tagged nucleotide of the tagged nucleotides into a growing strand complementary to a single stranded polynucleotide from the polynucleotide sample. The method can include detecting, with the aid of the nanopore, a tag associated with the individual tagged nucleotide during incorporation of the individual tagged nucleotide, where the tag is detected with the aid of the nanopore when the nucleotide is associated with the polymerase.

Amplification and Sequencing

Amplification and transcription can comprise rolling circle amplification (RCA).

In RCA, the reaction mixture can comprise one or more primers, a polymerase, and dNTPs, and produces concatemers. A polymerase in an RCA reaction can comprise a polymerase having strand-displacement activity. Examples of polymerases having strand displacement activity include exonuclease minus DNA Polymerase I large (Klenow) Fragment, Phi29 DNA polymerase, and Taq DNA Polymerase.

In the process of sequencing while amplification, to prevent DNA polymerase binding from original template to displaced single strand DNA, single strand cleaving enzyme (e.g., exonuclease VIII truncated, T5 exonuclease, T7 exonuclease) may be used to cleave displaced single strand DNA to dNMP, dinucleotides, etc.

In some cases, the amplified polynucleotides can be visualized as nanoballs under fluorescent microscope or by particle size analysis.

Identification of Sequence Variants

Methods provided by the present disclosure can be used to identify sequence variants in a polynucleotide sample. A sequence difference between sequencing reads and a reference sequence is referred to as a genuine sequence variant if the sequence difference occurs in at least two different polynucleotides, e.g., two different circular polynucleotides, which can be distinguished as a result of having different junctions. Because the position and type of a sequence variant that are the result of amplification or sequencing errors are unlikely to be duplicated exactly on two different polynucleotides comprising the same target sequence, including this validation parameter can reduce the background of erroneous sequence variants, with a concurrent increase in the sensitivity and accuracy of detecting actual sequence variation in a sample. A sequence variant can have a frequency less than 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower is sufficiently above background to permit an accurate identification. A sequence variant can occur with a frequency of less than 0.1%. The frequency of a sequence variant can be sufficiently above background when such frequency is statistically significantly above the background error rate, for example, with a p-value less than 0.05, 0.01, 0.001, or 0.0001. The frequency of a sequence variant can be sufficiently above background when the frequency is at least 2-fold, 3-fold, 4-fold, 5-fold, 6-fold, 7-fold, 8-fold, 9-fold, 10-fold, 25-fold, 50-fold, 100-fold, or more above the background error rate. The background error rate for accurately determining the sequence at a given position can be less than 1%, 0.5%, 0.1%, 0.05%, 0.01%, 0.005%, 0.001%, or 0.0005%.

Identifying a sequence variant can comprise optimally aligning one or more sequencing reads with a reference sequence to identify differences between the two, as well as to identify junctions. Alignment can involve placing one sequence along another sequence, iteratively introducing gaps along each sequence, scoring how well the two sequences match, and repeating for various positions along the reference. The best-scoring match is deemed to be the alignment and represents an inference about the degree of relationship between the sequences.

A reference sequence to which sequencing reads are compared is a reference genome, such as the genome of a member of the same species as the subject. A reference genome may be complete or incomplete. A reference genome can consist only of regions containing target polynucleotides, such as from a reference genome or from a consensus generated from sequencing reads under analysis. A reference sequence can comprise or can consist of sequences of polynucleotides of one or more organisms, such as sequences from one or more bacteria, archaea, viruses, protists, fungi, or other organism. A reference sequence can consist of only a portion of a reference genome, such as regions corresponding to one or more target sequences under analysis. For example, for detection of a pathogen, a reference genome can be the entire genome of the pathogen, or a portion thereof useful in identification, such as of a particular strain or serotype. A sequencing read can be aligned to multiple different reference sequences, such as to screen for multiple different organisms or strains.

Computer Systems

The present disclosure provides computer systems that are programmed to implement one or more methods of the present disclosure. Computer systems of the present disclosure may be used to regulate various operations of nanopore sequencing, such as detecting one or more signals indicative of an impedance or impedance change in a nanopore when a sample (e.g., at least a portion of a tag of a tagged nucleotide) is within the nanopore (e.g., a protein nanopore or a solid state nanopore.

Figure 6:
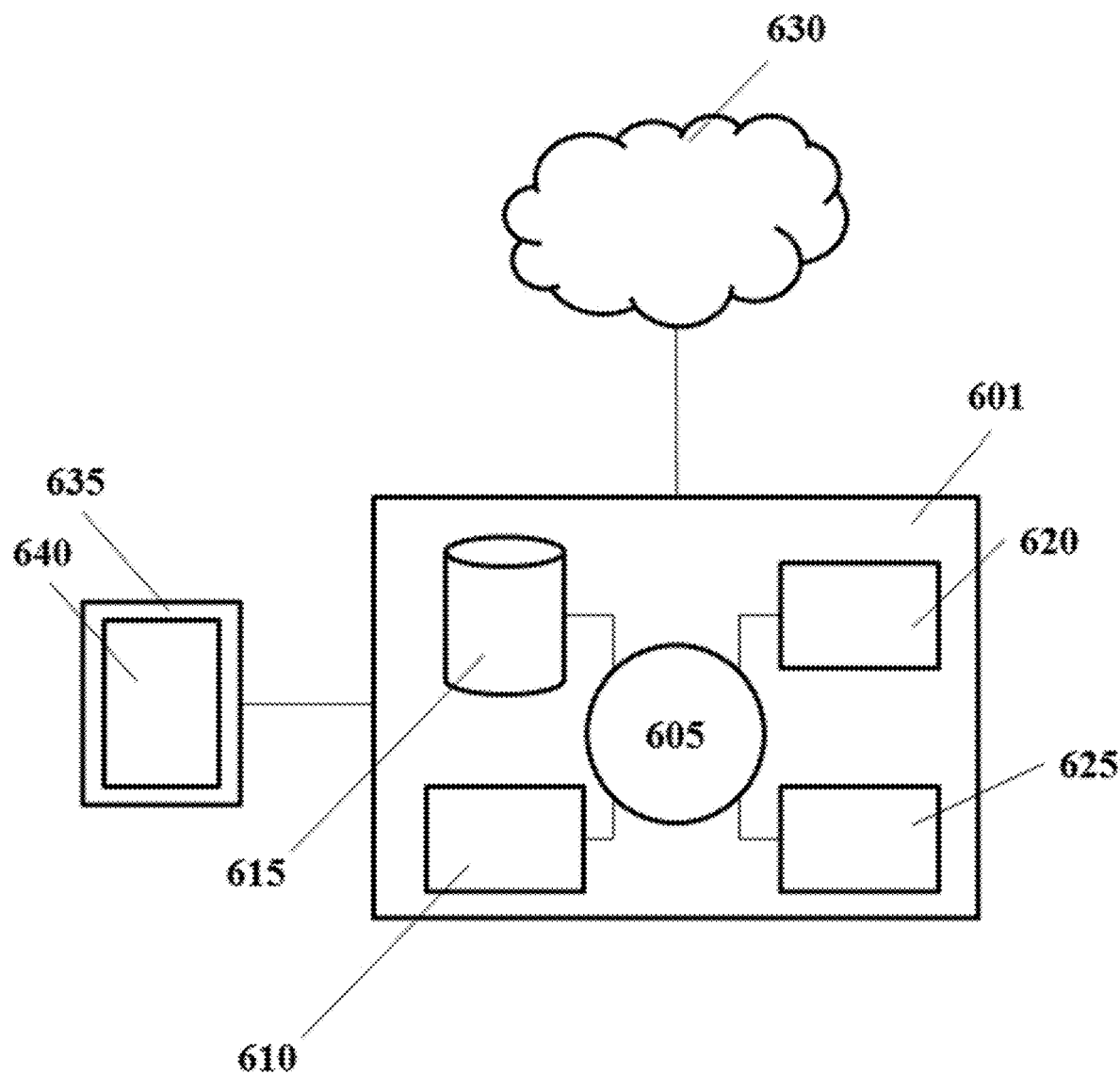
FIG. 6 shows a computer system that is programmed or otherwise configured to implement methods provided herein.

FIG. 6 shows a computer system 601 that is programmed or otherwise configured to communicate with and regulate various aspects of sequencing of the present disclosure. The computer system 601 can communicate with, for example, one or more circuitry coupled to or comprising a nanopore (or a membrane comprising the nanopore), and one or more devices (e.g., machines) used to prepare, treat, or keep one or more reaction mixtures for sequencing. The computer system 601 may also communicate with one or more controllers or processors of the present disclosure. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

=Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, (i) progress of the reaction mixture, (ii) progress of sequencing, and (iii) sequencing information obtained from sequencing. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, determine sequence readout of one or more target sites (e.g., one or more target mutation sites) upon nanopore sequencing.

EXAMPLES

Various aspects of the disclosure are further illustrated by the following non-limiting examples.

Example 1: Circularizing Single-Stranded Nucleic Acids

Figure 7B:
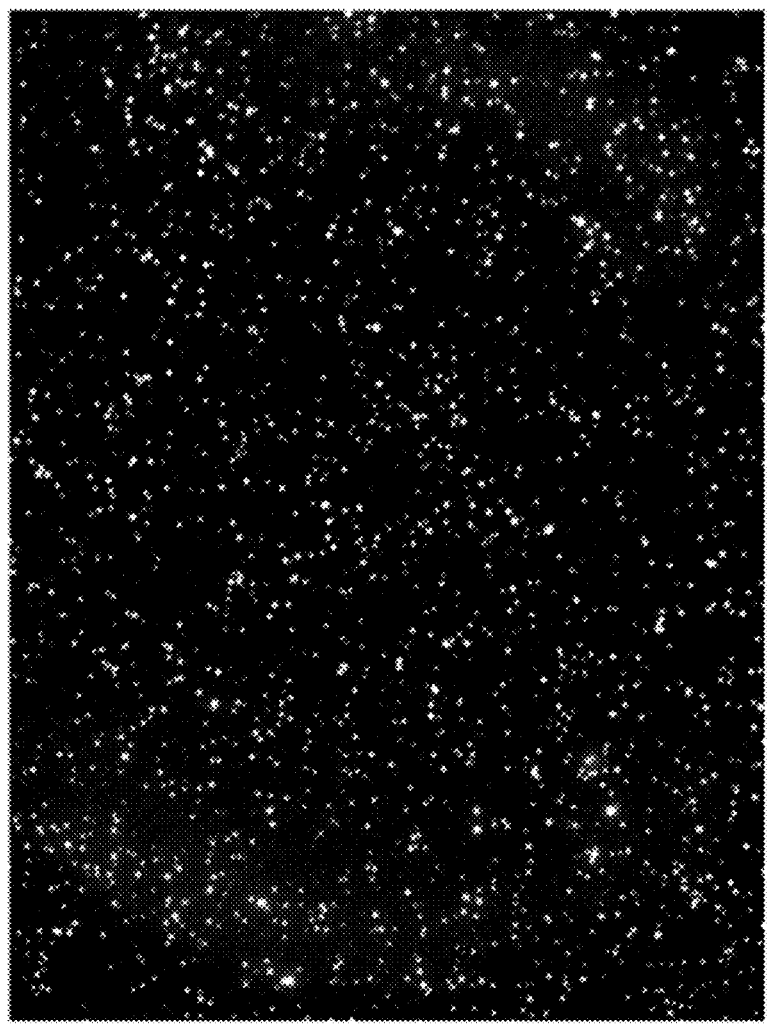
FIG. 7B shows an example a fluorescent image of RCA products from circularized single-stranded nucleic acids.
Figure 7A:
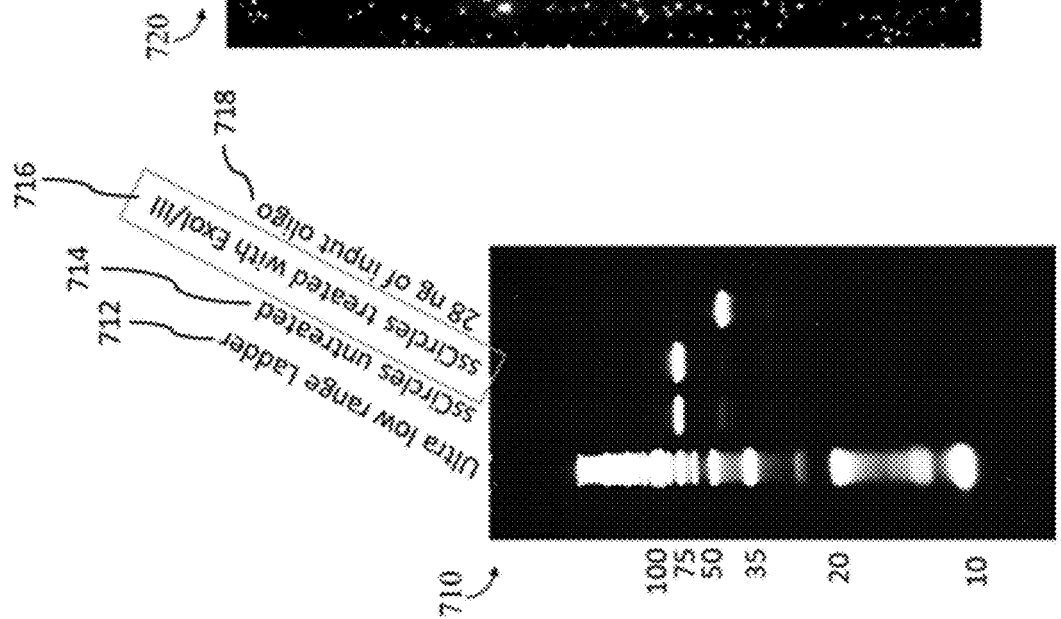
FIG. 7A shows an example of a gel electrophoresis image of a sample comprising a plurality of circularized single-stranded nucleic acids.

FIG. 7A shows an example gel electrophoresis image of a sample comprising a plurality of circularized single-stranded nucleic acids. A circular single-stranded circular DNA (circular ssDNA) may be generated from a biological sample or, alternatively, may be synthesized. A linear ssDNA may be circularized into the circular ssDNA via self-ligation, e.g., without use of an adaptor. The circular ssDNA may be used as a template to generate (e.g., via RCA by using a polymerase) into one or more DNA nanorolls (DNRs). Each DNR may comprise an polymerized nucleic acid strand comprising at least one copy of at least a portion of the circular ssDNA. In this example, a 59-nucleotide circular ssDNA template may be generated by DNA ligase. Examples of the DNA ligase may include T4 DNA ligase, T7 DNA ligase, Taq DNA ligase, SprintR ligase, CircLigase, etc. The efficiency may be obtained by comparing a starting amount of the linear ssDNA to a final amount of the circular ssDNA after (i) the circularization process and (ii) exonuclease depletion of any excess non-circularized single-stranded linear DNA. The starting material 714 (circularized, untreated with exonucleases), the product 716 (circularized, treated with exonucleases), control ladder 712, and oligonucleotide primer 718 may be resolved in 15% polyacrylamide gel electrophoresis 710 and stained with SYBR Green for the visualization. FIG. 7B shows an example a fluorescent image 720 of RCA products from circularized single-stranded nucleic acids. A polymerase (e.g., Phi29 polymerase) may be used to generate a plurality of DNRs from a plurality of the circular ssDNA in about 40 min RCA process.

An example of the linear ssDNA: 5'Phosphorylation-ATTTTAGCCCTGGAACCTTCAGAGAGTACGACGA-TATATGGGAACAACTGCTACCTGCT-3'

An example of the oligonucleotide primer sequence: 5'-AGCAGGTAGCAGTTGTTCCCAT-3'

Example 2: Circularizing Double-Stranded Nucleic Acids

Figure 7D:
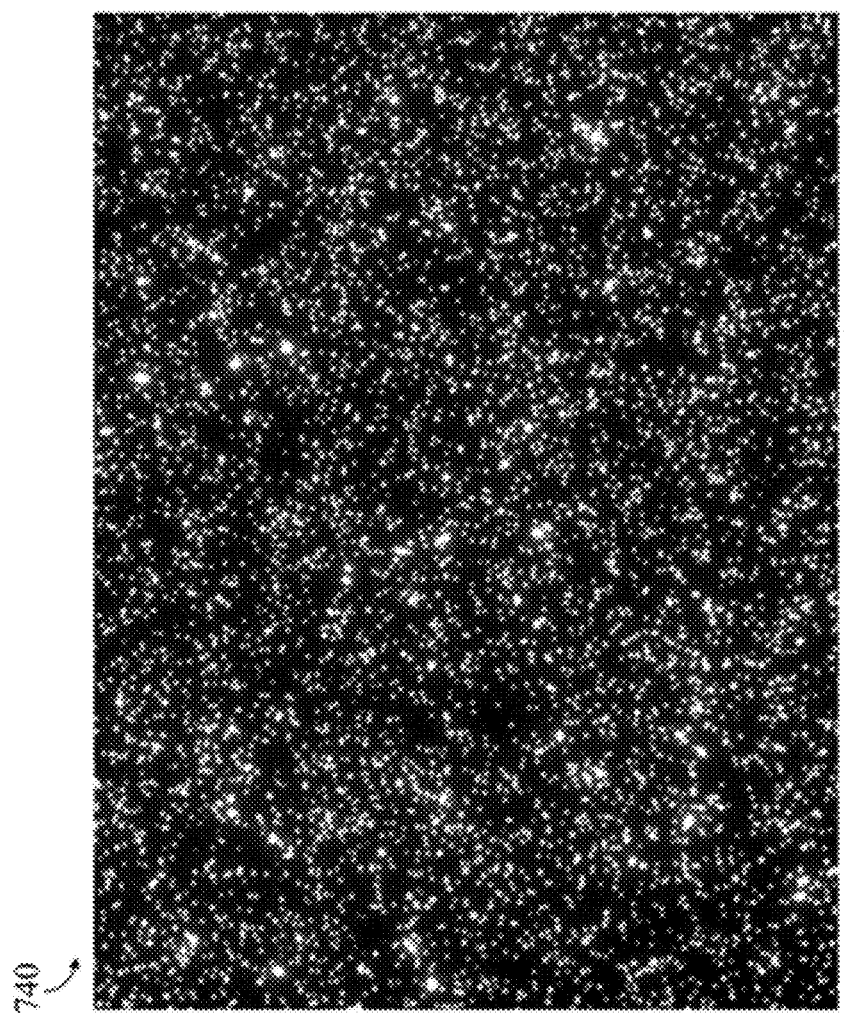
FIG. 7D shows an example a fluorescent image of RCA products from circularized double-stranded nucleic acids.
Figure 7C:
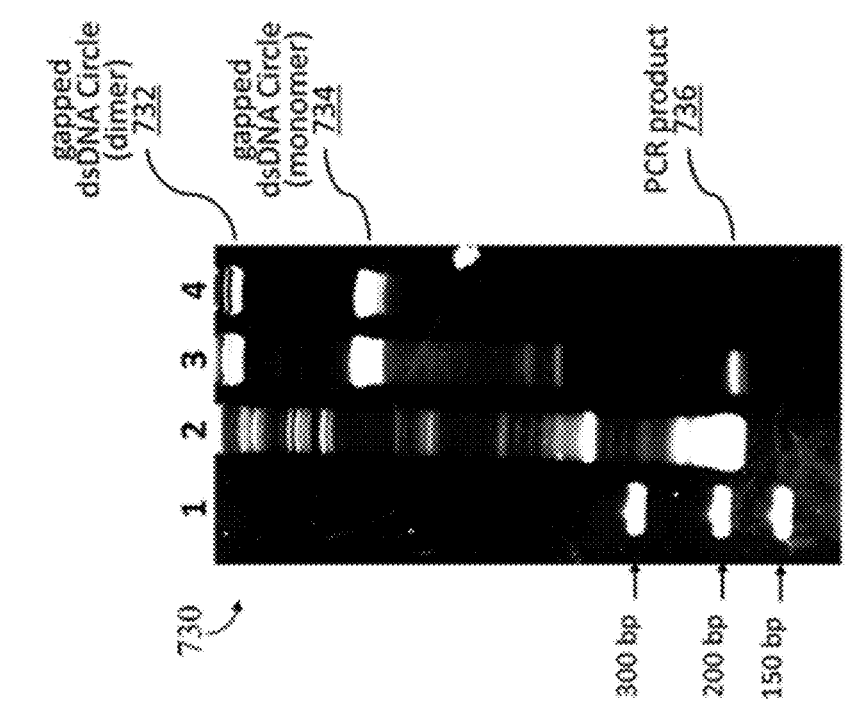
FIG. 7C shows an example of a gel electrophoresis image of a sample comprising a plurality of circularized double-stranded nucleic acids.

FIG. 7C shows an example gel electrophoresis image of a sample comprising a plurality of circularized double-stranded nucleic acids. A circular double-stranded DNA (circular dsDNA) may be generated from a biological sample or, alternatively, may be synthesized. The circular dsDNA may be used as a template to generate (e.g., via RCA by using a polymerase) into one or more DNRs. One or more purified 200-nucleotide circular dsDNA template, each comprising a nick may be prepared, in which about 90% may be present in the monomeric form in comparison to the dimeric form (lane 4). The resulting product may comprise a dimer of the circular dsDNA 732 (e.g., two non-covalently entangled circular dsDNA molecules) and a monomer of the circular dsDNA 734 and a non-detectable or minimally detectable amount of other PCR products. A 200 base-pair ssDNA may be prepared (e.g., synthesized) and amplified via PCR reactions. The PCR reactions may be performed using a forward oligonucleotide primer and a reverse oligonucleotide primer, each comprising nucleotide(s) or nucleotide modification(s) for enzymes to make a nucleotide gap. The PCR reactions may yield copies of a linear ssDNA and its complementary strand, and each strand may comprise nucleotide(s) or nucleotide modification(s) for enzymes to make a nucleotide gap and a sticky end. The dsDNA molecule may be circularized via hybridization between the two sticky ends and one ligation step (e.g., using T4 DNA ligase) to form a circular dsDNA comprising a sense strand and an anti-sense strand, along with a nucleotide gap in the sense strand or the anti-sense strand. DNA ladder control (lane 1), PCR products before purification (lane 2), and products of circularization and/or ligation reaction prior to treatment with Plasmid-Safe Dnase (lane3) may also be assessed. DNA samples may be resolved in 6% polyacrylamide gel electrophoresis 730 and stained with SYBR Green for visualization. FIG. 7D shows an example a fluorescent image of RCA products from circularized double-stranded nucleic acids. A polymerase (e.g., Phi29 polymerase) may be used to generate a plurality of DNRs from a plurality of the circular dsDNA comprising the 1-nucleotide nick in about 40 min RCA process.

Figure 8:
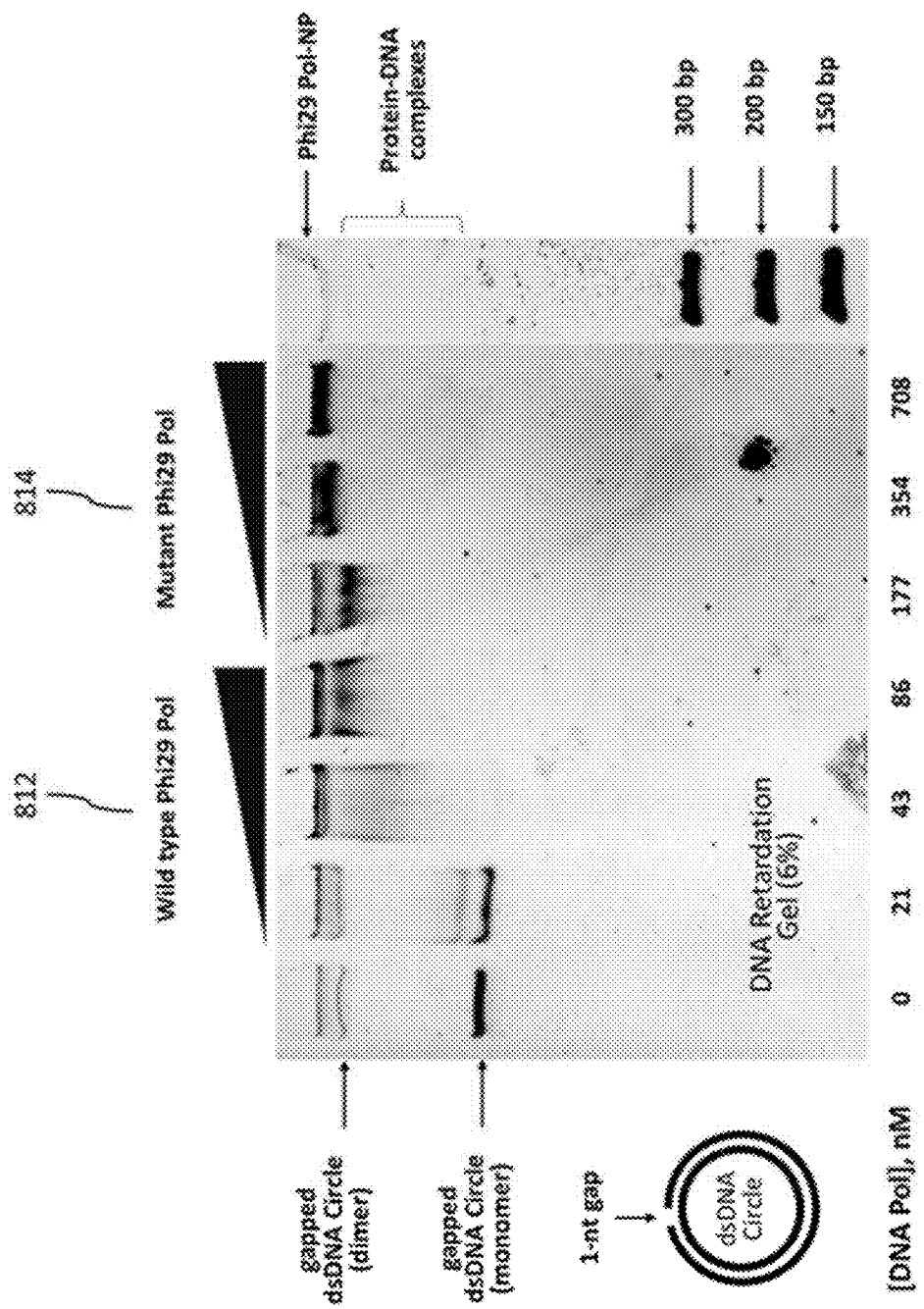
FIG. 8 shows an example of a gel electrophoresis image of complexation of a circular double-stranded nucleic acid and (i) a wild-type polymerase and (ii) a mutant polymerase

Example 3: Complexation of a Circular Double-Stranded Nucleic Acid Comprising a Nick and a Polymerase FIG. 8 shows an example gel electrophoresis image of complexation of a circular double-stranded nucleic acid and (i) a wild-type polymerase 812 (e.g., Wild type Phi29 Pol) and (ii) a mutant polymerase 814 (e.g., a mutant Phi29 Pol). Binding or at least one protein (e.g., enzyme) to at least one nucleic acid molecule may be assessed. The mutant polymerase 814 may comprise a linker, and the mutant polymerase-nanopore protein complex 816 may comprise the mutant polymerase that is coupled to the nanopore protein via the linker. Both wild-type Phi29 DNA polymerase and mutant Phi29 DNA polymerase may be capable of binding a 200 base-pair circular dsDNA template. The mobility of free DNA and polymerase-circular dsDNA complexes may be stained by SYBR Green for visualization.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing or analyzing a linear double-stranded nucleic acid molecule, comprising:
   (a) providing (i) said linear double-stranded nucleic acid molecule and (ii) a linear double-stranded adapter having a nicking site within a sense strand or an anti-sense strand of said linear double-stranded adapter;
   (b) coupling said linear double-stranded adapter to said linear double-stranded nucleic acid molecule;
   (c) circularizing said linear double-stranded nucleic acid molecule coupled to said linear double-stranded adapter, to generate a circularized double-stranded nucleic acid molecule; and
   (d) subjecting said circularized double-stranded nucleic acid molecule to sequencing from said nicking site in absence of linearizing said circularized double-stranded nucleic acid molecule.

2. The method of claim 1, wherein said linear double-stranded nucleic acid molecule and said linear double-stranded adapter are heterologous to one another.

3. The method of claim 1, wherein said sequencing comprises (i) subjecting said circularized double-stranded nucleic acid molecule to an extension reaction from said nicking site, to generate a growing strand having sequence complementarity to at least a portion of a strand of said linear double-stranded nucleic acid molecule, and (ii) obtaining sequence information of at least a portion of said growing strand.

4. The method of claim 3, wherein obtaining said sequence information comprises detecting said at least said portion of said growing strand.

5. The method of claim 3, wherein said extension reaction comprises bringing said circularized double-stranded nucleic acid molecule in contact with a nucleotide coupled to a tag under conditions sufficient to incorporate said nucleotide into said growing strand, and wherein obtaining said sequence information comprises detecting said tag.

6. The method of claim 3, wherein said extension reaction is performed without use of an oligonucleotide primer.

7. The method of claim 3, wherein said extension reaction comprises rolling circle amplification.

8. The method of claim 1, further comprising:
   (A) prior to said sequencing, using said nicking site to generate a nick; and
   (B) initiating said sequencing at said nick.

9. The method of claim 1, wherein, in (a), said nicking site comprises a nick, and wherein said method comprises initiating said sequencing at said nick.

10. The method of claim 1, wherein said coupling in (b) is performed in a cell-free composition.

11. The method of claim 1, wherein said circularizing in (c) is performed in a cell-free composition.

12. The method of claim 5, further comprising releasing said tag from said nucleotide upon incorporation of said nucleotide into said growing stand.

13. The method of claim 1, wherein said linear double-stranded nucleic acid molecule comprises a recognition sequence, and wherein said method further comprises enriching for said linear double-stranded nucleic acid molecule from a pool of nucleic acid molecules based at least in part on said recognition sequence.

14. The method of claim 13, wherein said enriching comprises (i) contacting said recognition sequence with a recognition moiety having complementarity with said recognition sequence to form a recognition complex, and (ii) extracting said recognition complex.

15. The method of claim 1, wherein said linear double-stranded nucleic acid molecule is derived from a biological sample of a subject.

16. The method of claim 15, wherein said biological sample comprises a cell-free biological sample of said subject.

17. The method of claim 15, wherein said biological sample comprises a tissue sample of said subject.

18. The method of claim 1, wherein said linear double-stranded nucleic acid molecule comprises deoxyribonucleic acid (DNA).

19. The method of claim 18, wherein said linear double stranded nucleic acid molecule comprises cell-free DNA or circulating tumor DNA.

20. The method of claim 1, wherein said linear double-stranded nucleic acid molecule comprises ribonucleic acid (RNA).

* * * * *

SEQUENCE LISTING

<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
attttagccc tggaaccttc agagagtacg acgatatatg ggaacaactg ctacctgct         59

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agcaggtagc agttgttccc at                                                 22